United States Patent
Luo et al.

(10) Patent No.: US 11,530,451 B2
(45) Date of Patent: Dec. 20, 2022

(54) METHODS FOR PROSTATE CANCER DETECTION

(71) Applicant: The Johns Hopkins University, Baltimore, MD (US)

(72) Inventors: Jun Luo, Clarksville, MD (US); Christian P. Pavlovich, Baltimore, MD (US); William Brewster Isaacs, Reisterstown, MD (US); Jillian N. Eskra, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 16/977,281

(22) PCT Filed: Mar. 1, 2019

(86) PCT No.: PCT/US2019/020410
§ 371 (c)(1),
(2) Date: Sep. 1, 2020

(87) PCT Pub. No.: WO2019/169336
PCT Pub. Date: Sep. 6, 2019

(65) Prior Publication Data
US 2021/0002729 A1 Jan. 7, 2021

Related U.S. Application Data

(60) Provisional application No. 62/637,601, filed on Mar. 2, 2018.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2013/0178393 A1 | 7/2013 | Doll et al. | |
| 2016/0002735 A1* | 1/2016 | Zhang | C12Q 1/6886 506/9 |
| 2016/0326594 A1* | 11/2016 | Srivastava | G01N 33/57434 |
| 2020/0140953 A1* | 5/2020 | Goel | C12Q 1/6886 |

FOREIGN PATENT DOCUMENTS

| | | |
|---|---|---|
| WO | 2006066965 A2 | 6/2006 |
| WO | 2014012176 A1 | 1/2014 |
| WO | 2015120416 A1 | 8/2015 |
| WO | 2016036994 A1 | 3/2016 |
| WO | 2015022164 A1 | 2/2019 |
| WO | PCT/US2019/020410 | 3/2019 |

OTHER PUBLICATIONS

U.S. Appl. No. 62/637,601, filed Mar. 2, 2018, Luo et al. (The Johns Hopkins University).
Torre LA, Bray F, Siegel RL, Ferlay J, Lortet-Tieulent J, Jemal A. Global cancer statistics, 2012. CA Cancer J Clin. 2015;65(2):87-108. Epub Feb. 6, 2015. doi: 10.3322/caac.21262. PubMed PMID: 25651787.
Walsh PC. Prostate Cancer Screening. N Engl J Med. 2017;376(24):2401-2. Epub Jun. 15, 2017. doi: 10.1056/NEJMc1705480. PubMed PMID: 28614679.
Shipley WU, Seiferheld W, Lukka HR, Major PP, Heney NM, Grignon DJ, Sartor O, Patel MP, Bahary JP, Zietman AL, Pisansky TM, Zeitzer KL, Lawton CA, Feng FY, Lovett RD, Balogh AG, Souhami L, Rosenthal SA, Kerlin KJ, Dignam JJ, Pugh SL, Sandler HM, Radiation with or without Antiandrogen Therapy in Recurrent Prostate Cancer. N Engl J Med. 2017;376(5):417-28. Epub Feb. 2, 2017. doi: 10.1056/NEJMoa1607529. PubMed PMID: 28146658; PMCID: PMC5444881.
Pinsky PF, Prorok PC, Kramer BJ. Prostate Cancer Screening. N Engl J Med. 2017;376(24):2402. Epub Jun. 15, 2017. doi: 10.1056/NEJMc1705480. PubMed PMID: 28614680.
Sharma V, Kames RJ, Prostatectomy versus Observation for Early Prostate Cancer. N Engl J Med. 2017;377(13):1302. Epub Sep. 28, 2017. doi: 10.1056/NEJMc1710384. PubMed PMID: 28953432.
Wallis CJD, Klotz L. Prostatectomy versus Observation for Early Prostate Cancer. N Engl J Med. 2017;377(13):1301-2. Epub Oct. 5, 2017. doi: 10.1056/NEJMc1710384. PubMed PMID: 28976174.
Wilt TJ, Andriole GL, Brawer MK. Prostatectomy versus Observation for Early Prostate Cancer, N Engl J Med. 2017;377(13):1302-3. Epub Sep. 28, 2017. doi: 10.1056/NEJMc1710384. PubMed PMID: 28953431.
Tosoian JJ, Carter HB. Active Surveillance of Localized Prostate Cancer: Acknowledging Uncertainty. J Clin Oncol. 2016;34(36):4452. Epub Dec. 22, 2016. doi: 10.1200/JCO.2016.67.8888. PubMed PMID: 27998229.
Carter HB. Optimizing Active Surveillance. Eur Urol. 2016;70(6):909-11. Epub Jul. 28, 2016. doi: 10.1016/j.eururo.2016.07.017. PubMed PMID: 27460354.
Hessels D, Jacqueline M T Klein Gunnewiek, Inge van Oort, Herbert F M Karthaus, Geert J L van Leenders, Bianca van Balkan, Lambertus A Kiemeney, J Alfred Witjes, Jack A Schalken. (2003) DD3(PCA3)-based molecular urine analysis for the diagnosis of prostate cancer, European urology 44(1):8-15; discussion 15-16.

(Continued)

*Primary Examiner* — Katherine D Salmon
(74) *Attorney, Agent, or Firm* — Ballard Spahr LLP

(57) ABSTRACT

Disclosed herein are methods for a RNA in situ hybridization assay workflow for the detection of target RNA within intact cells for the detection of prostate cancer cells in urine samples. The methods disclosed herein can identify a genetic susceptibility to prostate cancer in a subject and differentiate high risk from low risk prostate cancers. The methods disclosed herein can also include treatment and management strategies for prostate cancer and the prevention thereof.

8 Claims, 23 Drawing Sheets

(56) References Cited

OTHER PUBLICATIONS

Truong M, Yang B, Jarrard DF. Toward the detection of prostate cancer in urine: a critical analysis. J Urol. 2013;189(2):422-9. Epub Sep. 29, 2012. doi: 10.1016/j.juro.2012.04.143. PubMed PMID: 23017522; PMCID: PMC3581046.

Gonzalgo ML, Pavlovich CP, Lee SM, Nelson WG. Prostate cancer detection by GSTP1 methylation analysis of postbiopsy urine specimens. Clin Cancer Res. 2003;9(7):2673-7. Epub Jul. 12, 2003. PubMed PMID: 12855646.

Rogers CG, Yan G, Zha S, Gonzalgo ML, Isaacs WB, Luo J, De Marzo AM, Nelson WG, Pavlovich CP. Prostate cancer detection on urinalysis for alpha methylacyl coenzyme a racemase protein. J Urol. 2004;172(4 Pt 1):1501-3. Epub Sep. 17, 2004. PubMed PMID: 15371879.

Albers DD, Mc DJ, Thompson GJ. Carcinoma cells in prostatic secretions. J Am Med Assoc. 1949;139(5):299-303. Epub Jan. 29, 1949. PubMed PMID: 18123171.

Bologna M, Vicentini C, Festuccia C, Muzi P, Napolitano T, Biordi L, Miano L. Early diagnosis of prostatic carcinoma based on in vitro culture of viable tumor cells harvested by prostatic massage. Eur Urol. 1988;14(6):474-6. Epub Jan. 1, 1988. PubMed PMID: 3181228.

Garret M, Jassie M. Cytologic examination of post prostatic massage specimens as an aid in diagnosis of carcinoma of the prostate. Acta Cytol. 1976;20(2):126-31. Epub Mar. 1, 1976. PubMed PMID: 1065172.

Koss LG, Deitch D, Ramanathan R, Sherman AB. Diagnostic value of cytology of voided urine. Acta Cytol. 1985;29(5):810-6. Epub Sep. 1, 1985. PubMed PMID: 3863429.

Sharifi R, Shaw M, Ray V, Rhee H, Nagubadi S, Guinan P. Evaluation of cytologic techniques for diagnosis of prostate cancer. Urology. 1983;21(4):417-20. Epub Apr. 1, 1983. PubMed PMID: 6836839.

Luo J, Zha S, Gage WR, Dunn TA, Hicks JL, Bennett CJ, Ewing CM, Platz EA, Ferdinandusse S, Wanders RJ, Trent JM, Isaacs WB, De Marzo AM. Alpha-methylacyl-CoA racemase: a new molecular marker for prostate cancer. Cancer Res. 2002;62(8):2220-6. Epub Apr. 17, 2002. PubMed PMID: 11956072.

Fujita K, Pavlovich CP, Netto GJ, Konishi Y, Isaacs WB, Ali S, De Marzo A, Meeker AK. Specific detection of prostate cancer cells in urine by multiplex immunofluorescence cytology. Hum Pathol. 2009;40(7):924-33. Epub Apr. 17, 2009. doi: 10.1016/j.humpath. 2009.01.004. PubMed PMID: 19368959; PMCID: PMC2757169.

D'Amico AV, Whittington R, Malkowicz SB, et al. Biochemical Outcome After Radical Prostatectomy, External Beam Radiation Therapy, or Interstitial Radiation Therapy for Clinically Localized Prostate Cancer. JAMA. 1998;280(11):969-974. doi:10.1001/jama. 280.11.969.

Epstein JI, Walsh PC, Carmichael M, Brendler CB. Pathologic and clinical findings to predict tumor extent of nonpalpable (stage T1c) prostate cancer, JAMA. Feb. 2, 1994;271(5):368-74. PMID: 7506797.

Varma VA, Fekete PS, Franks MJ, & Walther MM (1988) Cytologic features of prostatic adenocarcinoma in urine: a clinicopathologic and immunocytochemical study. Diagnostic cytopathology 4(4):300-305.

Hessels D, Schalken JA. The use of PCA3 in the diagnosis of prostate cancer. Nat Rev Urol. May 2009;6(5):255-61. doi: 10.1038/nrurol.2009.40. PMID: 19424173.

Tosoian JJ, Ross AE, Sokoll LJ, Partin AW, & Pavlovich CP (2016) Urinary Biomarkers for Prostate Cancer. The Urologic clinics of North America 43(1):17-38.

Rupp M, O'Hara B, McCullough L, Saxena S, & Olchiewski J (1994) Prostatic carcinoma cells in urine specimens. Cytopathology : official journal of the British Society for Clinical Cytology 5(3):164-170.

Scott WW & Huggins C (1942) The acid phosphatase activity of human urine, an index of prostatic secretion. Endocrinology 30(1):107-112.

Breul J, Pickl U, & Hartung R (1994) Prostate-specific antigen in urine. European urology 26(1):18-21.

Moberg PJ, Lizana J, & Eneroth P (1984) Analysis of Prostatic Acid Phosphatase in Urine Voided before and after Massage of the Prostate in Infertile Men. Urologia Internationalis 39(4):189-192.

Rianne J Hendriks, Siebren Dijkstra, Sander A Jannink, Martijn G Steffens, Inge M van Oort, Peter F A Mulders, Jack A Schalken (2016) Comparative analysis of prostate cancer specific biomarkers PCA3 and ERG in whole urine, urinary sediments and exosomes. Clinical chemistry and laboratory medicine 54(3):483.

Papanicolaou GN & Marshall VF (1945) Urine sediment smears as a diagnostic procedure in cancers of the urinary tract. Science (New York, N.Y.) 101(2629):519-520.

Nickens KP, Amina Ali, Tatiana Scoggin, Shyh-Han Tan, Lakshmi Ravindranath, David G McLeod, Albert Dobi, David Tacha, Isabell A Sesterhenn, Shiv Srivastava, Gyorgy Petrovics (2015) Prostate cancer marker panel with single cell sensitivity in urine. Prostate 75(9):969-975.

Eastman, James, Prostate Cancer Screening. Investig Clin Urol, 2017;58:217-219, https://doi.org/10.4111/icu.2017.58.4.217, pISSN 2466-0493 * eISSN 2466-054X.

* cited by examiner

Fig. 4E PCA3
Fig. 4D AMACR
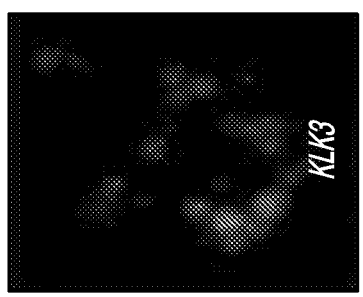
Fig. 4C KLK3
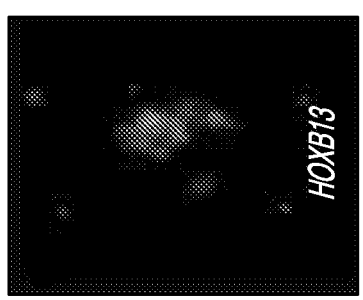
Fig. 4B HOXB13
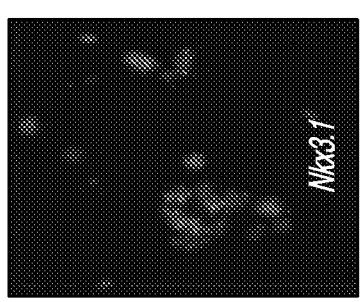
Fig. 4A Nkx3.1
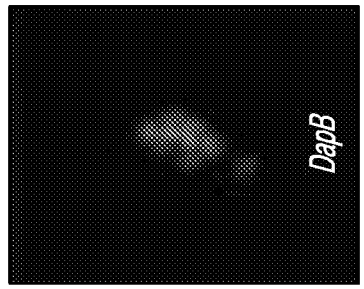
Fig. 4J DapB
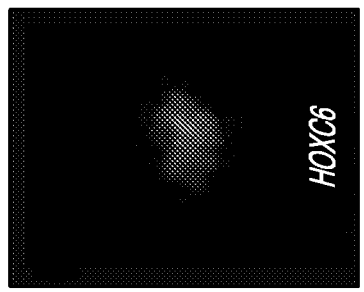
Fig. 4I HOXC6
Fig. 4H MALAT1
Fig. 4G PRAC2
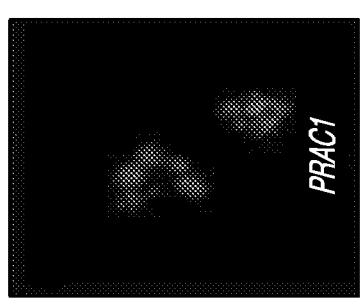
Fig. 4F PRAC1

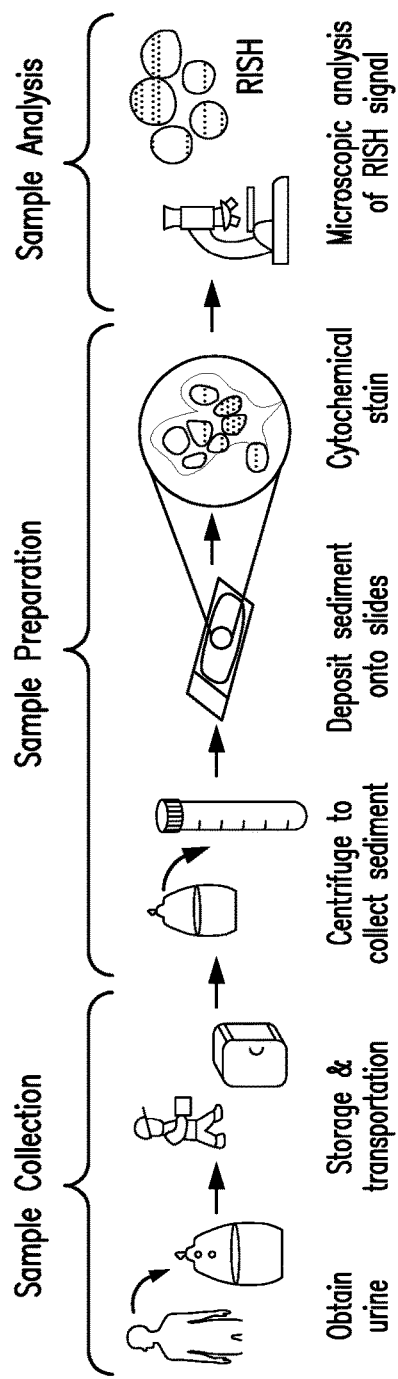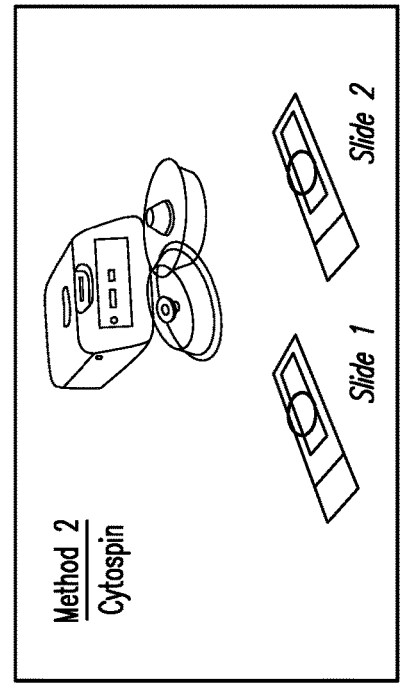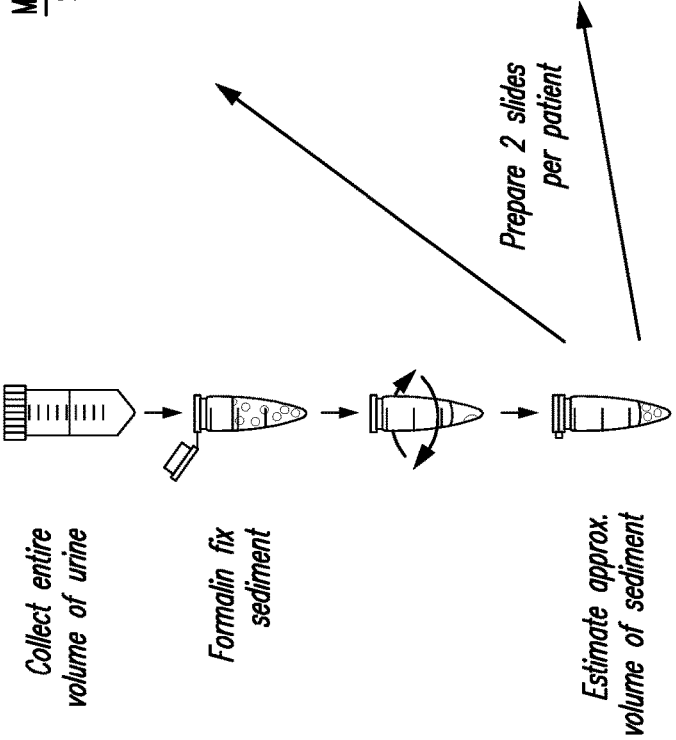

Fig. 12A  Fig. 12B
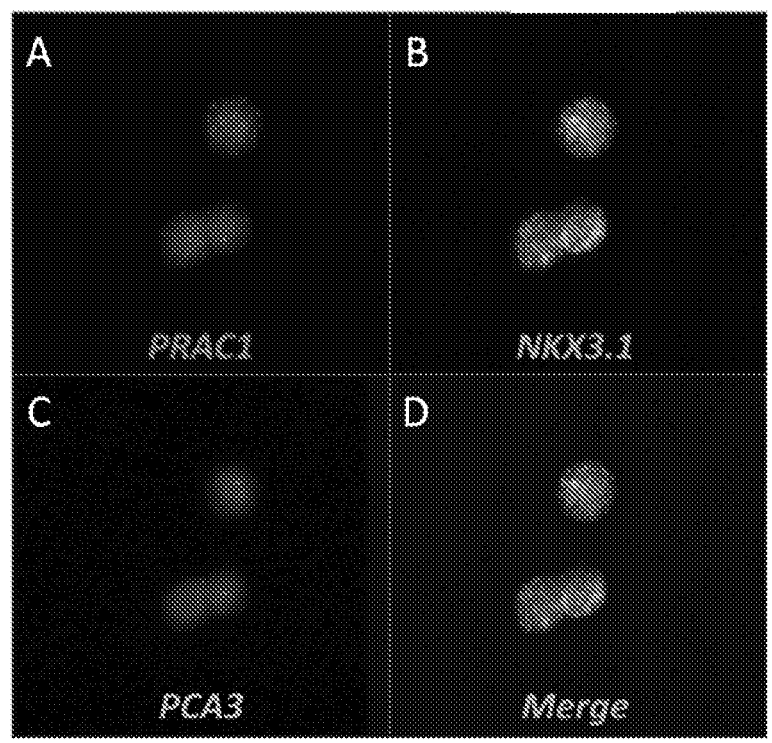
Fig. 12C  Fig. 12D
Fig. 13A  Fig. 13B
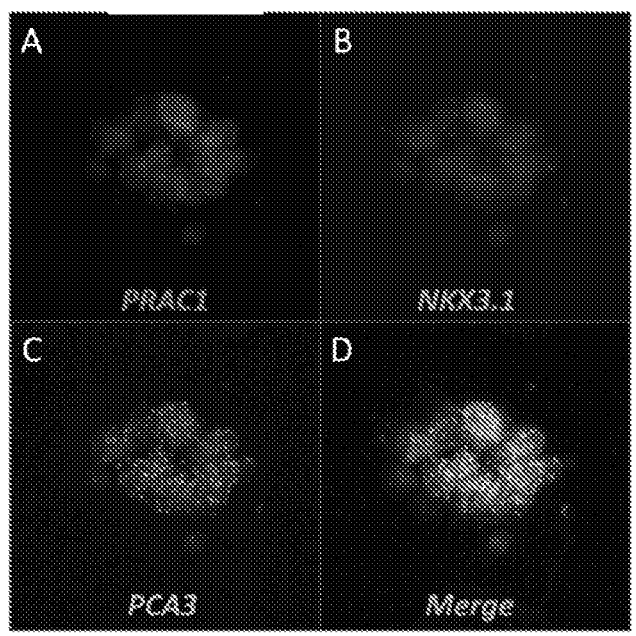
Fig. 13C  Fig. 13D

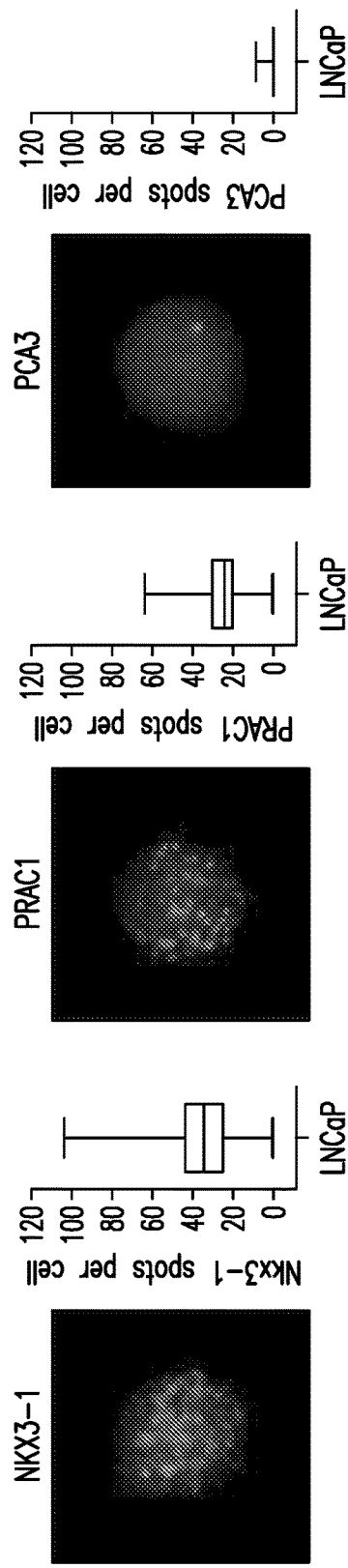
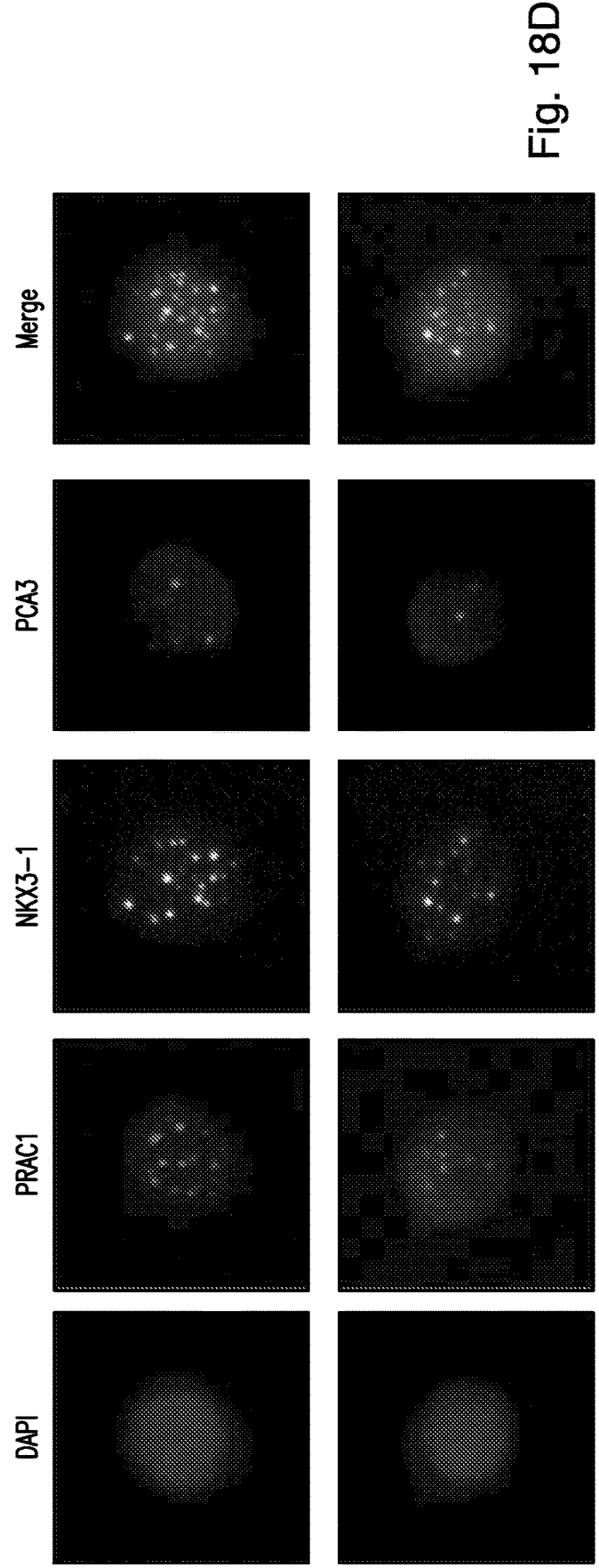

Fig. 19A
Fig. 19B
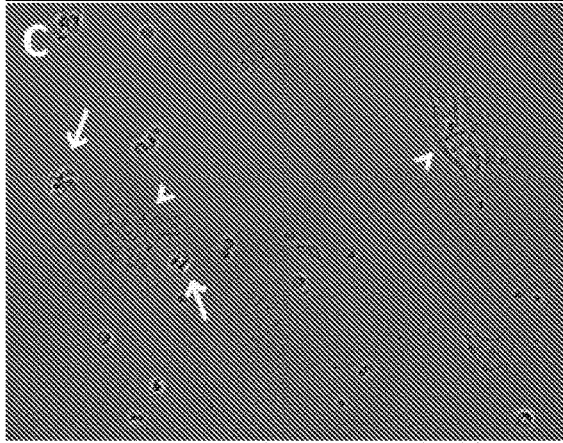
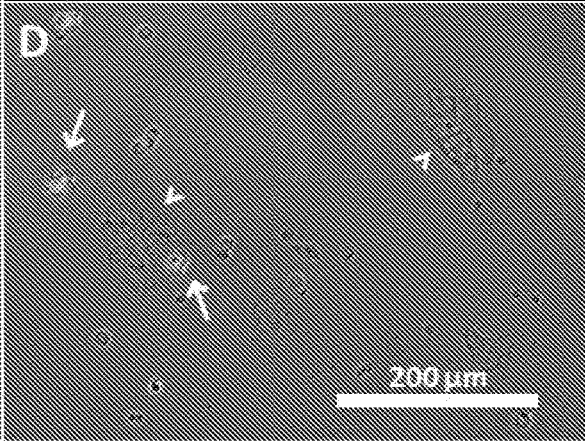
Fig. 19C
Fig. 19D

METHODS FOR PROSTATE CANCER DETECTION

CROSS REFERENCE TO RELATED APPLICATIONS

This application claims the benefit of priority under 35 U.S.C. 371 of International Application No. PCT/US2019/020410, filed on Mar. 1, 2019, which claims the benefit of the filing date of U.S. Provisional Application No. 62/637,601, filed on Mar. 2, 2018. The content of these earlier filed applications is hereby incorporated by reference herein in its entirety.

BACKGROUND

Prostate cancer remains one of the most commonly diagnosed cancers in the aging male population worldwide (Torre L A et al., CA Cancer J Clin. 2015; 65(2):87-108. Epub 2015/02/06). In the US, the serum PSA test continues to play an important role in prostate cancer screening, detection, prognosis, and disease monitoring. Many contemporary problems in prostate cancer detection and management arise from the lack of precision of existing screening and detection methods (Walsh P C. N Engl J Med. 2017; 376(24):2401-2; Shipley W U, et al., N Engl J Med. 2017; 376(5):417-28; Pinsky P F, et al., N Engl J Med. 2017; 376(24):2402; Sharma V, et al., N Engl J Med. 2017; 377(13):1302; Wallis C J D and Klotz L, N Engl J Med. 2017; 377(13):1301-2; and Wilt T J, et al., N Engl J Med. 2017; 377(13):1302-3). For example, in the diagnostic setting, sensitivity for prostate cancer detection in men with indications for prostate needle biopsy (e.g., elevated PSA and abnormal digital rectal examination (DRE) findings) is usually high. However, among the roughly one million prostate biopsies performed annually in the United States alone, the majority find no cancer. In addition, prostate biopsies often result in the diagnosis of clinically insignificant cancers, contributing to prostate cancer overtreatment (Tosoian J J and Carter H B. J Clin Oncol. 2016; 34(36):4452; and Carter H B. Eur Urol. 2016; 70(6):909-11). Finally, prostate biopsies are usually performed transrectally and thus may subject patients to side-effects including bleeding, pain, and potentially serious infections. The lack of specificity in the traditional biopsy pathway for prostate cancer diagnosis, therefore, underlies many of the clinical dilemmas, including the need for initial and repeat biopsy as well as the type and timing of definitive local and/or systemic treatment. Development of less invasive and more accurate methods of prostate cancer diagnosis, particularly of aggressive/high-risk cancers, would help to reduce unnecessary biopsies and improve precision management of men diagnosed with prostate cancer.

BRIEF DESCRIPTION OF THE DRAWINGS

FIGS. 2A-B shows urothelial cells; FIG. 2C shows a urothelial cell with bacteria; FIG. 2D shows a cluster of spermatozoa; FIG. 2E shows corpora amylacea (arrow); FIG. 2F shows inflammation, bacteria and red blood cells; FIG. 2G shows inflammatory cells; FIG. 2H shows bacteria; FIG. 2I shows degraded cells and debris; and FIG. 2J shows 22Rv1 cells spiked into urine (arrows).

FIGS. 4A-J show the results of fluorescent RNA-ish of prostate probes performed on Cytospin preparation of urine samples spiked with 22Rv1 cells. FIG. 4A shows Nkx3.1; FIG. 4B shows HOXB12; FIG. 4C shows KLK3; FIG. 4D shows AMACR; FIG. 4E shows PCA3; FIG. 4F shows PRAC1; FIG. 4G shows PRAC2; FIG. 4H shows MALAT1; FIG. 4I shows HOXC6; and FIG. 4J shows DapB (negative control).

FIG. 5 shows the workflow overview of processing a sample from sample collection, sample preparation to sample analysis.

FIG. 6 is a schematic slide preparation.

FIGS. 12A-D shows multiplex RISH performed on urine samples spiked with 22Rv1 cells. FIG. 12A shows PRAC1; FIG. 12B shows NKX3.1; FIG. 12C shows PCA3; and FIG. 12D shows the merge. Counterstained with DAPI.

FIGS. 13A-D show prostate cancer cells (often in clusters) detected in post-DRE urine sediments obtained from patients with prostate cancer in patient sample 1. Multiplex RISH for PRAC1 (A), NKX3.1 (B), and PCA3 (C); counterstained with DAPI.

FIG. 17A shows the efficiency of cell recovery following Cytospin slide preparation. FIG. 17B shows the percentage of cells adherent to slide following various pretreatment conditions. FIG. 17C shows the percentage of cells adherent to slide after each RISH steps. FIGS. 17D, E, and F are box and whisker plots showing spot quantification for cells spiked into urine and stored for 0, 2, 4, and 6 hours at 4° C.

FIGS. 18A-D representative images of RISH spots and the results of multiplex labeling for simultaneous detection. Representative images of RISH spots (green) in LNCaP cells for NKX3-1 (A), PRAC1 (B), and PCA3 (C), counterstained with DAPI (blue). The number of spots per cell was quantified in at least 500 cells for each marker and results are depicted in corresponding box and whisker plots; Multiplex RISH for PRAC1 (red), NKX3-1 (white), and PCA3 (green) in LNCaP cells (D).

FIGS. 19A-D show RISH performed on urine samples spiked with 22Rv1 cells. FIG. 19A shows NKX3-1 (green), FIG. 19B shows DAPI (blue), FIG. 19C shows phase contrast, and FIG. 19D shows merge. Arrow indicating clusters of 22Rv1 cells, arrowheads indicating urothelial cells.

SUMMARY

Figure 1:
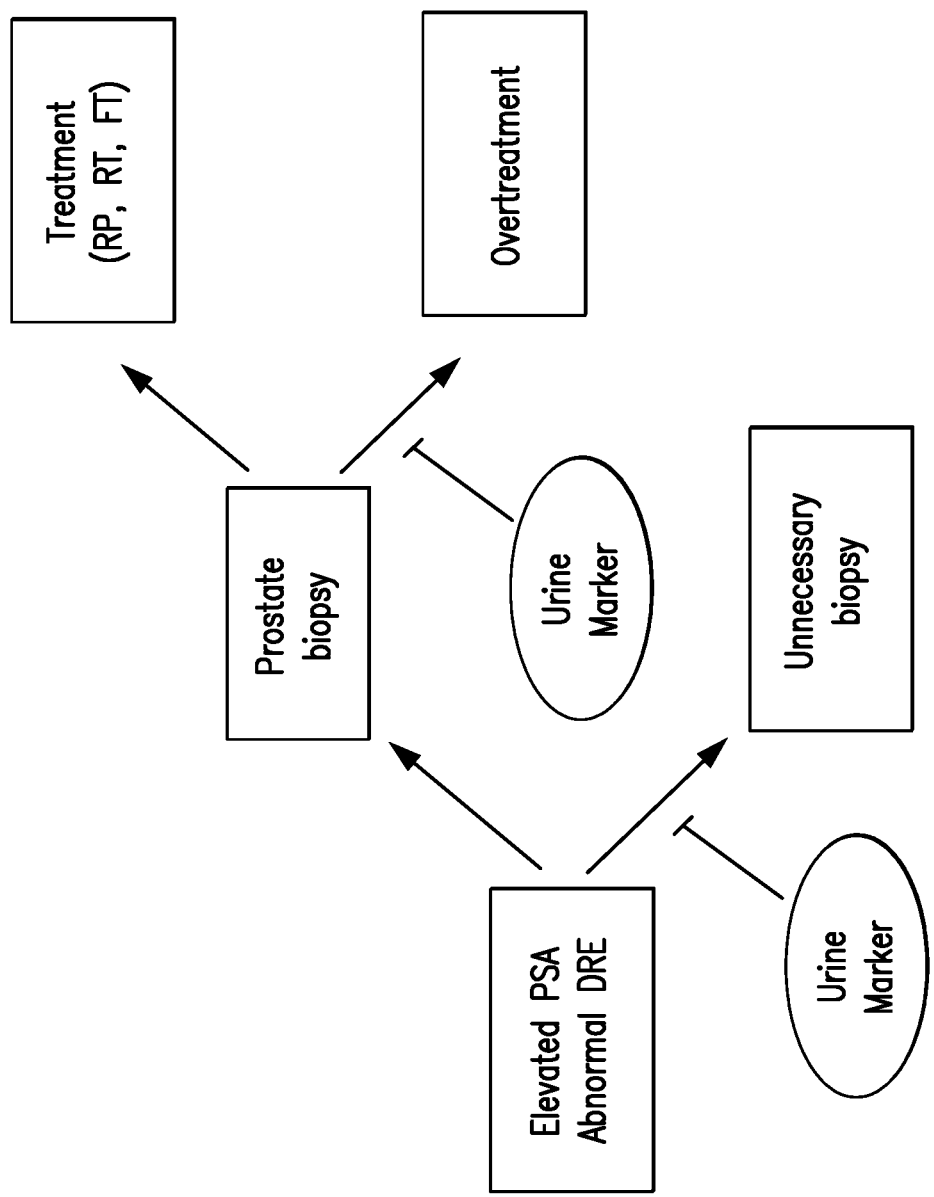
FIG. 1 is a schematic showing the noninvasive urine-based markers that have the potential to disrupt the traditional biopsy pathway for prostate cancer detection and treatment by reducing unnecessary biopsies and overtreatment. RP: radical prostatectomy; RT: radiation therapy; FT: focal therapies.
Figure 2A:
FIGS. 2A-J shows the results of papanicolaou stained urine sediments obtained from clinical urine specimens (A-I) and 22Rv1-spiked urine (J).
Figure 2B:
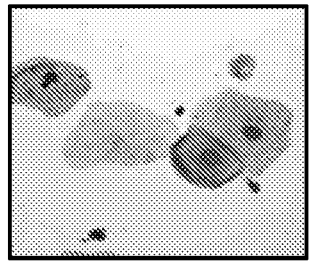
Figure 2C:
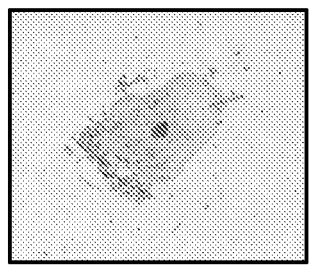
Figure 2D:
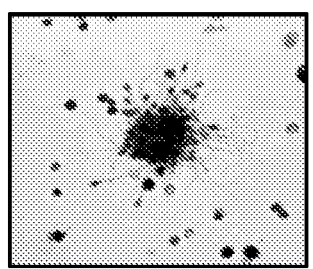
Figure 2E:
Figure 2F:
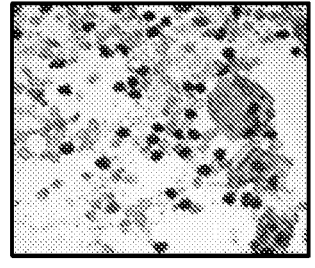
Figure 2G:
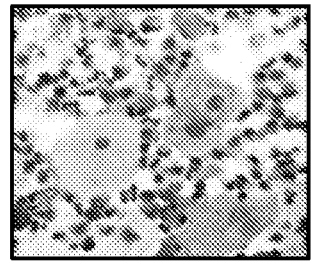
Figure 2H:
Figure 2I:
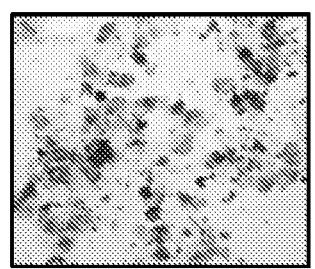
Figure 2J:
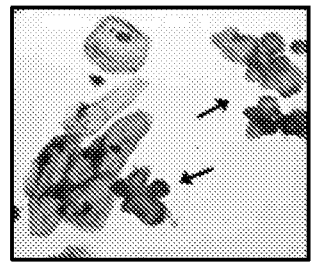
Figure 3B:
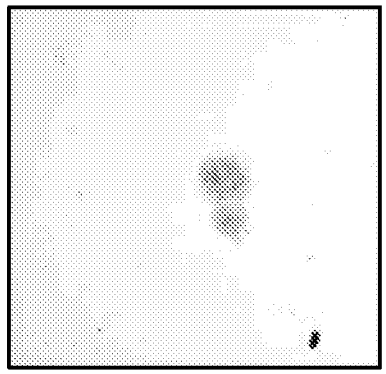
FIGS. 3A-D show chromogenic RNA-ISH for Nkx3.1 (A, B) and HoxB12 (C, D) with 22Rv1 spiked urine (A, C) and clinical urine specimen (B, D); counterstained with hematoxylin.
Figure 3D:
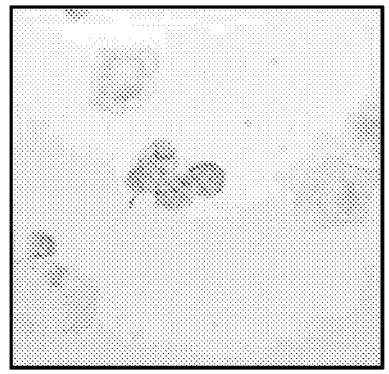
Figure 3A:
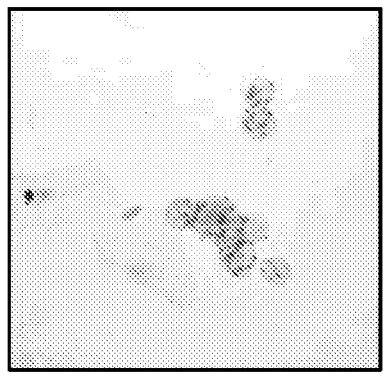
Figure 3C:
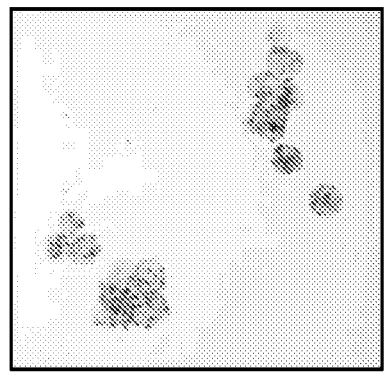

Disclosed herein are methods of diagnosing a human subject with an increased susceptibility for prostate cancer, the methods comprising: a) obtaining an urine sample in the subject; b) determining the mRNA expression level of one or more of NKX3.1, HOXB13, KLK3, PRAC1, PRAC2, MALAT1, HOXC6, AMACR, SCHLAP1, PCAT1, and PCA3 in the sample from the subject; c) obtaining a reference mRNA expression level for one or more of NKX3.1, HOXB13, KLK3, PRAC1, PRAC2, MALAT1, HOXC6, AMACR, SCHLAP1, PCAT1, and PCA3 from a normal control; d) comparing the expression level for one or more of NKX3.1, HOXB13, KLK3, PRAC1, PRAC2, MALAT1, HOXC6, AMACR, SCHLAP1, PCAT1, and PCA3 of step b) with the reference expression level for one or more of NKX3.1, HOXB13, KLK3, PRAC1, PRAC2, MALAT1, HOXC6, AMACR, SCHLAP1, PCAT1, and PCA3 of step c); and e) determining that the subject has an increased susceptibility to prostate cancer wherein a ratio of the sample expression level of one or more of NKX3.1, HOXB13, KLK3, PRAC1, PRAC2, MALAT1, HOXC6, AMACR, SCHLAP1, PCAT1, and PCA3 to the reference expression level of one or more of NKX3.1, HOXB13, KLK3, PRAC1, PRAC2, MALAT1, HOXC6, AMACR, SCHLAP1, PCAT1, and PCA3 indicates higher expression level of NKX3.1, HOXB13, KLK3, PRAC1, PRAC2, MALAT1, HOXC6, AMACR, SCHLAP1, PCAT1, and PCA3 in the sample.

Disclosed herein are methods of diagnosing a human subject with an increased susceptibility for prostate cancer, the methods comprising: a) obtaining an urine sample in the subject; b) determining the mRNA expression level of one or more of NKX3.1, HOXB13, KLK3, PRAC1, PRAC2, MALAT1, HOXC6, AMACR, SCHLAP1, PCAT1, and PCA3 in the sample from the subject; c) obtaining a reference mRNA expression level for one or more of NKX3.1, HOXB13, KLK3, PRAC1, PRAC2, MALAT1, HOXC6, AMACR, SCHLAP1, PCAT1, and PCA3 from a normal control; d) comparing the expression level for one or more of NKX3.1, HOXB13, KLK3, PRAC1, PRAC2, MALAT1, HOXC6, AMACR, SCHLAP1, PCAT1, and PCA3 of step b) with the reference expression level for one or more of NKX3.1, HOXB13, KLK3, PRAC1, PRAC2, MALAT1, HOXC6, AMACR, SCHLAP1, PCAT1, and PCA3 of step c); and e) determining that the subject has an increased susceptibility to prostate cancer wherein a ratio of the sample expression level of one or more of NKX3.1, HOXB13, KLK3, PRAC1, PRAC2, MALAT1, HOXC6, AMACR, SCHLAP1, PCAT1, and PCA3 to the reference expression level of one or more of NKX3.1, HOXB13, KLK3, PRAC1, PRAC2, MALAT1, HOXC6, AMACR, SCHLAP1, PCAT1, and PCA3 indicates higher expression level of NKX3.1, HOXB13, KLK3, PRAC1, PRAC2, MALAT1, HOXC6, AMACR, SCHLAP1, PCAT1, and PCA3 in the sample.

Disclosed herein are methods of diagnosing a human subject with an increased susceptibility for prostate cancer, the methods comprising: a) obtaining an urine sample in the subject; b) determining the mRNA expression level of one or more of NKX3.1, HOXB13, KLK3, PRAC1, PRAC2, MALAT1, HOXC6, AMACR, SCHLAP1, PCAT1, and PCA3 in the sample from the subject; c) determining that the subject has an increased susceptibility to prostate cancer based on a pre-determined pattern of one or more of NKX3.1, HOXB13, KLK3, PRAC1, PRAC2, MALAT1, HOXC6, AMACR, SCHLAP1, PCAT1, and PCA3 in the sample.

Disclosed herein are diagnostic devices, comprising biomarkers, wherein the biomarkers are one or more of NKX3.1, HOXB13, KLK3, PRAC1, PRAC2, MALAT1, HOXC6, AMACR, SCHLAP1, PCAT1, and PCA3.

Disclosed herein gene expression panels for assessing risk of developing prostate cancer in human subjects, consisting of primers or probes for amplifying or detecting one or more of NKX3.1, HOXB13, KLK3, PRAC1, PRAC2, MALAT1, HOXC6, AMACR, SCHLAP1, PCAT1, and PCA3 in a sample.

Disclosed herein are methods of diagnosing and treating a low or high risk tumor in a subject with prostate cancer, the method comprising: a) obtaining a sample from a subject with prostate cancer; b) detecting expression levels of one or more of NKX3.1, HOXB13, KLK3, PRAC1, PRAC2, MALAT1, HOXC6, AMACR, SCHLAP1, PCAT1, and PCA3 in the sample and determining whether the expression levels of one or more of NKX3.1, HOXB13, KLK3, PRAC1, PRAC2, MALAT1, HOXC6, AMACR, SCHLAP1, PCAT1, and PCA3 are higher or lower compared to expression levels of one or more of NKX3.1, HOXB13, KLK3, PRAC1, PRAC2, MALAT1, HOXC6, AMACR, SCHLAP1, PCAT1, and PCA3 from a reference sample; c) diagnosing the subject with a low risk tumor when the expression levels of one or more of NKX3.1, HOXB13, KLK3, PRAC1, PRAC2, MALAT1, HOXC6, AMACR, SCHLAP1, PCAT1, and PCA3 in the sample are lower compared to expression levels of genes of one or more of NKX3.1, HOXB13, KLK3, PRAC1, PRAC2, MALAT1, HOXC6, AMACR, SCHLAP1, PCAT1, and PCA3 from a reference sample or diagnosing the subject with a high risk tumor when the expression levels of one or more of NKX3.1, HOXB13, KLK3, PRAC1, PRAC2, MALAT1, HOXC6, AMACR, SCHLAP1, PCAT1, and PCA3 in the sample are higher compared to expression levels of one or more of NKX3.1, HOXB13, KLK3, PRAC1, PRAC2, MALAT1, HOXC6, AMACR, SCHLAP1, PCAT1, and PCA3 from a reference sample; and d) withholding prostatectomy, radiation, chemotherapy, castration, anti-androgen therapy or a combination thereof from the subject with a low risk tumor or administering a lower dose of radiation, chemotherapy anti-androgen therapy or a combination thereof to the subject with a low risk tumor or administering treatment of prostatectomy, radiation, chemotherapy, castration or a combination thereof to the subject with a high risk tumor.

Disclosed herein are methods of diagnosing and treating a low or high risk tumor in a subject with prostate cancer, the method comprising: a) obtaining a sample from a subject with prostate cancer; b) detecting expression levels of one or more of NKX3.1, HOXB13, KLK3, PRAC1, PRAC2, MALAT1, HOXC6, AMACR, SCHLAP1, PCAT1, and PCA3 in the sample and determining the expression levels of one or more of NKX3.1, HOXB13, KLK3, PRAC1, PRAC2, MALAT1, HOXC6, AMACR, SCHLAP1, PCAT1, and PCA3 based on a pre-determined pattern of one or more of NKX3.1, HOXB13, KLK3, PRAC1, PRAC2, MALAT1, HOXC6, AMACR, SCHLAP1, PCAT1, and PCA3 in the sample; c) diagnosing the subject has a low risk tumor when the expression levels of one or more of NKX3.1, HOXB13, KLK3, PRAC1, PRAC2, MALAT1, HOXC6, AMACR, SCHLAP1, PCAT1, and PCA3 are based on the pre-determined pattern of one or more of NKX3.1, HOXB13, KLK3, PRAC1, PRAC2, MALAT1, HOXC6, AMACR, SCHLAP1, PCAT1, and PCA3 in the sample; and d) withholding prostatectomy, radiation, chemotherapy, castration, anti-androgen therapy or a combination thereof from the subject with a low risk tumor or administering a lower dose of radiation, chemotherapy anti-androgen therapy or a combination thereof to the subject with a low risk tumor or administering treatment of prostatectomy, radiation, chemotherapy, castration or a combination thereof to the subject with a high risk tumor.

In an aspect, the expression level of one or more of NKX3.1, HOXB13, KLK3, PRAC1, PRAC2, MALAT1, HOXC6, AMACR, SCHLAP1, PCAT1, and PCA3 can be an RNA expression level. In an aspect, the amount of RNA can be determined by RNA in situ hybridization.

Disclosed herein are methods of determining the mRNA expression level of one or more of NKX3.1, HOXB13, KLK3, PRAC1, PRAC2, MALAT1, HOXC6, AMACR, SCHLAP1, PCAT1, and PCA3 in the sample. In an aspect, the method can comprise: a) obtaining a sample in the subject; and b) determining the mRNA expression level of one or more of NKX3.1, HOXB13, KLK3, PRAC1, PRAC2, MALAT1, HOXC6, AMACR, SCHLAP1, PCAT1, and PCA3 in the sample from the subject. In an aspect, the method can include determining the mRNA expression level using RNA in situ hybridization (RISH).

Disclosed herein are methods of treating high risk tumors in a subject with prostate cancer, the methods comprising: administering a treatment of prostatectomy, radiation, chemotherapy, castration or a combination thereof in a subject diagnosed as having a high risk tumor by: 1) obtaining a sample from a subject with prostate cancer; 2) detecting expression levels of one or more of NKX3.1, HOXB13, KLK3, PRAC1, PRAC2, MALAT1, HOXC6, AMACR, SCHLAP1, PCAT1, and PCA3 in a sample and determining whether the expression levels of one or more of NKX3.1, HOXB13, KLK3, PRAC1, PRAC2, MALAT1, HOXC6, AMACR, SCHLAP1, PCAT1, and PCA3 are higher or lower compared to expression levels of one or more of NKX3.1, HOXB13, KLK3, PRAC1, PRAC2, MALAT1, HOXC6, AMACR, SCHLAP1, PCAT1, and PCA3 from a reference sample; and 3) diagnosing the subject with a high risk tumor when the expression levels of one or more of NKX3.1, HOXB13, KLK3, PRAC1, PRAC2, MALAT1, HOXC6, AMACR, SCHLAP1, PCAT1, and PCA3 in the sample are higher compared to the expression level of one or more of NKX3.1, HOXB13, KLK3, PRAC1, PRAC2, MALAT1, HOXC6, AMACR, SCHLAP1, PCAT1, and PCA3 from a reference sample.

Disclosed herein are methods of treating high risk tumors in a subject with prostate cancer, the methods comprising: administering a treatment of prostatectomy, radiation, chemotherapy, castration or a combination thereof in a subject diagnosed as having a high risk tumor by: 1) obtaining a sample from a subject with prostate cancer; 2) detecting expression levels of one or more of NKX3.1, HOXB13, KLK3, PRAC1, PRAC2, MALAT1, HOXC6, AMACR, SCHLAP1, PCAT1, and PCA3 in a sample based on the pre-determined pattern of one or more of NKX3.1, HOXB13, KLK3, PRAC1, PRAC2, MALAT1, HOXC6, AMACR, SCHLAP1, PCAT1, and PCA3 in the sample; and 3) diagnosing the subject with a high risk tumor when the expression levels of one or more of NKX3.1, HOXB13, KLK3, PRAC1, PRAC2, MALAT1, HOXC6, AMACR, SCHLAP1, PCAT1, and PCA3 in the sample detected based on the pre-determined pattern of one or more of NKX3.1, HOXB13, KLK3, PRAC1, PRAC2, MALAT1, HOXC6, AMACR, SCHLAP1, PCAT1, and PCA3 in the sample Disclosed herein are methods of treating low risk tumors in a subject with prostate cancer, the methods comprising: withholding prostatectomy, radiation, chemotherapy, castration, anti-androgen therapy or a combination thereof from the subject with a low risk tumor administering a lower dose of radiation, chemotherapy, anti-androgen therapy or a combination thereof to the subject with a low risk tumor, wherein the subject was diagnosed as having a high risk tumor by: 1) obtaining a sample from a subject with prostate cancer; 2) detecting expression levels of one or more of NKX3.1, HOXB13, KLK3, PRAC1, PRAC2, MALAT1, HOXC6, AMACR, SCHLAP1, PCAT1, and PCA3 in a sample and determining whether the expression levels of one or more of NKX3.1, HOXB13, KLK3, PRAC1, PRAC2, MALAT1, HOXC6, AMACR, SCHLAP1, PCAT1, and PCA3 are higher or lower compared to expression levels of one or more of NKX3.1, HOXB13, KLK3, PRAC1, PRAC2, MALAT1, HOXC6, AMACR, SCHLAP1, PCAT1, and PCA3 from a reference sample; and 3) diagnosing the subject with a low risk tumor when the expression levels of one or more of NKX3.1, HOXB13, KLK3, PRAC1, PRAC2, MALAT1, HOXC6, AMACR, SCHLAP1, PCAT1, and PCA3 in the sample are lower compared to the expression level of one or more of NKX3.1, HOXB13, KLK3, PRAC1, PRAC2, MALAT1, HOXC6, AMACR, SCHLAP1, PCAT1, and PCA3 from a reference sample.

Disclosed herein are methods of treating low risk tumors in a subject with prostate cancer, the methods comprising: withholding prostatectomy, radiation, chemotherapy, castration, anti-androgen therapy or a combination thereof from the subject with a low risk tumor administering a lower dose of radiation, chemotherapy, anti-androgen therapy or a combination thereof to the subject with a low risk tumor, wherein the subject was diagnosed as having a high risk tumor by: 1) obtaining a sample from a subject with prostate cancer; 2) detecting expression levels of one or more of NKX3.1, HOXB13, KLK3, PRAC1, PRAC2, MALAT1, HOXC6, AMACR, SCHLAP1, PCAT1, and PCA3 in a sample and 3) diagnosing the subject with a low risk tumor when the expression levels of one or more of NKX3.1, HOXB13, KLK3, PRAC1, PRAC2, MALAT1, HOXC6, AMACR, SCHLAP1, PCAT1, and PCA3 in the sample based on the pre-determined pattern of one or more of NKX3.1, HOXB13, KLK3, PRAC1, PRAC2, MALAT1, HOXC6, AMACR, SCHLAP1, PCAT1, and PCA3 in the sample

DETAILED DESCRIPTION

The present disclosure can be understood more readily by reference to the following detailed description of the invention, the figures and the examples included herein.

Before the present methods and gene expression panels are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for cancer, such as, for example, prior to the administering step.

As used herein, the term "comprising" can include the aspects "consisting of" and "consisting essentially of."

As used herein, the term "normal" refers to an individual, a sample or a subject that does not have prostate cancer or does not have an increased susceptibility of developing prostate cancer.

As used herein, the term "susceptibility" refers to the likelihood of a subject being clinically diagnosed with a disease. For example, a human subject with an increased susceptibility for prostate cancer can refer to a human subject with an increased likelihood of a subject being clinically diagnosed with prostate cancer.

As used herein, the term "gene" refers to a region of DNA encoding a functional RNA or protein. "Functional RNA" refers to an RNA molecule that is not translated into a protein. Generally, the gene symbol is indicated by using italicized styling while the protein symbol is indicated by using non-italicized styling.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

By "isolated polypeptide" or "purified polypeptide" is meant a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full-length polypeptides.

By "isolated nucleic acid" or "purified nucleic acid" is meant DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

By "specifically binds" is meant that an antibody recognizes and physically interacts with its cognate antigen and does not significantly recognize and interact with other antigens; such an antibody may be a polyclonal antibody or a monoclonal antibody, which are generated by techniques that are well known in the art.

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for nucleic acids (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the c-Met nucleic acid to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "specifically hybridizes" is meant that a probe, primer, or oligonucleotide recognizes and physically interacts (that is, base-pairs) with a substantially complementary nucleic acid (for example, a c-met nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, N.Y., 1998).

Urine represents an important biospecimen for the development of non-invasive prostate cancer detection methods. Urine-based prostate cancer detection will largely depend on shedding of target cells into urine (Truong M, et al, J Urol. 2013; 189(2):422-9). As such, optimized sampling is important to success. As described herein, the post-DRE single-void, first-catch sampling strategy can be used (Gonzalgo M L, et al., Clin Cancer Res. 2003; 9(7):2673-7; and Rogers C G, et al., J Urol. 2004; 172(4 Pt 1):1501-3). Of importance, informative sampling of this biospecimen can occur in various clinical settings as long as the prostate gland is not removed before sampling. For example, it is clinically feasible to implement post-DRE sampling of urine specimens before prostate biopsy, or before local treatment, including radical prostatectomy (RP) (FIG. 1). Informative sampling before biopsy and before local treatment will allow the development of noninvasive, predictive biomarkers with clinical utility in reducing unnecessary biopsy and overtreatment (FIG. 1).

Urinary detection of prostate cancer cells and prostate cancer markers. Early studies conducted in the pre-PSA era (Albers D D, et al., J Am Med Assoc. 1949; 139(5):299-303; Bologna M, et al., Eur Urol. 1988; 14(6):474-6; Garret M and Jassie M; Acta Cytol. 1976; 20(2):126-31; Koss L G, et al., Acta Cytol. 1985; 29(5):810-6; and Sharifi R, et al., Urology. 1983; 21(4):417-20) established that prostate cancer cells can be detected, at consistently high specificity, by cytologic examination of voided urine from patients with advanced prostate cancer after prostatic massage. Urine cytology as a diagnostic test for prostate cancer, however, suffered from low sensitivity, mainly due to technical difficulty in differentiating the rare malignant cells from other cells in the urine sediment solely on the basis of morphological examination. Alpha-methylacyl-CoA racemase (AMACR) was characterized as a highly sensitive and specific tissue marker for prostate cancer (Luo J, et al., Cancer Res. 2002; 62(8):2220-6). Studies have shown that AMACR-positive prostate cancer cells were visualized by multiplex immunofluorescence cytology of urine sediments from post-DRE urine samples collected before biopsy (Fujita K, et al., Hum Pathol. 2009; 40(7):924-33). In this study, 4 definitively positive, 16 negative, and 5 suspicious cases were identified by immunofluorescence (IF) cytology out of 25 cases diagnosed with prostate cancer (i.e., biopsy positive), and all 8 biopsy-negative cases were negative for urinary AMACR. Therefore, detection sensitivity was 36% (9/25) (counting suspicious cases), and specificity was 100% (8/8) in this small study. These studies were not pursued further due to high background and difficulty in making definitive biomarker calls, as well as the limited number of prostate cancer-specific protein markers suitable for assay development at the time.

Exfoliated prostate cells shed into urine represent possible target cells for developing markers for prostate cancer diagnosis, surveillance, and prognosis. As disclosed herein, prostate cancer cells can be detected and visualized in post-DRE urine specimens, and detection of urinary prostate cancer cells may indicate clinically significant prostate cancer with high specificity.

Described herein are urine RNA markers for prostate cancer. Using advances in RISH technologies, coupled with a rich selection of cancer-specific RNA markers, a robust detection of rare malignant prostate cells in post-DRE urine sediments can be performed. Sample collection including the collection of a total of 313 specimens, processing, and storage were optimized. As also disclosed herein, the majority of these specimens were used to evaluate feasibility, optimize the workflow, and test RISH probes and conditions.

The technology disclosed herein can include one or more of the following: 1) digital rectal examination of the patient suspected of prostate cancer; 2) urine sample collection and processing to permit cellular components that can be deposited onto a planar surface; 3) preparation of cytology slides containing the cellular components suitable for storage; 4) selection of molecular probes for specific detection of cells of prostate origin; 5) selection of molecular probes for specific detection of prostate cancer cells; 6) multiplexing the probes; 7) detection of molecular targets using the probes; 8) image scanning, processing, analysis, and biomarker calls; 9) correlation of biomarker status with biopsy outcome; and 10) correlation of biomarker status with surgical outcome.

Clinical utility of the methods disclosed herein include, but are not limited to: 1) screening of men for prostate cancer detection; 2) indications for the need of biopsy; 3) indication for the need of definitive local treatments; 4) monitoring of men undergoing active surveillance for low-risk prostate cancer; 5) risk stratification and prognosis in men with prostate cancer; 6) justification to forgo invasive diagnostic and monitoring methods, and 7) detection of cancer recurrence in a subset of treated men.

Disclosed herein are urinary RISH assays that can be used as non-invasive methods for prostate cancer detection. Further disclosed herein are methods, assays and processing procedures for cellular analysis of urine specimens. Also, disclosed herein are methods, optimized RISH staining protocols for evaluating cytological specimens. The Examples show that the methods (e.g., multiplex RISH) disclosed herein can be used to successfully identify (and distinguish between) prostate cells and prostate cancer cells in post-DRE urine, demonstrating the ability to detect and visualize cells in clinical specimens using this method.

Disclosed herein are compositions and methods that can be useful in diagnosing an increased susceptibility of prostate cancer in a subject. Disclosed herein, are methods of predicting an outcome of prostate cancer comprising determining the mRNA expression level of one or more, two or more, three or more of NKX3.1, HOXB13, KLK3, PRAC1, PRAC2, MALAT1, HOXC6, AMACR, SCHLAP1, PCAT1, and PCA3 in the sample from a subject. In some aspects, the mRNA expression levels can be detected using RISH. In some aspects, the mRNA expression levels can be detected using RISH with RISH probes under RISH conditions.

Disclosed herein are compositions and methods that can be useful determining whether a patient has prostate cancer cells present in a urine sample. Disclosed herein are compositions and methods that can be useful determining whether a patient has prostate cancer by detecting the mRNA expression of one or more, two or more, three or more of NKX3.1, HOXB13, KLK3, PRAC1, PRAC2, MALAT1, HOXC6, AMACR, SCHLAP1, PCAT1, and PCA3 in in a urine sample from a subject. In some aspects, the mRNA expression levels can be detected using RISH (e.g. chromogenic RISH or fluorescent RISH). In some aspects, the mRNA expression levels can be detected using RISH with RISH probes under RISH conditions.

Disclosed herein are compositions and methods that can be useful to detect clinically significant cancer. In an aspect, the methods disclosed herein can comprise determining at least NKX3.1, PRAC1, and PCA3 expression levels. Currently, patients are placed under an active surveillance or watchful waiting program after an initial diagnosis of low risk or very low risk cancer (which requires a biopsy). The methods disclosed herein, and in particular, detecting at least NKX3.1, PRAC1, and PCA3 in a sample, can be used to detect clinically significant cancer non-invasively (without requiring a biopsy), which can lead to patients being taken out of an active surveillance or watchful waiting program and/or treated upon a prostate cancer diagnosis. Further, the methods disclosed herein can minimize or reduce the risk of a patient or subject being placed in one of these management programs with the possibility of being upgraded to the diagnosis of prostate cancer or the undiagnosed prostate cancer progressing, and losing the treatment window and/or the window of curing the prostate cancer that may also be additionally impacted by another sampling of biopsies.

In sum, the methods disclosed herein can be used to detect prostate cancer and clinically significant prostate cancer in a sample that was missed via a biopsy; and can detect or identify prostate cancer and clinically significant prostate cancer without performing a biopsy.

Risk criteria. Disclosed herein are methods of risk criteria. For example, PSA density can be calculated as PSA (ng/mL) divided by prostate volume (cc) as determined by ultrasound or MRI. Risk status based on D'Amico risk classification (high, low, and intermediate) is disclosed herein (see, for example, D'Amico Av, et al. (1998) Jama, 280(11): 969-974). Briefly, D'Amico risk status can be classified as low, intermediate or high. Low risk indicates subjects with a PSA level that is less than or equal to 10, a Gleason score that is less than or equal to 6, or are in clinical stage T1-2a. Intermediate risk indicates subjects with a PSA level between 10 and 20, a Gleason score of 7, or are in clinical state T2b. High risk indicates subjects with a PSA level of more than 20, a Gleason score equal or larger than 8, or are in clinical stage T2c-3a. Epstein criteria for clinically insignificant prostate cancer: clinical stage T1c, PSA density <0.15 ng/mL/g, absence of Gleason pattern 4 or 5, <3 positive biopsy cores, presence of <50% tumors per core (Epstein J I, et al. (1994) Jama, 271 (5): 368-374). Prostate cancer can be considered "significant" if it does not meet the Epstein criteria described herein. This is important because this criteria can be used to place patients into programs that do not involve definitive treatment. Epstein criteria for clinically insignificant prostate cancer is also the criteria for "very low risk prostate cancer."

Methods for Assessing Susceptibility and/or Diagnosis of Cancer

Disclosed herein, are methods for diagnosing a subject (e.g., human) with an increased susceptibility for prostate cancer. Disclosed herein are methods comprising the steps of, in any order, a) obtaining a urine sample in the subject; b) determining the mRNA expression level of one or more of NKX3.1, HOXB13, KLK3, PRAC1, PRAC2, MALAT1, HOXC6, AMACR, SCHLAP1, PCAT1, and PCA3 in the sample from the subject; c) obtaining a reference mRNA expression level for one or more of NKX3.1, HOXB13, KLK3, PRAC1, PRAC2, MALAT1, HOXC6, AMACR, SCHLAP1, PCAT1, and PCA3 from a normal control; d) comparing the expression level for one or more of NKX3.1, HOXB13, KLK3, PRAC1, PRAC2, MALAT1, HOXC6, AMACR, SCHLAP1, PCAT1, and PCA3 of step b) with the reference expression level for one or more of NKX3.1, HOXB13, KLK3, PRAC1, PRAC2, MALAT1, HOXC6, AMACR, SCHLAP1, PCAT1, and PCA3 of step c); and e) determining that the subject has an increased susceptibility to prostate cancer wherein a ratio of the sample expression level of one or more of NKX3.1, HOXB13, KLK3, PRAC1, PRAC2, MALAT1, HOXC6, AMACR, SCHLAP1, PCAT1, and PCA3 to the reference expression level of one or more of NKX3.1, HOXB13, KLK3, PRAC1, PRAC2, MALAT1, HOXC6, AMACR, SCHLAP1, PCAT1, and PCA3 indicates higher expression level of one or more of NKX3.1, HOXB13, KLK3, PRAC1, PRAC2, MALAT1, HOXC6, AMACR, SCHLAP1, PCAT1, and PCA3 in the sample. In some aspects, the mRNA expression levels can be detected using RISH (e.g. chromogenic RISH or fluorescent RISH). In some aspects, the mRNA expression levels can be detected using RISH with RISH probes under RISH conditions. In an aspect, the mRNA expression level of NKX3.1, PRAC1 and PCA3 can be determined in a sample.

Disclosed herein are methods comprising the steps of, in any order, a) obtaining a urine sample in the subject; b) determining the mRNA expression level of one or more of NKX3.1, HOXB13, KLK3, PRAC1, PRAC2, MALAT1, HOXC6, AMACR, SCHLAP1, PCAT1, and PCA3 in the sample from the subject; c) determining that the subject has an increased susceptibility to prostate cancer based on a pre-determined pattern of one or more of NKX3.1, HOXB13, KLK3, PRAC1, PRAC2, MALAT1, HOXC6, AMACR, SCHLAP1, PCAT1, and PCA3 in the sample. In some aspects, the mRNA expression levels can be detected using RISH (e.g. chromogenic RISH or fluorescent RISH). In some aspects, the mRNA expression levels can be detected using RISH with RISH probes under RISH conditions. In an aspect, the mRNA expression level of NKX3.1, PRAC1 and PCA3 can be determined in a sample.

In some aspects, the methods disclosed herein can be performed without a reference sample. For example, the methods can be performed on a test sample from a subject as disclosed herein. In some aspects, the determination of increased susceptibility to prostate cancer can be based on a pre-determined pattern of one or more of NKX3.1, HOXB13, KLK3, PRAC1, PRAC2, MALAT1, HOXC6, AMACR, SCHLAP1, PCAT1, and PCA. For example, the pre-determined pattern can be a pre-determined signal. In an aspect, the pre-determined pattern can be that one or more of NKX3.1, HOXB13, KLK3, PRAC1, PRAC2, MALAT1, HOXC6, AMACR, SCHLAP1, PCAT1, and PCA can be above a pre-determined threshold. In some aspects, a pre-determined pattern of one or more of NKX3.1, HOXB13, KLK3, PRAC1, PRAC2, MALAT1, HOXC6, AMACR, SCHLAP1, PCAT1, and PCA is not above a pre-determined threshold indicative of no disease or a lack of increased susceptibility to prostate cancer.

In some aspects, the step of determining that the subject has an increased susceptibility to prostate cancer based on a pre-determined pattern of one or more of NKX3.1, HOXB13, KLK3, PRAC1, PRAC2, MALAT1, HOXC6, AMACR, SCHLAP1, PCAT1, and PCA3 in the sample can be automated. In some aspects, the step of determining that the subject has an increased susceptibility to prostate cancer based on a pre-determined pattern of one or more of NKX3.1, HOXB13, KLK3, PRAC1, PRAC2, MALAT1, HOXC6, AMACR, SCHLAP1, PCAT1, and PCA3 in the sample is not automated. In some aspects, the step of determining that the subject has an increased susceptibility to prostate cancer based on a pre-determined pattern of one or more of NKX3.1, HOXB13, KLK3, PRAC1, PRAC2, MALAT1, HOXC6, AMACR, SCHLAP1, PCAT1, and PCA3 in the sample can be performed manually. In some aspects, cells of prostate origin can be identified by the presence of distinct RISH spots for one or more of NKX3.1, HOXB13, KLK3, PRAC1, PRAC2, MALAT1, HOXC6, AMACR, SCHLAP1, PCAT1, for example, either NKX3.1 or PRAC1 in cells with appropriate morphology, and considered prostate cancer cells if they also were positive for PCA3.

In some aspects, the method can further comprise the step of testing the subject with increased susceptibility to prostate cancer to determine if the subject has prostate cancer.

In some aspects, the methods disclosed herein can further comprise classifying the urinary prostate cancer cells as described in the Examples. In some aspects, the methods disclosed herein can comprise a step of patient scoring as described in the Examples. In some aspects, one or more urinary prostate cancer cells can be manually categorized into three class: (1) non-prostate cells, (2) prostate cells, or (3) prostate cancer cells (see, for example, Table 5). For example, criteria for prostate cell positivity can include that at least 5 distinct punctate spots be present in one or more of NKX3.1, HOXB13, KLK3, PRAC1, PRAC2, MALAT1, HOXC6, AMACR, SCHLAP1, PCAT1, and PCA3 channel (for example, in either the PRAC1 or NKX3-1 channel) and have a morphology consistent with cells of prostate origin. Prostate cancer cells can also have the same criteria in addition to containing at least 5 PCA3 spots. In some aspects, cells with less than 5 spots, for example, for 3 markers (PRAC1, NKX3-1 and PCA3) were classified as non-prostate cells. In some aspects, spot thresholds were based on quantification of signals in cultured prostate cells lines spiked into urine specimens. In some aspects, spot thresholds can be pre-determined. In some aspects, positive cells can be manually identified. In some aspects, a tally of positive cells can be recorded by the software during the review process. In some aspects, patients can be scored as 1) prostate cancer positive if at least one (e.g., PCA3) positive cell was detected on the slide; 2) cancer negative/prostate cell positive if at least one (e.g., NKX3-1/PRAC1+PCA3−) cell was detected; 3) cancer negative/prostate cell negative (NKX3-1/PRAC1− and PCA3−) if no prostate cells were detected; or 4) indeterminate if RISH status could not be defined due to obscuring factors or cellular overcrowding.

In some aspects, the method disclosed herein can further comprise administering radiation, chemotherapy, anti-androgen therapy or a combination thereof to the subject or administering a treatment of prostatectomy, radiation, chemotherapy, castration or a combination thereof to the subject with increased susceptibility to prostate cancer. The type of treatment can depend on the prognosis of the subject, the stage of the cancer, or the degree of susceptibility or risk of the identified tumor.

In an aspect, the method further comprises the step of providing a biopsy to the subject. The methods described herein can also be carried out with one or more diagnostic tests (e.g., nucleic acid assay or protein assay. In some aspects, urine cytology can be used as a second diagnostic test. In an aspect, urine cytology can be used with RNA-ISH. In some aspects, the methods disclosed herein can further comprise testing the subject with increased susceptibility to prostate cancer to determine if the subject has an increased risk or susceptibility of developing or having prostate cancer or has prostate cancer. In an aspect, the methods disclosed herein comprise assaying the urine sample to detect the presence of a three or more of NKX3.1, HOXB13, KLK3, PRAC1, PRAC2, MALAT1, HOXC6, AMACR, SCHLAP1, PCAT1, and PCA3, wherein the ratio of the sample expression level of at least one of NKX3.1, HOXB13, KLK3, PRAC1, PRAC2, MALAT1, HOXC6, AMACR, SCHLAP1, PCAT1, and PCA3 to the reference expression of NKX3.1, HOXB13, KLK3, PRAC1, PRAC2, MALAT1, HOXC6, AMACR, SCHLAP1, PCAT1, and PCA3 is two-fold higher indicating an increased susceptibility of prostate cancer in the subject. In some aspects, the methods disclosed herein can be performed without a reference sample. In an aspect, the methods disclosed herein comprise assaying the urine sample to detect the presence of a three or more of NKX3.1, HOXB13, KLK3, PRAC1, PRAC2, MALAT1, HOXC6, AMACR, SCHLAP1, PCAT1, and PCA3 based on a predetermined pattern of one or more of NKX3.1, HOXB13, KLK3, PRAC1, PRAC2, MALAT1, HOXC6, AMACR, SCHLAP1, PCAT1, and PCA. For example, the pre-determined pattern can be a pre-determined signal. In an aspect, the pre-determined pattern can be that one or more of NKX3.1, HOXB13, KLK3, PRAC1, PRAC2, MALAT1, HOXC6, AMACR, SCHLAP1, PCAT1, and PCA can be above a pre-determined threshold. In some aspects, the mRNA expression levels can be detected using RISH (e.g. chromogenic RISH or fluorescent RISH). In some aspects, the mRNA expression levels can be detected using RISH with RISH probes under RISH conditions. In an aspect, the mRNA expression level of NKX3.1, PRAC1 and PCA3 can be determined in a sample.

In some aspects, the methods disclosed herein can further comprise classifying the urinary prostate cancer cells as described in the Examples. In some aspects, the methods disclosed herein can comprise a step of patient scoring as described in the Examples. In some aspects, one or more urinary prostate cells can be manually categorized into three class: (1) non-prostate cells, (2) prostate cells, or (3) prostate cancer cells (see, for example, Table 5). For example, criteria for prostate cell positivity can include that at least 5 distinct punctate spots be present in one or more of NKX3.1, HOXB13, KLK3, PRAC1, PRAC2, MALAT1, HOXC6, AMACR, SCHLAP1, PCAT1, and PCA3 channel (for example, in either the PRAC1 or NKX3-1 channel) and have a morphology consistent with cells of prostate origin. Prostate cancer cells can also have the same criteria in addition to containing at least 5 PCA3 spots. In some aspects, cells with less than 5 spots, for example, for 3 markers (PRAC1, NKX3-1 and PCA3) were classified as non-prostate cells. In some aspects, spot thresholds were based on quantification of signals in cultured prostate cells lines spiked into urine specimens. In some aspects, spot thresholds can be pre-determined. In some aspects, positive cells can be manually identified. In some aspects, a tally of positive cells can be recorded by the software during the review process. In some aspects, patients can be scored as 1) prostate cancer positive if at least one (e.g., PCA3) positive cell was detected on the slide; 2) cancer negative/prostate cell positive if at least one (e.g., NKX3-1/PRAC1+PCA3−) cell was detected; 3) cancer negative/prostate cell negative (NKX3-1/PRAC1− and PCA3−) if no prostate cells were detected; or 4) indeterminate if RISH status could not be defined due to obscuring factors or cellular overcrowding.

PCA3 is a non-coding RNA specific to prostate gland that is overexpressed in prostate cancer. It is associated with prostate cancer cells, but not non-cancer prostate cells or normal cells. PRAC1 encodes for a small nuclear protein that is highly expressed in the prostate. It is associated with prostate cells and prostate cancer cells but is not associated with normal cells. NKX3-1 encodes for transcription factor that is highly expressed in prostate cells. It is associated with prostate cells and prostate cancer cells but is not associated with normal cells.

Obtaining a tissue sample. Procedures for the collection of a sample of a subject's urine can be done by methods known in the art.

Determining mRNA expression level. As used herein, the term "expression," when used in the context of determining or detecting the expression or expression level of one or more genes, can refer to determining or detecting transcription of the gene (i.e., determining mRNA levels) and/or determining or detecting translation of the gene (e.g., determining or detecting the protein produced). To determine the expression level of a gene means to determine whether or not a gene is expressed, and if expressed, to what relative degree.

RNA in situ hybridization (RISH) can use labeled complementary RNA or modified nucleic acid strand (i.e., probe) to localize a specific RNA sequence in a portion of a tissue or cell. In situ hybridization techniques include, for example: in situ hybridization to mRNA with oligonucleotide and RNA probes (both radio-labelled and hapten-labelled); analysis with light and electron microscopes; whole mount in situ hybridization; double detection of RNAs and RNA plus protein; and fluorescent in situ hybridization to detect chromosomal sequences. Fluorescent DNA ISH (FISH) can, for example, be used in medical diagnostics to assess chromosomal integrity. RNA ISH (RNA in situ hybridization) is used to measure and localize RNAs (mRNAs, lncRNAs, and miRNAs) within tissue sections, cells, whole mounts, and circulating tumor cells (CTCs).

In general, the process for hybridization histochemistry, samples (e.g., cells and tissues) are usually treated to fix the target transcripts in place and to increase access of the probe. The probe can be a labeled complementary DNA or a complementary RNA serving as a probe. The probe can hybridize to the target sequence, for instance, at an elevated temperature, and then the excess probe can be washed away (after prior hydrolysis using RNase in the case of unhybridized, excess RNA probe). Solution parameters such as temperature, salt, and/or detergent concentration can be manipulated to remove any non-identical interactions (i.e., only exact sequence matches will remain bound). Then, the probe that was labeled with either radio-, fluorescent- or antigen-labeled bases (e.g., digoxigenin) can be localized and quantified in the tissue using either autoradiography, fluorescence microscopy or immunohistochemistry, respectively. ISH can also use two or more probes, labeled with radioactivity or the other non-radioactive labels, to simultaneously detect two or more transcripts. In an aspect, RISH methods as disclosed herein can use at least three probes.

In some aspects, the expression level of one or more genes or RNA disclosed herein can be determined directly (e.g., immunoassays, mass spectrometry) or indirectly (e.g., determining the mRNA expression of a protein or peptide). In some aspects, the expression level of one or more genes or RNA disclosed herein can be determined directly (e.g., immunoassays, mass spectrometry) or indirectly (e.g., determining the mRNA expression of a protein or peptide) in parallel or in combination with RISH. Examples of mass spectrometry include ionization sources such as EI, CI, MALDI, ESI, and analysis such as Quad, ion trap, TOF, FT or combinations thereof, spectrometry, isotope ratio mass spectrometry (IRMS), thermal ionisation mass spectrometry (TIMS), spark source mass spectrometry, Multiple Reaction Monitoring (MRM) or SRM. Any of these techniques can be carried out in combination with prefractionation or enrichment methods. Examples of immunoassays include immunoblots, Western blots, Enzyme linked Immunosorbant Assay (ELISA), Enzyme immunoassay (EIA), radioimmune assay. Immunoassay methods use antibodies for detection and determination of levels of an antigen are known in the art. The antibody can be immobilized on a solid support such as a stick, plate, bead, microbead or array.

Expression levels of one or more of the genes described herein can be also be determined indirectly by determining the mRNA expression for the one or more genes in a sample. RNA expression methods include but are not limited to RISH, extraction of cellular mRNA and Northern blotting using labeled probes that hybridize to transcripts encoding all or part of the gene, amplification of mRNA using gene-specific primers, polymerase chain reaction (PCR), and reverse transcriptase-polymerase chain reaction (RT-PCR), followed by quantitative detection of the gene product by a variety of methods; extraction of RNA from cells, followed by labeling, and then used to probe cDNA or olignonucleotides encoding the gene, in situ hybridization; and detection of a reporter gene.

Methods to measure protein expression levels include but are not limited to Western blot, immunoblot, ELISA, radio-immunoassay, immunoprecipitation, surface plasmon resonance, chemiluminescence, fluorescent polarization, phosphorescence, immunohistochemical analysis, microcytometry, microarray, microscopy, fluorescence activated cell sorting (FACS), and flow cytometry. The method can also include specific protein property-based assays based including but not limited to enzymatic activity or interaction with other protein partners. Binding assays can also be used, and are well known in the art. For instance, a BIAcore machine can be used to determine the binding constant of a complex between two proteins. Other suitable assays for determining or detecting the binding of one protein to another include, immunoassays, such as ELISA and radioimmunoassays. Determining binding by monitoring the change in the spectroscopic can be used or optical properties of the proteins can be determined via fluorescence, UV absorption, circular dichroism, or nuclear magnetic resonance (NMR). Alternatively, immunoassays using specific antibody can be used to detect the expression on of a particular protein on a tumor cell.

Reference mRNA expression level. As used herein, the term "reference," "reference expression," "reference sample," "reference value," "control," "control sample" and the like, when used in the context of a sample or expression level of one or more genes or proteins refers to a reference standard wherein the reference is expressed at a constant level, and is unaffected by the experimental conditions, and is indicative of the level in a sample of a predetermined disease status (e.g., not suffering from prostate cancer). The reference value can be a predetermined standard value or a range of predetermined standard values, representing no illness, or a predetermined type or severity of illness.

Reference expression can be the level of the one or more genes described herein in a reference sample from a subject, or a pool of subjects, not suffering from prostate cancer or from a predetermined severity or type of prostate cancer. In an aspect, the reference value is the level of one or more genes disclosed herein in the sample of a subject, or subjects, wherein the subject or subjects is not suffering from prostate cancer.

Comparing the expression level of one or more genes disclosed herein. In some aspects comparing the expression level for one or more of, for example, NKX3.1, HOXB13, KLK3, PRAC1, PRAC2, MALAT1, HOXC6, AMACR, SCHLAP1, PCAT1, and PCA3 of step b) with the reference expression level for, for example, NKX3.1, HOXB13, KLK3, PRAC1, PRAC2, MALAT1, HOXC6, AMACR, SCHLAP1, PCAT1, and PCA3 of step c), can be performed to determine a subject's susceptibility to prostate cancer and whether the subject has prostate cancer. In an aspect, the mRNA expression level of one or more of NKX3.1, PRAC1 and PCA3 or a combination thereof can be determined.

Determining the expression level of one or more genes disclosed herein can include determining whether the gene is upregulated or increased as compared to a control or reference sample, downregulated or decreased compared to a control or reference sample, or unchanged compared to a control or reference sample. As used herein, the terms, "upregulated" and "increased expression level" or "increased level of expression" refers to a sequence corresponding to one or more genes disclosed herein that is expressed wherein the measure of the quantity of the sequence exhibits an increased level of expression when compared to a reference sample or "normal" control. For example, the terms, "upregulated" and "increased expression level" or "increased level of expression" refers to a sequence corresponding to one or more genes disclosed herein that is expressed wherein the measure of the quantity of the sequence exhibits an increased level of expression of one or more of NKX3.1, HOXB13, KLK3, PRAC1, PRAC2, MALAT1, HOXC6, AMACR, SCHLAP1, PCAT1, and PCA3 protein(s) and/or mRNA when compared to the expression of the same mRNA(s) from a reference sample or "normal" control. An "increased expression level" refers to an increase in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more. As used herein, the terms "downregulated," "decreased level of expression," or "decreased expression level" refers to a sequence corresponding to one or more genes disclosed herein that is expressed wherein the measure of the quantity of the sequence exhibits a decreased level of expression when compared to a reference sample or "normal" control For example, the terms "downregulated,"

"decreased level of expression," or "decreased expression level" refers to a sequence corresponding to one or more genes disclosed herein that is expressed wherein the measure of the quantity of the sequence exhibits a decreased level of expression of one or more of NKX3.1, HOXB13, KLK3, PRAC1, PRAC2, MALAT1, HOXC6, AMACR, SCHLAP1, PCAT1, and PCA3 protein(s) and/or mRNA when compared to the expression of the same mRNA(s) from a reference sample or "normal" control. A "decreased level of expression" refers to a decrease in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more. In an aspect, expression level of one or more of NKX3.1, PRAC1 or PCA3 proteins or a combination thereof can be determined in a sample.

Determining an increased susceptibility to prostate cancer. As described herein, samples from a subject can be compared with reference samples to determine the expression ratio to determine whether a subject has an increased susceptibility to prostate cancer. The reference samples can be from subjects having "normal" levels of one or more of the following genes, NKX3.1, HOXB13, KLK3, PRAC1, PRAC2, MALAT1, HOXC6, AMACR, SCHLAP1, PCAT1, and PCA3. Suitable statistical and other analysis can be carried out to confirm a change (e.g., an increase or a higher level of expression) in one or more of NKX3.1, HOXB13, KLK3, PRAC1, PRAC2, MALAT1, HOXC6, AMACR, SCHLAP1, PCAT1, and PCA3 when compared with a reference sample, wherein a ratio of the sample expression level of one or more of NKX3.1, HOXB13, KLK3, PRAC1, PRAC2, MALAT1, HOXC6, AMACR, SCHLAP1, PCAT1, and PCA3 to the reference expression level of one or more of NKX3.1, HOXB13, KLK3, PRAC1, PRAC2, MALAT1, HOXC6, AMACR, SCHLAP1, PCAT1, and PCA3 indicates higher expression level of one or more of NKX3.1, HOXB13, KLK3, PRAC1, PRAC2, MALAT1, HOXC6, AMACR, SCHLAP1, PCAT1, and PCA3 in the sample. In an aspect, the ratio of the sample expression level of two or more, three or more, four or more, five or more, or six or more of NKX3.1, HOXB13, KLK3, PRAC1, PRAC2, MALAT1, HOXC6, AMACR, SCHLAP1, PCAT1, and PCA3 to the reference expression level of two or more, three or more, four or more, five or more, or six or more of NKX3.1, HOXB13, KLK3, PRAC1, PRAC2, MALAT1, HOXC6, AMACR, SCHLAP1, PCAT1, and PCA3 indicates higher expression level of two or more, three or more, four or more, five or more, or six or more of NKX3.1, HOXB13, KLK3, PRAC1, PRAC2, MALAT1, HOXC6, AMACR, SCHLAP1, PCAT1, and PCA3 in the sample, indicating that the subject has an increased susceptibility to prostate cancer. In an aspect, the mRNA expression level of NKX3.1, PRAC1 and/or PCA3 or a combination thereof can be determined in a sample.

A higher or increased expression level of one or more of NKX3.1, HOXB13, KLK3, PRAC1, PRAC2, MALAT1, HOXC6, AMACR, SCHLAP1, PCAT1, and PCA3 when compared to the reference expression level of NKX3.1, HOXB13, KLK3, PRAC1, PRAC2, MALAT1, HOXC6, AMACR, SCHLAP1, PCAT1, and PCA3 can indicate an increased susceptibility to prostate cancer or that a subject has prostate cancer. Signature pattern(s) of increased (higher) or decreased (lower) sample expression levels of one or more of NKX3.1, HOXB13, KLK3, PRAC1, PRAC2, MALAT1, HOXC6, AMACR, SCHLAP1, PCAT1, and PCA3 when compared to the reference expression levels of one or more of NKX3.1, HOXB13, KLK3, PRAC1, PRAC2, MALAT1, HOXC6, AMACR, SCHLAP1, PCAT1, and PCA3 can be observed and indicate the susceptibility (e.g., higher or lower) or the presence or absence of prostate cancer (or prostate cancer cells) in a subject. In an aspect, the a subject's expression levels can comprise a combination of increased and decreased (or no change) expression levels of one or more of NKX3.1, HOXB13, KLK3, PRAC1, PRAC2, MALAT1, HOXC6, AMACR, SCHLAP1, PCAT1, and PCA3 when compared to the reference expression levels of one or more of NKX3.1, HOXB13, KLK3, PRAC1, PRAC2, MALAT1, HOXC6, AMACR, SCHLAP1, PCAT1, and PCA3 and such expression levels can indicate the susceptibility (e.g., higher or lower) or the presence or absence of prostate cancer (or prostate cancer cells) in a subject.

In some aspects, the expression level of one or more of NKX3.1, HOXB13, KLK3, PRAC1, PRAC2, MALAT1, HOXC6, AMACR, SCHLAP1, PCAT1, and PCA3 can be determined without a reference sample. In some aspects, the expression level of one or more of NKX3.1, HOXB13, KLK3, PRAC1, PRAC2, MALAT1, HOXC6, AMACR, SCHLAP1, PCAT1, and PCA3 can be determined based on a pre-determined pattern of one or more of NKX3.1, HOXB13, KLK3, PRAC1, PRAC2, MALAT1, HOXC6, AMACR, SCHLAP1, PCAT1, and PCA3 in the sample. In some aspects, such determination can be performed via computer-implemented software. In some aspects, such determination can be automated. In some aspects, such determination can be performed manually.

Figure 16:
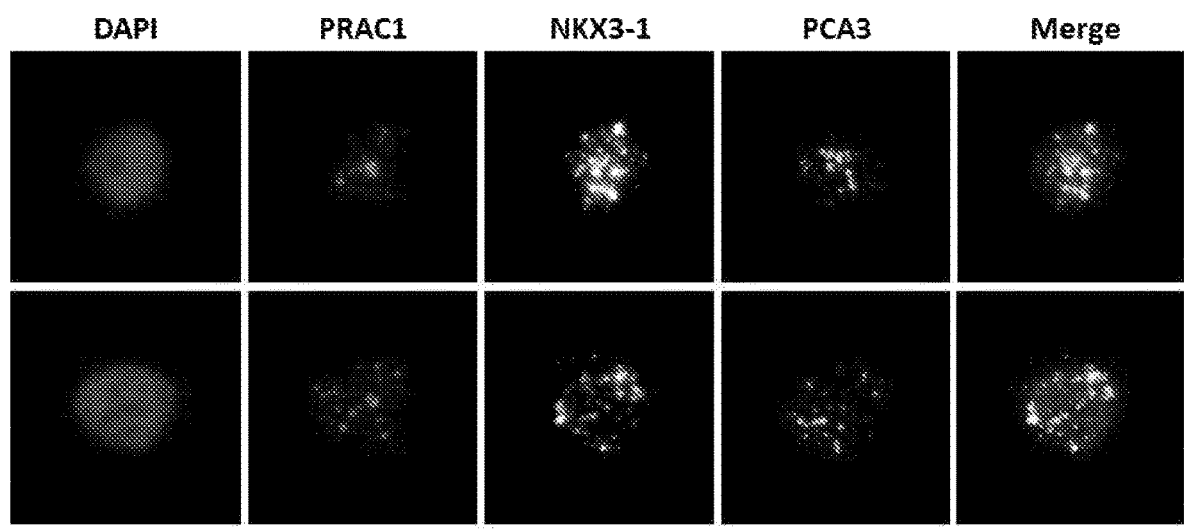
FIG. 16 shows representative images of prostate cancer cells detected in post-DRE urine sediments by multiplex RISH for PRAC1 (red), NKX3-1 (white), and PCA3 (green); cells counterstained with DAPI.

Examples of signature patterns and expression levels of one or more of NKX3.1, HOXB13, KLK3, PRAC1, PRAC2, MALAT1, HOXC6, AMACR, SCHLAP1, PCAT1, and PCA3 are disclosed in the Examples and figures. For example, FIG. 16 shows that prostate cancer cells are positive for NKX3.1, PRAC1 and PCA3. In an aspect, a subject's expression levels of NKX3.1, PRAC1 and PCA3 can be increased or show a pre-determined signal or be above a pre-determined threshold; and said expression levels can indicate an increased susceptibility or a risk level of prostate cancer in said subject. In some aspects, said signature pattern indicates and/or correlates with clinically significant cancer.

In some aspects, NKX3.1 and PRAC1 are also expressed in normal or non-cancerous prostate cancer, and shed into the urine without the detection of PCA3; thus indicating an increased risk or susceptibility of prostate cancer. The data provided herein shows that when PCA3 is also detected in the urine, the cells are almost always positive for both NKX3.1 and PRAC1, thus indicating the detection of cancer cells. Further, the data disclosed herein also shows that when cancer cells are detected that they are almost always clinically significant for prostate cancer. The clinical importance of such a finding is that these patients will not be placed or can be removed from risk management programs such as active surveillance or watchful waiting, but would rather be placed in an a treatment program with an increased chance of a cure.

The expression level of one or more genes described herein can be a measure of one or more genes (e.g. DNA, RNA or mRNA), for example, per unit weight or volume. In an aspect, the expression level can be a ratio (e.g., the amount of one or more genes in a sample relative to the amount of the one or more markers of a reference value). In an aspect, the expression level can be based on a pre-determined pattern of one or more of NKX3.1, HOXB13, KLK3, PRAC1, PRAC2, MALAT1, HOXC6, AMACR, SCHLAP1, PCAT1, and PCA. For example, the pre-determined pattern can be a pre-determined signal. In an aspect, the pre-determined pattern can be that one or more of NKX3.1, HOXB13, KLK3, PRAC1, PRAC2, MALAT1, HOXC6, AMACR, SCHLAP1, PCAT1, and PCA can be above a pre-determined threshold. In some aspects, a pre-determined pattern of one or more of NKX3.1, HOXB13, KLK3, PRAC1, PRAC2, MALAT1, HOXC6, AMACR, SCHLAP1, PCAT1, and PCA is not above a pre-determined threshold indicative of no disease or a lack of increased susceptibility to prostate cancer or indicate a specified risk level.

In some aspects, samples from a subject can be compared with reference samples to determine the percent change to determine whether a subject has an increased susceptibility to prostate cancer. In other words, the expression level can be expressed as a percent. For example, the percent change in the expression levels of one or more genes, wherein the expression level of one (or two, three, four, five or six) or more of NKX3.1, HOXB13, KLK3, PRAC1, PRAC2, MALAT1, HOXC6, AMACR, SCHLAP1, PCAT1, and PCA3 is increased (or is higher) by 10%, 15%, 20%, 25%, 30%, 35%, 40%, 45%, 50%, 55%, 60%, 65%, 70%, 75%, 80%, 85%, 90%, 95%, or 100% when compared to the reference expression level of NKX3.1, HOXB13, KLK3, PRAC1, PRAC2, MALAT1, HOXC6, AMACR, SCHLAP1, PCAT1, and PCA3, indicating an increased susceptibility to prostate cancer. Alternatively, the percent change in the expression levels of one or more genes can be decreased (or lower) by 10%, 15%, 20%, 25%, 30%, 35%, 40%, 45%, 50%, 55%, 60%, 65%, 70%, 75%, 80%, 85%, 90%, 95%, or 100% when compared to a reference expression level.

In some aspects, an increase or decrease or some combination thereof in the expression level of genes or proteins other than those disclosed herein can indicate an increased susceptibility for prostate cancer or a diagnosis of prostate cancer in a subject. In some aspects, a signature pattern of increased or decreased expression levels of one or more of the genes or proteins disclosed herein is indicative.

In aspect, the methods disclosed herein can further include a method of prevention of prostate cancer morbidity and/or mortality. For example, the method comprises providing to a subject, further testing (which can include testing for cancer), such as, for example, a biopsy, and/or a routine physical examination, wherein an increased susceptibility to prostate cancer has been diagnosed. The method can further include the administration of therapy to prevent prostate cancer from developing or spreading, thereby reducing prostate cancer morbidity and/or mortality.

The methods described herein can further comprise the step of assaying the prostate tissue sample from the subject to detect the presence of other molecular features of prostate cancer. In an aspect, wherein other molecular features of prostate cancer is detected in the sample, the ratio (or percent change) of the sample expression level of at least one of NKX3.1, HOXB13, KLK3, PRAC1, PRAC2, MALAT1, HOXC6, AMACR, SCHLAP1, PCAT1, and PCA3 to reference expression of the same gene is two-fold higher (or more) indicating an increased susceptibility of prostate cancer in the subject.

Diagnostic Device

Disclosed herein, is a diagnostic device for diagnosing or assessing the risk of developing prostate cancer in a subject (e.g., human). In an aspect, a urine sample can be obtained from the subject and the level or expression level in the sample can be compared with a reference value.

The diagnostic device can include one or more biomarkers. Biomarkers can bind to or hybridize with one or more genes disclosed herein, RNA products or peptides. As used herein, the terms "marker" or "biomarker" refers to detectable or measurable substance (e.g., gene, gene product, protein, etc.) in a sample that can indicate a biological state, disease, condition, predict a clinical outcome, etc. In an aspect, the biomarkers can be NKX3.1, HOXB13, KLK3, PRAC1, PRAC2, MALAT1, HOXC6, AMACR, SCHLAP1, PCAT1, and PCA3 or NKX3.1, HOXB13, KLK3, PRAC1, PRAC2, MALAT1, HOXC6, AMACR, SCHLAP1, PCAT1, and PCA3 or a fragment thereof, or an antibody or fragment thereof which binds one or more of the biomarkers. The diagnostic device can be incorporated into a kit for diagnosing or assessing the risk of developing prostate cancer in a subject.

Disclosed herein are methods of detecting two or more nucleic acids of interest. The method can comprise providing a sample comprising or suspected of comprising the two or more nucleic acids of interest. The method can comprise capturing the nucleic acids of interest present in the sample on a solid support, wherein the solid support comprises a plurality of capture probes, and wherein first and second nucleic acids of interest are captured on the solid support by hybridizing two or more capture extenders to each of the first and second nucleic acids and to two or more of the capture probes. The method can comprise detecting the presence or absence of the two or more label probe systems on the solid support.

In Situ Hybridization Assay

Disclosed herein are methods for detection of target RNA with intact cell. In an aspect, cells can be fixed onto slides and treated to permeabilize the cells. One or more independent probes (e.g., double Z probes) can be designed to hybridize to the target sequence in tandem for signal amplification to take place. The design of the probes can be such that selective amplification to target-specific signals occurs. The target Z probe can comprise three elements: a lower region, a spacer and a upper region. For example, the lower region of the Z probe can be an 18 to 25 base region that can be complementary to the target RNA. This sequence can be selected because it is target specific. A spacer sequence is a sequence that links the two components of the probe (e.g., the lower region to the upper region). The upper region of the Z probe can be a 14-base tail sequence. The two tails from a double Z probe pair can form a 28 base binding site for the pre-amplifier.

Double Z target probes can hybridize to the target RNA. Pre-amplifiers can hybridize to the 28-base binding site formed by each double Z probe. Amplifiers can bind to the multiple binding sites present on each preamplifer. Labeled probes can contain a fluorescent molecule or chromogenic enzyme that can bind to the binding sites present on each amplifier.

In an aspect, the detection of each RNA molecule can include three double Z probes to bind to the RNA target.

Kits

In an aspect, kits are provided for measuring the RNA (e.g., a RNA product) of one or more biomarkers disclosed herein. The kits can comprise materials and reagents that can be used for measuring the expression of the RNA of one or more biomarkers. Examples of suitable kits include double Z probes or microarray. These kits can include the reagents needed to carry out the measurements of the RNA expression levels. Alternatively, the kits can further comprise additional materials and reagents. For example, the kits can comprise materials and reagents required to measure RNA expression levels of any number of genes up to 1, 2, 3, 4, 5, 10, or more genes that are not biomarkers disclosed herein.

Gene Expression Panel

Disclosed herein are gene expression panels and arrays for assessing risk of developing prostate cancer in a subject (e.g., human) consisting of primers or probes capable of detecting or amplifying one or more genes disclosed herein. The disclosed gene expression panels or arrays can comprise any of the genes disclosed herein, primers or probes that can hybridize to one or more of the genes or portions of said genes described herein. For example, the gene expression panel or array can be used to detect one or more of NKX3.1, HOXB13, KLK3, PRAC1, PRAC2, MALAT1, HOXC6, AMACR, SCHLAP1, PCAT1, and PCA3. In an aspect, the gene expression panels or arrays can comprise NKX3.1, HOXB13, KLK3, PRAC1, PRAC2, MALAT1, HOXC6, AMACR, SCHLAP1, PCAT1, and PCA, primers or probes that can hybridize to one or more of the genes or portions of said genes described herein. In an aspect, the sample can be urine. In an aspect, the gene expression panels or arrays can comprise NKX3.1, PRAC1, or PCA3 or a combination thereof. The gene expression panels or arrays disclosed herein can consist of primers or probes capable of detecting or amplifying any number of the genes disclosed herein. The gene expression panels or arrays disclosed herein can further comprise primers or probes capable of detecting or amplifying any number of genes not disclosed herein. For example, the primers or probes can detect or amplify between 1 and 5, 5 and 10, 10 and 100, or more, or any variation in between.

The gene expression panels or arrays disclosed herein can be used as a standalone method for assessing risk of developing prostate cancer in a subject or in combination with one or more other gene expression panels or arrays not disclosed herein. They can be used along with one or more diagnostic test. In an aspect, the gene expression panels or arrays can further comprise a second diagnostic test. The gene expression panels or arrays disclosed herein can also be used in the methods disclosed herein to generate a specific profile. In some aspects, the second diagnostic test can be urine cytology. In some aspects, the profile can be provided in the form of a heatmap or boxplot.

The profile of the gene expression levels can be used to compute a statistically significant value based on differential expression of the one or more genes disclosed herein, wherein the computed value correlates to a diagnosis for prostate cancer. The variance in the obtained profile of expression levels of the said selected genes or gene expression products can be either upregulated or downregulated in subjects with an increased susceptibility compared to a reference subject or control. For example, when the expression level of one or more of NKX3.1, HOXB13, KLK3, PRAC1, PRAC2, MALAT1, HOXC6, AMACR, SCHLAP1, PCAT1, and PCA3 are upregulated, indicating an increased risk of developing prostate cancer. In some aspects, the expression level of the said selected genes or gene expression products can be performed without comparing to a reference subject, sample or control. The Examples section provides additional detail. As described herein, one of ordinary skill in the art can use a combination of any of genes disclosed herein to form a profile that can then be used to assess risk of developing prostate cancer, or to determine (and diagnose) whether a subject has prostate cancer.

Disclosed herein are methods of diagnosing prostate cancer using the gene expression panel or array as described herein. In an aspect, the method further comprises performing a biopsy.

In an aspect, the gene expression panel or array disclosed herein can be used to determine or assess the risk of developing prostate cancer in a subject, wherein the expression level for NKX3.1, HOXB13, KLK3, PRAC1, PRAC2, MALAT1, HOXC6, AMACR, SCHLAP1, PCAT1, and PCA3 in the sample is compared to a reference expression level for NKX3.1, HOXB13, KLK3, PRAC1, PRAC2, MALAT1, HOXC6, AMACR, SCHLAP1, PCAT1, and PCA3. In an aspect, the gene expression panel or array disclosed herein can be used to determine or assess the risk of developing prostate cancer in a subject, wherein a ratio (or percent change) of the sample expression level of one or more of NKX3.1, HOXB13, KLK3, PRAC1, PRAC2, MALAT1, HOXC6, AMACR, SCHLAP1, PCAT1, and PCA3 to the reference expression level of one or more of NKX3.1, HOXB13, KLK3, PRAC1, PRAC2, MALAT1, HOXC6, AMACR, SCHLAP1, PCAT1, and PCA3 indicates higher expression level of one or more of NKX3.1, HOXB13, KLK3, PRAC1, PRAC2, MALAT1, HOXC6, AMACR, SCHLAP1, PCAT1, and PCA3 in the sample. In an aspect, the ratio (or percent change) of the sample expression level of two or more, three or more, four or more, five or more, or six or more of NKX3.1, HOXB13, KLK3, PRAC1, PRAC2, MALAT1, HOXC6, AMACR, SCHLAP1, PCAT1, and PCA3 to the reference expression level of two or more, three or more, four or more, five or more, or six or more of NKX3.1, HOXB13, KLK3, PRAC1, PRAC2, MALAT1, HOXC6, AMACR, SCHLAP1, PCAT1, and PCA3 indicates higher expression level of two or more, three or more, four or more, five or more, or six or more of NKX3.1, HOXB13, KLK3, PRAC1, PRAC2, MALAT1, HOXC6, AMACR, SCHLAP1, PCAT1, and PCA3 in the sample, indicating that the subject has an increased susceptibility to prostate cancer. Suitable statistical and other analysis can be carried out to confirm a change (e.g., an increase or a higher level of expression) in one or more of NKX3.1, HOXB13, KLK3, PRAC1, PRAC2, MALAT1, HOXC6, AMACR, SCHLAP1, PCAT1, and PCA3 when compared with a reference sample. In an aspect, the gene expression panels or arrays can comprise NKX3.1, PRAC1, or PCA3 or a combination thereof. In an aspect, the ratio of NKX3.1, PRAC1, or PCA3 or a combination thereof can be compared to the reference expression level of NKX3.1, PRAC1, or PCA3 or a combination thereof.

In some aspects, the methods disclosed herein can be performed without a reference sample. For example, the methods can be performed on a test sample from a subject as disclosed herein. In some aspects, the determination of increased susceptibility to prostate cancer can be based on a pre-determined pattern of one or more of NKX3.1, HOXB13, KLK3, PRAC1, PRAC2, MALAT1, HOXC6, AMACR, SCHLAP1, PCAT1, and PCA. For example, the pre-determined pattern can be a pre-determined signal. In an aspect, the pre-determined pattern can be that one or more of NKX3.1, HOXB13, KLK3, PRAC1, PRAC2, MALAT1, HOXC6, AMACR, SCHLAP1, PCAT1, and PCA can be above a pre-determined threshold. In some aspects, a pre-determined pattern of one or more of NKX3.1, HOXB13, KLK3, PRAC1, PRAC2, MALAT1, HOXC6, AMACR, SCHLAP1, PCAT1, and PCA is not above a pre-determined threshold indicative of no disease or a lack of increased susceptibility to prostate cancer.

In some aspects, the step of a subject's risk of developing prostate cancer can be based on a pre-determined pattern of one or more of NKX3.1, HOXB13, KLK3, PRAC1, PRAC2, MALAT1, HOXC6, AMACR, SCHLAP1, PCAT1, and PCA3 in the sample can be automated. In some aspects, the step of determining subject's risk of developing prostate cancer based on a pre-determined pattern of one or more of NKX3.1, HOXB13, KLK3, PRAC1, PRAC2, MALAT1, HOXC6, AMACR, SCHLAP1, PCAT1, and PCA3 in the sample is not automated. In some aspects, the step of determining that subject's risk of developing prostate cancer based on a pre-determined pattern of one or more of NKX3.1, HOXB13, KLK3, PRAC1, PRAC2, MALAT1, HOXC6, AMACR, SCHLAP1, PCAT1, and PCA3 in the sample can be performed manually. In some aspects, cells of prostate origin can be identified by the presence of distinct RISH spots for one or more of NKX3.1, HOXB13, KLK3, PRAC1, PRAC2, MALAT1, HOXC6, AMACR, SCHLAP1, PCAT1, for example, either NKX3.1 or PRAC1 in cells with appropriate morphology, and considered prostate cancer cells if they also were positive for PCA3.

In some aspects, the methods disclosed herein can further comprise classifying the urinary prostate cancer cells as described in the Examples. In some aspects, the methods disclosed herein can comprise a step of patient scoring as described in the Examples. In some aspects, one or more urinary prostate cells can be manually categorized into three class: (1) non-prostate cells, (2) prostate cells, or (3) prostate cancer cells (see, for example, Table 5). For example, criteria for prostate cell positivity can include that at least 5 distinct punctate spots be present in one or more of NKX3.1, HOXB13, KLK3, PRAC1, PRAC2, MALAT1, HOXC6, AMACR, SCHLAP1, PCAT1, and PCA3 channel (for example, in either the PRAC1 or NKX3-1 channel) and have a morphology consistent with cells of prostate origin. Prostate cancer cells can also have the same criteria in addition to containing at least 5 PCA3 spots. In some aspects, cells with less than 5 spots, for example, for 3 markers (PRAC1, NKX3-1 and PCA3) were classified as non-prostate cells. In some aspects, spot thresholds were based on quantification of signals in cultured prostate cells lines spiked into urine specimens. In some aspects, spot thresholds can be pre-determined. In some aspects, positive cells can be manually identified. In some aspects, a tally of positive cells can be recorded by the software during the review process. In some aspects, patients can be scored as 1) prostate cancer positive if at least one (e.g., PCA3) positive cell was detected on the slide; 2) cancer negative/prostate cell positive if at least one (e.g., NKX3-1/PRAC1+PCA3−) cell was detected; 3) cancer negative/prostate cell negative (NKX3-1/PRAC1− and PCA3−) if no prostate cells were detected; or 4) indeterminate if RISH status could not be defined due to obscuring factors or cellular overcrowding.

The gene expression panel or array can consist of primers or probes capable of detecting, amplifying or otherwise measuring the presence or expression of one or more genes disclosed herein. In an aspect, the gene expression panel or array disclosed herein for can be used to determine or assess the risk of developing prostate cancer in a subject, wherein NKX3.1, HOXB13, KLK3, PRAC1, PRAC2, MALAT1, HOXC6, AMACR, SCHLAP1, PCAT1, and PCA3 RNA expression levels are detected in the sample. In an aspect, the gene expression panels or arrays can comprise NKX3.1, PRAC1, or PCA3 or a combination thereof.

In an aspect, a diagnostics kit is disclosed comprising one or more probes or primers capable of detecting, amplifying or measuring the presence or expression of one or more genes disclosed herein.

Disclosed herein, are solid supports comprising one or more primers, probes, polypeptides, or antibodies capable of hybridizing or binding to one or more of the genes disclosed herein. Solid supports are solid state substrates or supports that molecules, such as analytes and analyte binding molecules, can be associated. Analytes (e.g., calcifying nanoparticles and proteins) can be associated with solid supports directly or indirectly. For example, analytes can be directly immobilized on solid supports. Analyte capture agents (e.g., capture compounds) can also be immobilized on solid supports.

An array is a form of solid support. An array detector is also a form of solid support to which multiple different capture compounds or detection compounds have been coupled in an array, grid, or other organized pattern.

Solid-state substrates for use in solid supports can include, for instance, any solid material to which molecules can be coupled. Examples of such materials include acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, poly lactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or any combination thereof. Solid-state substrates and solid supports can be porous or non-porous. An example of a solid-state substrate is a microtiter dish (e.g., a standard 96-well type). A multiwell glass slide can also be used. For example, such as one containing one array per well can be used, allowing for greater control of assay reproducibility, increased throughput and sample handling, and ease of automation.

Different compounds can be used together as a set. The set can be used as a mixture of all or subsets of the compounds used separately in separate reactions, or immobilized in an array. Compounds used separately or as mixtures can be physically separable through, for example, association with or immobilization on a solid support. An array can include a plurality of compounds immobilized at identified or predefined locations on the array. Each predefined location on the array can generally have one type of component (that is, all the components at that location are the same). Each location can have multiple copies of the component. The spatial separation of different components in the array allows separate detection and identification of the polynucleotides or polypeptides disclosed herein.

It is not required that a given array be a single unit or structure. The set of compounds can be distributed over any number of solid supports. For example, each compound can be immobilized in a separate reaction tube or container, or on separate beads or microparticles. Different aspects of the disclosed method and use of the gene expression panel or array or diagnostic device can be performed with different components (e.g., different compounds specific for different proteins) immobilized on a solid support.

Some solid supports can have capture compounds, such as antibodies, attached to a solid-state substrate. Such capture compounds can be specific for calcifying nanoparticles or a protein on calcifying nanoparticles. Captured calcified nanoparticles or proteins can then be detected by binding of a second detection compound, such as an antibody. The detection compound can be specific for the same or a different protein on the calcifying nanoparticle.

Methods for immobilizing nucleic acids, peptides or antibodies (and other proteins) to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidinbiotin, photocrosslinkable agents, epoxides, maleimides and N-[y-Maleimidobutyryloxy] succinimide ester (GMBS), and a heterobifunctional crosslinker. Antibodies can be attached to a substrate by chemically crosslinking a free amino group on the antibody to reactive side groups present within the solid-state substrate. Antibodies can be, for example, chemically cross-linked to a substrate that contains free amino, carboxyl, or sulfur groups using glutaraldehyde, carbodiimides, or GMBS, respectively, as crosslinker agents. In this method, aqueous solutions containing free antibodies can be incubated with the solid-state substrate in the presence of glutaraldehyde or carbodiimide.

A method for attaching antibodies or other proteins to a solid-state substrate is to functionalize the substrate with an amino- or thiol-silane, and then to activate the functionalized substrate with a homobifunctional cross-linker agent such as (Bis-sulfo-succinimidyl suberate (BS3) or a heterobifunctional cross-linker agent such as GMBS. For crosslinking with GMBS, glass substrates can be chemically functionalized by immersing in a solution of mercaptopropyltrimethoxysilane (1% vol/vol in 95% ethanol pH 5.5) for 1 hour, rinsing in 95% ethanol and heating at 120° C. for 4 hrs. Thiol-derivatized slides can be activated by immersing in a 0.5 mg/ml solution of GMBS in 1% dimethylformamide, 99% ethanol for 1 hour at room temperature. Antibodies or proteins can be added directly to the activated substrate, which can be blocked with solutions containing agents such as 2% bovine serum albumin, and air-dried. Other standard immobilization chemistries are known by those of ordinary skill in the art.

Each of the components (e.g., compounds) immobilized on the solid support can be located in a different predefined region of the solid support. Each of the different predefined regions can be physically separated from each other. The distance between the different predefined regions of the solid support can be either fixed or variable. For example, in an array, each of the components can be arranged at fixed distances from each other, while components associated with beads will not be in a fixed spatial relationship. The use of multiple solid support units (e.g., multiple beads) can result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

In addition, the genes described herein can also be used as markers (i.e., biomarkers) for susceptibility to or presence or progression of prostate cancer. The methods and assays described herein can be performed over time, and the change in the level of the markers assessed. For example, the assays can be performed every 24-72 hours for a period of 6 months to 1 year, and thereafter carried out as needed. Assays can also be completed prior to, during, or after a treatment protocol. Together, the genes disclosed herein can be used to profile an individual's risk or progression of prostate cancer. As used within this context, the terms "differentially expressed" or "differential expression" refers to difference in the level of expression of the biomarkers disclosed herein that can be assayed by measuring the level of expression of the products (e.g., RNA or gene product) of the biomarkers, such as the difference in level of messenger RNA transcript or a portion thereof expressed or of proteins expressed of the biomarkers. In an aspect, this difference is significantly different.

To improve sensitivity, more than one gene disclosed herein can be assayed within a given sample. Binding agents specific for different proteins, antibodies, nucleic acids provided herein can be combined within a single assay. Further, multiple primers or probes can be used concurrently. To assist with such assays, specific biomarkers can assist in the specificity of such tests.

Levels of expression can be measured at the transcriptional and/or translational levels. At the translational level, expression of any of the genes described herein can be measured using immunoassays including immunohistochemical staining, western blotting, ELISA and the like with an antibody that selectively binds to the corresponding gene or a fragment thereof. Detection of the protein using protein-specific antibodies in immunoassays is known in the art. At the transcriptional level, mRNA can be detected by, for example, amplification (e.g., PCR, LCR), or hybridization assays (e.g., northern hybridization, RNAse protection, or dot blotting). The level of protein or mRNA can be detected, for example, by using directly or indirectly labeled detection agents (e.g., fluorescently or radioactively labeled nucleic acids, radioactively or enzymatically labeled antibodies). Changes (e.g., increase or decrease) in the transcriptional levels can also be measured using promoter-reporter gene fusion constructs. For example, the promoter region of a gene encoding any of the genes disclosed herein can be fused (i.e., operably linked) to the coding sequence of a polypeptide that produces a detectable signal. Reporter constructs are well known in the art. Examples of reporter sequences include fluorescent proteins (e.g., green, red, yellow), phosphorescent proteins (e.g., luciferase), antibiotic resistance proteins (e.g., .beta.lactamase), enzymes (e.g., alkaline phosphatase).

The methods disclosed herein can be used to the outcome or predict survival for a subject having a prostate tumor. For example, a subject with a tumor that is identified to be at low risk can indicate that the subject has a good prognosis, while for a subject with a tumor that is determined to be at high risk, can indicate that the subject has a poor prognosis.

A poor prognosis for a subject can mean that the subject has a decreased likelihood of survival or decrease in time of survival compared to a subject that has been predicted to have a good prognosis. A poor prognosis can also mean that the subject has an increased risk of recurrence or metastasis as compared to a patient with a good prognosis. For example, the likelihood of five-year survival for a patient with a low risk tumor may be 90% or lower, such as 85%, 80%, 75%, 70%, 60% or lower, while the likelihood of five-year survival in the high risk group may be 50% or lower, such as 45%, 40%, 30%, 20%, 10% or lower. The median length of survival for patients with low risk tumors may likewise be 6 years or longer, such as 7 years, 8 years, 9 years, 10 years or longer, while the median length of survival in patients with high risk tumors may be 5 years or shorter, such as 4 years, 3 years, 2 years, 1 year or shorter. In one embodiment of the invention the classification of a tumor may be used to improve survival prediction using clinical parameters.

In an aspect, the methods described herein can further include treatment regimen. The treatment regimen can be determined based on the outcome of the presence or absence or expression level of one or more of NKX3.1, HOXB13, KLK3, PRAC1, PRAC2, MALAT1, HOXC6, AMACR, SCHLAP1, PCAT1, and PCA3. Subjects that have a tumor that has been classified as being a high risk tumor may need more radical or curative treatments than patients with low risk tumors. The treatment regimen can also be determined based on the stage of the prostate tumor or prostate cancer. Radical or curative treatments include but are not limited to prostatectomy, radiation, chemotherapy, castration or a combination thereof. Patients with tumors that have been identified as low risk tumors may need less or no radical or curative treatment, but can be assigned to watchful-waiting or active surveillance. In some aspects, the patients with localized cancer of high risk or intermediate risk tumor subtype may need radical or curative treatments without delay, while patients with localized cancer of low risk tumor subtype can be safely assigned to watchful waiting with minimal anxiety because castration therapy can be still a guarantee of long time survival in case of disease progression. For patients with advanced cancer at diagnosis, those of low risk subtype can get most benefit from castration therapy or anti-androgen therapy whereas patients of high risk and intermediate risk subtype may need to be treated by chemotherapy or other new therapies early.

Disclosed herein are methods of treating high risk tumors in a subject with prostate cancer. In an aspect, the method can comprise: administering a treatment of prostatectomy, radiation, chemotherapy, castration or a combination thereof. In an aspect, the subject was diagnosed prior to the treatment. In an aspect, the subject was diagnosed as having a high risk tumor by: 1) obtaining a sample from a subject with prostate cancer; 2) detecting expression levels of one or more of NKX3.1, HOXB13, KLK3, PRAC1, PRAC2, MALAT1, HOXC6, AMACR, SCHLAP1, PCAT1, and PCA3 in a sample and determining whether the expression levels of one or more of NKX3.1, HOXB13, KLK3, PRAC1, PRAC2, MALAT1, HOXC6, AMACR, SCHLAP1, PCAT1, and PCA3 are higher or lower compared to expression levels of one or more of NKX3.1, HOXB13, KLK3, PRAC1, PRAC2, MALAT1, HOXC6, AMACR, SCHLAP1, PCAT1, and PCA3 from a reference sample; and 3) diagnosing the subject with a high risk tumor when the expression levels of one or more of NKX3.1, HOXB13, KLK3, PRAC1, PRAC2, MALAT1, HOXC6, AMACR, SCHLAP1, PCAT1, and PCA3 in the sample are higher compared to the expression level of one or more of NKX3.1, HOXB13, KLK3, PRAC1, PRAC2, MALAT1, HOXC6, AMACR, SCHLAP1, PCAT1, and PCA3 from a reference sample.

Disclosed herein are methods of treating low risk tumors in a subject with prostate cancer. In an aspect, the method can comprise: withholding prostatectomy, radiation, chemotherapy, castration, anti-androgen therapy or a combination thereof from the subject with a low risk tumor In an aspect, the method can comprise administering a lower dose of radiation, chemotherapy, anti-androgen therapy or a combination thereof to the subject with a low risk tumor. In an aspect, the subject was diagnosed prior to the treatment. In an aspect, the subject was diagnosed as having a high risk tumor by: 1) obtaining a sample from a subject with prostate cancer; 2) detecting expression levels of one or more of NKX3.1, HOXB13, KLK3, PRAC1, PRAC2, MALAT1, HOXC6, AMACR, SCHLAP1, PCAT1, and PCA3 in a sample and determining whether the expression levels of one or more of NKX3.1, HOXB13, KLK3, PRAC1, PRAC2, MALAT1, HOXC6, AMACR, SCHLAP1, PCAT1, and PCA3 are higher or lower compared to expression levels of one or more of NKX3.1, HOXB13, KLK3, PRAC1, PRAC2, MALAT1, HOXC6, AMACR, SCHLAP1, PCAT1, and PCA3 from a reference sample; and 3) diagnosing the subject with a low risk tumor when the expression levels of one or more of NKX3.1, HOXB13, KLK3, PRAC1, PRAC2, MALAT1, HOXC6, AMACR, SCHLAP1, PCAT1, and PCA3 in the sample are lower compared to the expression level of one or more of NKX3.1, HOXB13, KLK3, PRAC1, PRAC2, MALAT1, HOXC6, AMACR, SCHLAP1, PCAT1, and PCA3 from a reference sample.

In some aspects, the step of a subject's risk of developing prostate cancer can be based on a pre-determined pattern of one or more of NKX3.1, HOXB13, KLK3, PRAC1, PRAC2, MALAT1, HOXC6, AMACR, SCHLAP1, PCAT1, and PCA3 in the sample can be automated. In some aspects, the step of determining a subject's risk of developing prostate cancer can be based on a pre-determined pattern of one or more of NKX3.1, HOXB13, KLK3, PRAC1, PRAC2, MALAT1, HOXC6, AMACR, SCHLAP1, PCAT1, and PCA3 in the sample is not automated. In some aspects, the step of determining a subject's risk of developing prostate cancer prostate cancer based on a pre-determined pattern of one or more of NKX3.1, HOXB13, KLK3, PRAC1, PRAC2, MALAT1, HOXC6, AMACR, SCHLAP1, PCAT1, and PCA3 in the sample can be performed manually. In some aspects, cells of prostate origin can be identified by the presence of distinct RISH spots for one or more of NKX3.1, HOXB13, KLK3, PRAC1, PRAC2, MALAT1, HOXC6, AMACR, SCHLAP1, PCAT1, for example, either NKX3.1 or PRAC1 in cells with appropriate morphology, and considered prostate cancer cells if they also were positive for PCA3.

In some aspects, the methods disclosed herein can further comprise classifying the urinary prostate cancer cells as described in the Examples. In some aspects, the methods disclosed herein can comprise a step of patient scoring as described in the Examples. In some aspects, one or more urinary prostate cells can be manually categorized into three class: (1) non-prostate cells, (2) prostate cells, or (3) prostate cancer cells (see, for example, Table 5). For example, criteria for prostate cell positivity can include that at least 5 distinct punctate spots be present in one or more of NKX3.1, HOXB13, KLK3, PRAC1, PRAC2, MALAT1, HOXC6, AMACR, SCHLAP1, PCAT1, and PCA3 channel (for example, in either the PRAC1 or NKX3-1 channel) and have a morphology consistent with cells of prostate origin. Prostate cancer cells can also have the same criteria in addition to containing at least 5 PCA3 spots. In some aspects, cells with less than 5 spots, for example, for 3 markers (PRAC1, NKX3-1 and PCA3) were classified as non-prostate cells. In some aspects, spot thresholds were based on quantification of signals in cultured prostate cells lines spiked into urine specimens. In some aspects, spot thresholds can be pre-determined. In some aspects, positive cells can be manually identified. In some aspects, a tally of positive cells can be recorded by the software during the review process. In some aspects, patients can be scored as 1) prostate cancer positive if at least one (e.g., PCA3) positive cell was detected on the slide; 2) cancer negative/prostate cell positive if at least one (e.g., NKX3-1/PRAC1+PCA3−) cell was detected; 3) cancer negative/prostate cell negative (NKX3-1/PRAC1− and PCA3−) if no prostate cells were detected; or 4) indeterminate if RISH status could not be defined due to obscuring factors or cellular overcrowding.

In an aspect, the methods disclosed herein can further include a step of treating the subject that has been diagnosed with prostate cancer.

EXAMPLES

Example 1: Cytologic Examination of Post-DRE Urine Sediments

Experimental methods. The post-DRE single-void, first-catch sampling strategy has been implemented in a Biorepository workflow disclosed herein, see, for example, FIGS. 5 and 6. Briefly, first-catch voided urine samples are refrigerated and transported to the lab from the clinic twice a day for same-day processing. Urine pellets are collected, fixed, and deposited onto mega cytofunnels for preparation of standard cytology slides by Cytospin. The slides go through cytology processing and are stored in 100% ethanol at −20° C. RNA targets are stable for years under these conditions.

Three-plex fluorescent RISH is a two-day protocol involving incubation with the 3-plex probe mix following target retrieval on Day 1 and downstream signal generation and visualization on Day 2. RISH slides are scanned using the automated Metafer digital imaging platform and Meta-Cyte software (MetaSystems, Altlusshem, Germany). The entire area of cytospin preparations are scanned in four fluorescent channels (3-plex plus DAPI) using the 10× objective and autofocusing setting. For image acquisition, a Metacyte software classifier for cell selection was developed and optimized in-house to measure fluorescent signal intensities of Opal 520, 570, and 690 fluorophores in all DAPI positive cells. A gallery of cell images can be generated by the software and sorted by total fluorescent signal intensity. Gallery images can be manually screened and scored, and positive cells will be validated by visual inspection and imaging under high-magnification (40× objective). Cells of prostate origin were identified by presence of distinct RISH spots for either Nkx3.1 or PRAC1 in cells with appropriate morphology, and considered prostate cancer cells if they also were positive for PCA3 (Table 1).

TABLE 1

Expected staining characteristics of cells in urine sediments for multiplex RNA-ISH.

| Label | Normal | Prostate cells | Prostate cancer cells |
| --- | --- | --- | --- |
| Nkx3.1 | No | Yes | Yes |
| PRAC1 | No | Yes | Yes |
| PCA3 | No | No | Yes |

Given the rich selection of RNA markers and the highly sensitive and specific RISH probes that can be designed from almost all RNA targets, continued development of urine RISH tests by leveraging RNA expression data, novel RISH technology, and available patient and data resources will help drive the field of next-generation urinary RNA markers for prostate cancer.

A tripartite approach can be used for developing a pipeline of urine RNA markers. Existing patient specimens and data, development of novel RNA detection technology, and extensive in-house RNA sequencing data will be leveraged from which RNA detection targets can be selected and prioritized. These existing resources will allow the focus to be on marker qualification, assay development using spike-in controls, and initial evaluation in existing urine cytology specimens and a small subset of urine cytology specimens not included in the case control design.

RNA sequencing data and marker selection. The robustness of the RISH probes for cancer cell detection to a large extent will depend on marker selection and qualification following rigorous evaluation. The assay sensitivity can be further improved by refining the protocols and markers to be selected on the basis of the existing RNA-Seq data, as well as inclusion of additional candidate RNA targets emerging from the prostate cancer literature. In that regard, the approach disclosed herein will be guided by the extensive RNA-Seq data generated from five different categories of prostate specimens with detailed clinical and pathological data: including normal prostate glands from 10 organ donors, 20 untreated prostate tumors with APF and 20 from normal prostate tissue adjacent to untreated prostate cancers, over 50 castration-resistant prostate cancer metastases, and circulating tumor cells from mCRPC patients.

Here, an experiment focused on optimization of biospecimen collection, processing, and preparation for cytologic examination was performed. Following collection of the first 50 mL of voided urine after DRE, urine sediments were fixed on slides by Cytospin using the mega funnel cartridges, and stored in a −20° C. freezer. Papanicoaou (pap) stain was performed on one slide per specimen to assess slide adequacy, cell density, and cell morphology. Eosin azure stains cytoplasm blue/green; orange-G 6 stains keratin orange; and hematoxylin is a nuclear stain of blue/violet. Cytologic examination of these post-DRE urine sediments revealed a complex and varied mixture of cellular and acellular contents (FIG. 2), highlighting the challenge in identifying rare prostate cancer cells solely on the basis of morphological criteria. Highly sensitive and specific molecular detection methods for prostate cancer cells are essential in order for cells of prostate origin to be visualized and characterized.

Figure 7:
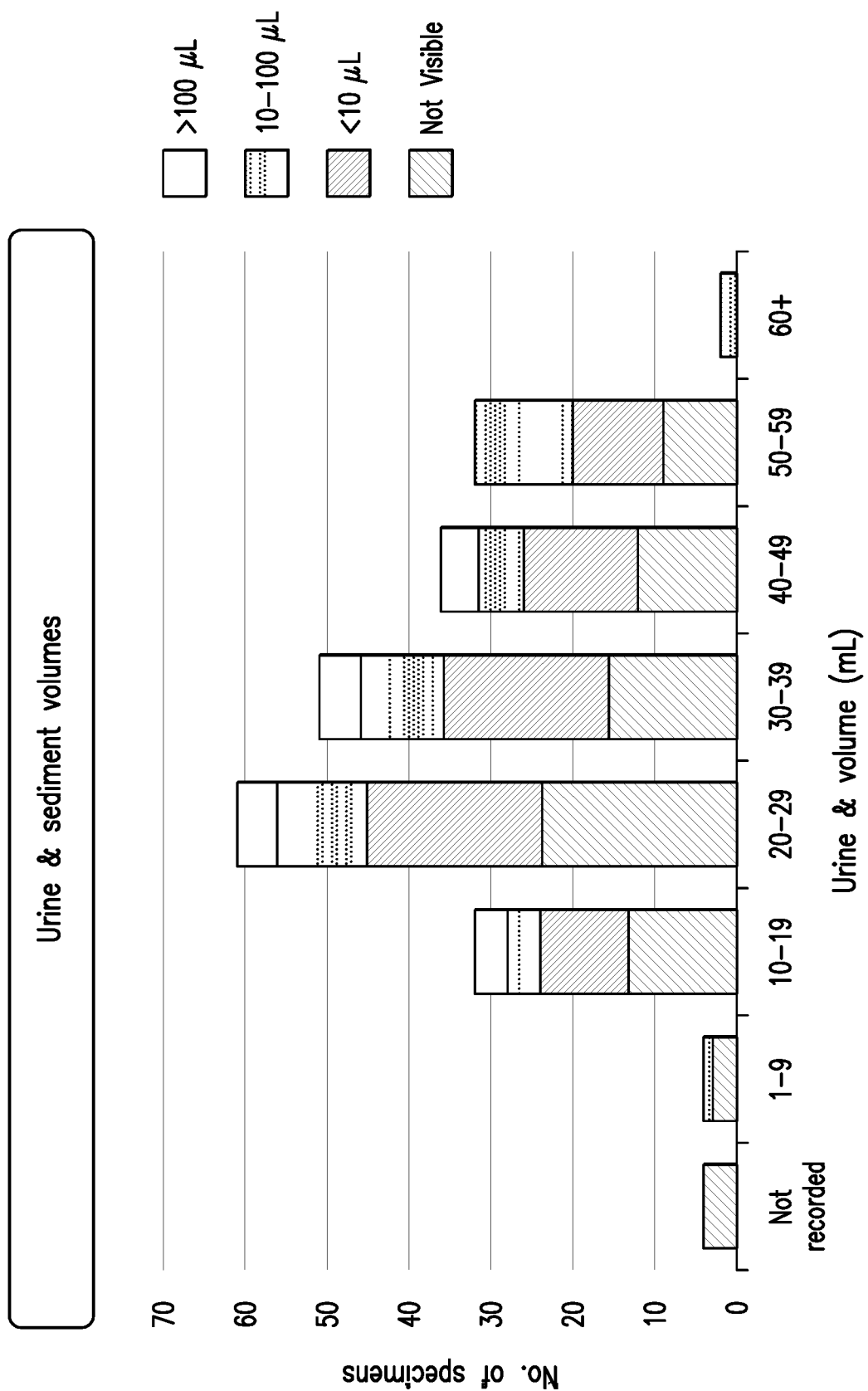
FIG. 7 is a graph showing urine and sediment volumes.
Figure 8:
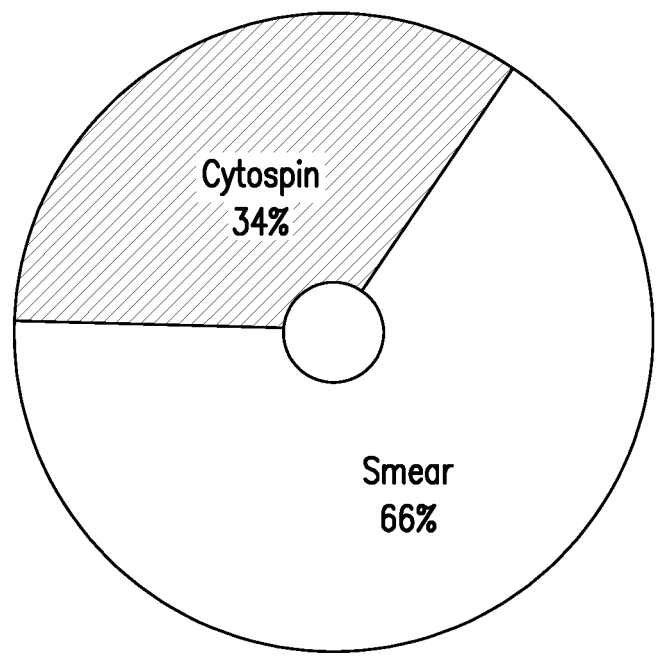
FIG. 8 shows comparison smears versus cytopsin methods of slide preparation.
Figure 9:
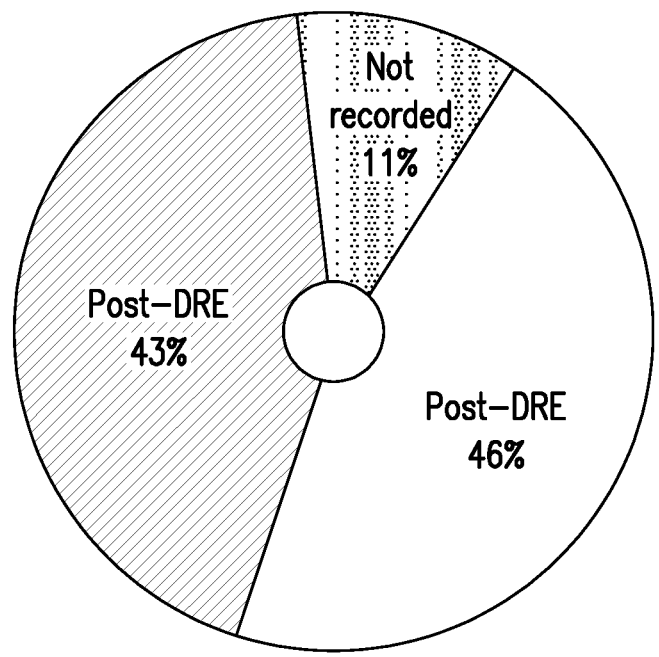
FIG. 9 shows a further characterization the urine sample based on pre-DRE, post-DRE or samples that were not recorded.
Figure 10:
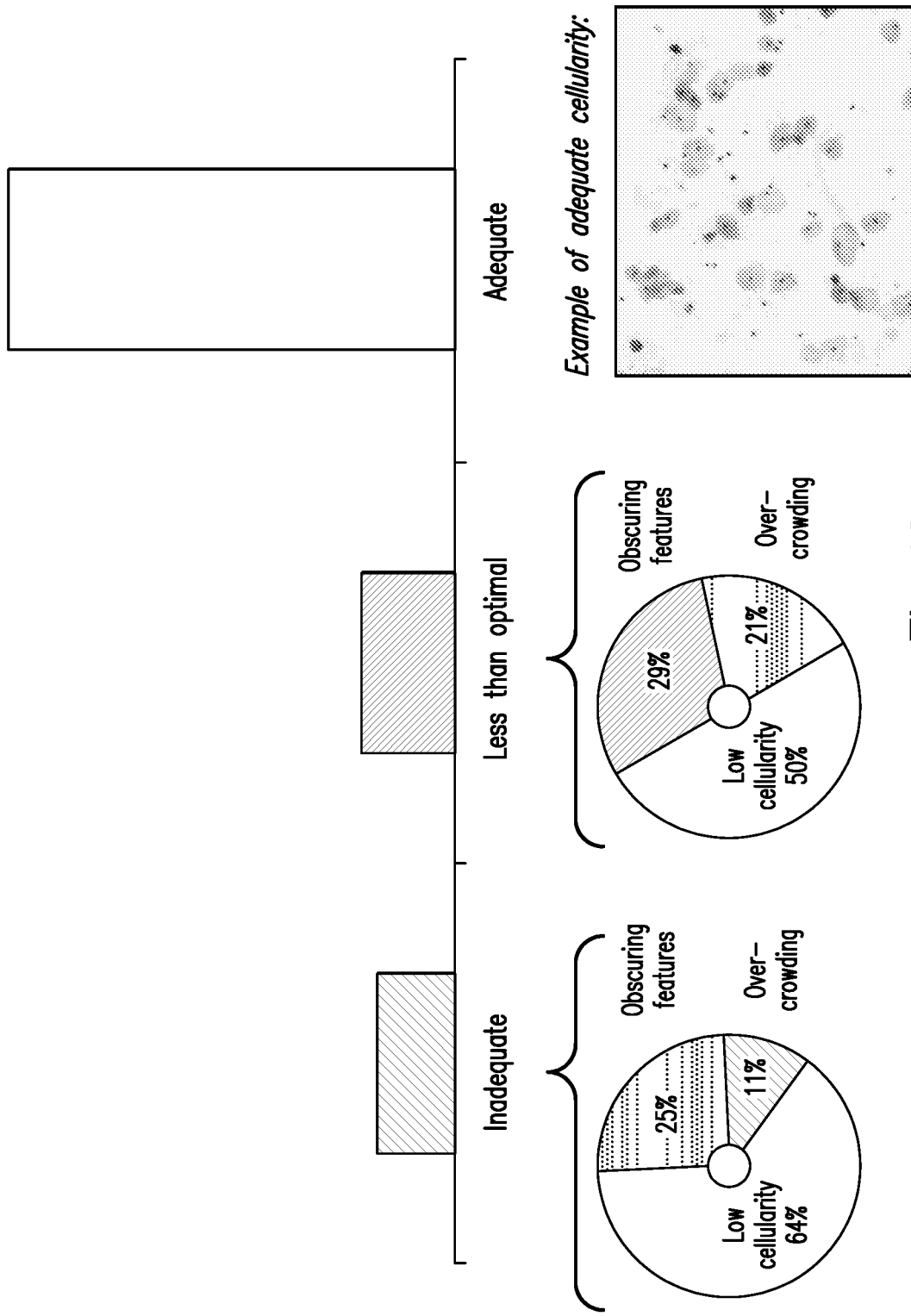
FIG. 10 shows that the slide adequacy of the samples was determined by microscopic evaluation of pap stained slides.

Urine samples (n=222) were obtained through the JHBUI biorepository from men suspected or previously diagnosed with prostate cancer. As positive controls, urine specimens from a female donor were spiked with either 22Rv1 or LNCaP cells. FIG. 2 shows the components of urine sediment using a pap stain. FIG. 7 shows urine and sediment volumes. FIGS. 8 and 9 show the results of further characterization of the slide preparation method and pre- or post-DRE void as disclosed herein. Slide adequacy was determined by microscopic evaluation of pap stained slides; adequate: cellular material observed, no/minimal obstruction due to acellular debris or overcrowding; less-than-optimal: slide displays a feature that hinders visualization of single cells (overcrowded areas, clumping, debris), or limited cellular content present; and inadequate: significant overcrowding that prevents observation of single cells, excess debris, or scant cellular material present, see, for example, FIG. 10.

Figure 11:
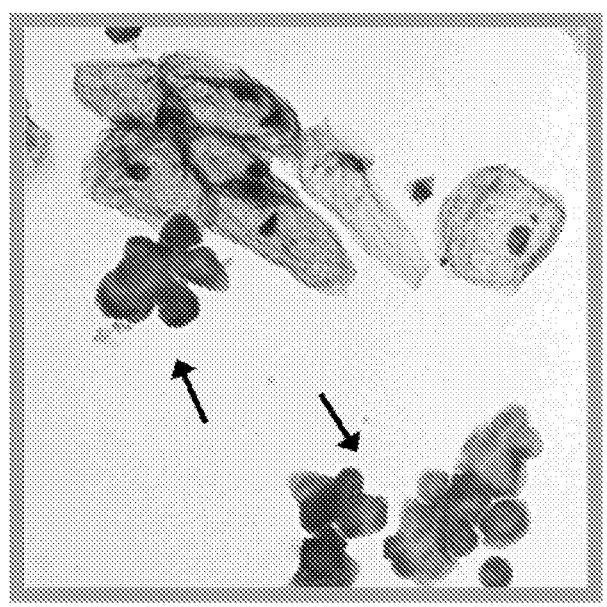
FIG. 11 shows clusters of 22Rv1 cells in urine samples (arrows) using the pap stain.

Chromogenic RISH methods for prostate cell detection. The feasibility of detecting cells of prostate origin in post-DRE urine sediments by chromogenic RISH was also evaluated. RISH is a sensitive and specific method of detecting RNA targets with multiplexing ability to discriminate prostate cells from prostate cancer cells that also allows direct visualization of individual cells. Thus, RISH can be used as a cell-based evaluation method that will overcome limitations of existing PCR-based urinary prostate cancer detection tests. RISH was performed using RNAscope reagents (chromogenic and fluorescent) on slides with adequate cellularity. RISH probes for NKX3.1 and HOXB13, two markers highly specific for prostate cells were first used as part of the feasibility studies. The data show that cells of prostate origin can be reliably detected in patient samples as well as CWR22Rv1 prostate cancer cells spiked into urine samples (FIG. 3). FIG. 11 also shows that the pap stain can identify prostate cells in clusters of 22Rv1 cells in urine specimens (arrows). These experiments established that nearly 100% of the spiked cells can be recovered (data not shown). Although HOXB13 and NKX3.1 RISH signals identify cells of prostate origin, they are not prostate cancer specific (i.e., they are highly expressed in both prostate cancer cells and normal prostate epithelial cells). As such, it is important to develop a multiplexed RISH assay including RNA detection targets specific for both prostate cells (i.e., expressed in both prostate cells and prostate cancer cells), and RNA targets specific to prostate cancer cells (i.e., not expressed in normal prostate cells), ideally with differential expression in aggressive/high-risk vs indolent cancer cells.

Screening for prostate- and prostate cancer-specific probes. Due to the importance of multiplexing, a panel of candidate RNA markers were screened focusing on evaluation of specificity for cells of prostate origin or prostate cancer cells using fluorescent RISH. These RNA targets were selected following evaluation of internal RNA sequencing data sets. Both mRNA and long noncoding RNA targets were evaluated including NKX3.1, HOXB13, KLK3, Prostate and Colon (PRAC) 1, PRAC2, MALAT1, HOXC6, AMACR, and PCA3. As shown in FIG. 4, these probes demonstrated varying degree of robustness in detecting CWR22Rv1 cells spiked into the urine samples. Although PCA3 did not show robust RISH signal in CWR22Rv1 cells due to low expression of PCA3 in cell lines, highly robust PCA3 signals were observed in patient samples. Mainly on the basis of detection specificity, PRAC1, NKX3.1, and PCA3 were selected to be included in a prototype, multiplex fluorescent RISH assay. FIG. 12 also shows the results of the multiplex RISH performed on urine samples spiked with 22Rv1 cells.

Detection of prostate cancer by multiplex RISH in post-DRE urine sediments. Following further optimization of the PRAC1/NKX3.1/PCA3 multiplexed fluorescent RISH assay, the test was applied to a total of 72 post-DRE urine specimens. Among these 72 patient samples, 11 were negative for cells of prostate origin, 42 were positive for cells of prostate origin (positive for PRAC1/NKX3.1), and 19 were positive for prostate cancer cells (positive for PRAC1/NKX3.1/PCA3). Notably, PCA3 positive cells were also positive for PRAC1/NKX3.1 in all cases with positive detection of urinary prostate cancer cells.

Figures 14A, 14B, 14C, 14D:
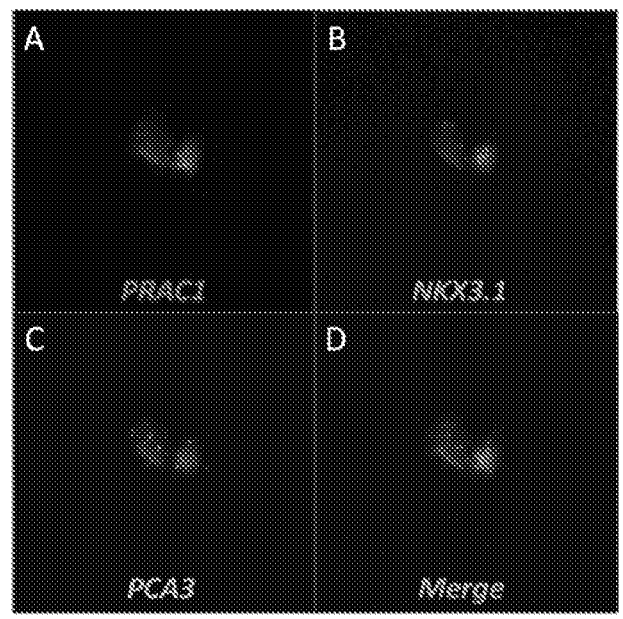
FIGS. 14A-D show prostate cancer cells (often in clusters) detected in post-DRE urine sediments obtained from patients with prostate cancer in patient sample 1. Multiplex RISH for PRAC1 (A), NKX3.1 (B), and PCA3 (C); counterstained with DAPI.

The NKX3.1/PRAC1/PCA3 multiplex test was applied to 19 post-DRE urine specimens obtained from patients with prostate cancer. The expected staining characteristics NKX3.1/PRAC1/PCA3 multiplex test are shown in Table 2 and the results are shown in Table 3. Two examples of prostate cancer cells (often in clusters) detected in post-DRE urine sediments obtained from patients with prostate cancer are shown in FIGS. 13 and 14.

TABLE 2

Expected staining characteristics.

| Label | Normal Cell | Prostate Cell | Prostate Cancer Cell |
|---|---|---|---|
| DAPI | Yes | Yes | Yes |
| NKX3.1 | No | Yes | Yes |
| PRAC1 | No | Yes | Yes |
| PCA3 | No | No | Yes |

TABLE 3

Results.

| Label | No. specimens w/positive cells |
|---|---|
| NKX3.1 and/or PRAC1 | 11 (58%) |
| NKX3.1 and/or PRAC1 and PCA3 | 6 (32%) |

All but one of the 19 samples tested positive for PRAC1/NKX3.1/PCA3 had positive cancer detection by biopsy, and high risk features (Gleason 4) were present in 72% (13 out of 18) of the biopsies with positive cancer detection. In contrast, among the 53 samples that did not have a positive PRAC1/NKX3.1/PCA3 call, 22 were negative for cancer on biopsy, 20 were positive for cancer on biopsy but without high-risk features, and only 21% (11 out of 53) had high-risk features that were undetected by the urine test. Described herein is a multiplexed fluorescent RISH assay for specific detection and visualization of prostate cancer cells in post-DRE urine samples. In addition, this non-invasive method has the capacity to differentiate (predict) cancer vs normal biopsy findings on biopsy, as well as high-risk vs low-risk cancers that have different treatment and management trajectories.

Example 2: A Urine Test Highly Specific for Prostate Cancer Detection

Introduction. Urine is one of the most accessible and readily available biofluids that can be collected repeatedly and at frequent intervals. Prostatic material including secreted fluid, exfoliated prostate cells, cellular degradation products, and non-cellular elements such as corpora amylacea, is released into urine during micturition (Tosoian J J, et al. (2016) *The Urologic clinics of North America* 43(1):17-38; Rupp M, et al. (1994) *Cytopathology: official journal of the British Society for Clinical Cytology* 5(3):164-170; Scott W W & Huggins C. (1942) *Endocrinology* 30(1):107-112; and Breul J, et al. (1994) *European urology* 26(1):18-21). The amount of prostate material in urine can be increased upon digital rectal exam (DRE), which displaces and propels cells and secretions into the urethra where they subsequently exit the body through the voiding of urine (Moberg P J, et al. (1984) *Urologia Internationalis* 39(4):189-192 and Hendriks Rianne J, et al. (2016) *Clinical chemistry and laboratory medicine* 54(3):483).

Exfoliated prostate cells shed into urine represent a promising resource for diagnosis, surveillance, and prognosis of prostate cancer. Early cytological studies established that prostate cells in the urine sediment can be detected microscopically using conventional staining techniques (Papanicolaou G N & Marshall V F. (1945) *Science* (New York, N Y.) 101(2629):519-520). Although the ability to recover prostate cells via collection of urine has been demonstrated, enthusiasm for using conventional cytological methods to identify urinary prostate cancer cells has been hindered by unreliable detection and poor sensitivity in the clinical setting. The unsatisfactory performance of urine cytology for prostate cancer is likely due to the rarity of prostate cell populations in voided urine and reliance on morphological identification amongst the background of other formed elements present in the sediment (Sharifi R, et al. (1983) *Urology* 21(4):417-420).

Some improvement upon conventional cytology methods was achieved through immunocytochemical labeling of urine sediment with prostate-specific markers (Fujita K, et al. (2009) *Human Pathology* 40(7):924-933; Varma V A, et al. (1988) *Diagnostic cytopathology* 4(4):300-305; and Nickens K P, et al. (2015) *Prostate* 75(9):969-975). This approach yields high diagnostic specificity but has yet to overcome the unacceptably low sensitivity encountered with conventional cytology. However, investigations of molecular urine cytology for prostate cancer have been limited, involved a small number of biomarkers and have been restricted to antibody-based detection modalities.

As an alternative to immunostaining, RNA in situ hybridization (RISH) is an attractive strategy to facilitate detection of prostate cells in urine. The RISH method allows highly sensitive and specific detection of RNA molecules, including noncoding RNA markers, in intact cells. Described herein are methods for detection of prostate cancer involving RISH and microscopic assessment of individual prostate cells obtained through collection of urine. Following selection of prostate-specific RNA markers including NKX3.1, PRAC1, and PCA3, a workflow was developed, validated and implemented for processing urine samples amenable to molecular cytology by RISH detection of exfoliated prostate cells. The clinical applicability of RISH-based detection of prostate cancer on post-DRE urine specimens obtained from patients suspected of harboring prostate cancer was assessed.

Material and Methods. Patient population. This study included collection of urine specimens from two patient cohorts. Feasibility of prostate cell detection by RISH was evaluated using the first cohort of patients, which consisted of 19 retrospective urine specimens from patients diagnosed with prostate cancer, prior to initiation of any local treatments. Diagnostic performance of the disclosed RISH assay was evaluated in the second cohort of 98 patients in which post-DRE urine specimens were prospectively collected from men with indications for prostate biopsy. The samples from this cohort (n=98) were processed and scored while blinded to cancer status and clinical characteristics.

Urine collection, cytology slide preparation, and storage. First-catch urine was obtained following an attentive digital rectal exam (DRE) and immediately refrigerated at 4° C. until processed. The specimens were processed within 4 hours. The entire urine volume was centrifuged at 1,000×g for 10 minutes. Urine sediments were fixed in 10% neutral buffered formalin for 10 minutes at room temperature. Fixed sediments were centrifuged again and resuspended in 8 mL phosphate buffered saline. Four slides were prepared for each patient by adding 2 mL of cell suspension to the funnel of cytospin slide cartridges (Shandon E Z Megafunnel, Thermo Scientific, Waltham, Mass.) and centrifuged for 5 minutes at 1,000 rpm (Shandon Cytospin IV, Thermo Scientific). Slides were dried at 37° C. on a slide warmer for 15 minutes, dehydrated through a series of graded ethanol solutions, then stored at −20° C. in coplin jars filled with 100% ethanol.

RNA in situ hybridization. Detection of prostate and prostate cancer cells was achieved by a 3-plex RNA in situ hybridization (RISH) assay (RNAscope Multiplex Fluorescent v2 Assay Kit, Advanced Cell Diagnostics, Newark, Calif.). The following three RNA markers were selected and corresponding probes designed: NKX3-1, PRAC1 and PCA3 (Table 4). These targets were selected based on their prostate-specific expression. NKX3-1 and PRAC1 positivity identified cells of prostate origin and PCA3 positivity differentiated malignant from normal prostate cells. Following probe hybridization and signal amplification steps, slides were subjected to scanning, image processing, and scoring

TABLE 4

RISH probes

| Target gene | NKX3-1 | PCA3 | PRAC1 |
|---|---|---|---|
| Catalog number | 436681 | 312201 | 400841 |
| Full gene name | NK3 homeobox 1 | Prostate cancer associated 3 | PRAC1 small nuclear protein |
| Species | *Homo sapiens* | *Homo sapiens* | *Homo sapiens* |
| Gene type | Protein coding | Non-coding RNA | Protein coding |
| Alternate names | NKX3; BAPX2; NKX3A; NKX3.1 | DD3; PCAT3; NCRNA00019 | PRAC; C17orf92 |
| Entrez gene ID | 4824 | 50652 | 84366 |
| Accession number | NM_006167.3 | NR_015342.1 | NM_032391.2 |
| Unigene | Hs.55999 | Hs.663766 | Hs.116467 |
| Probe region | 362-1299 | 1683-2796 | 19-278 |
| No. of pairs | 20 | 20 | 6 |

Classification of urinary prostate cells and patient scoring. Individual cells were manually categorized into three classes: (1) non-prostate cells, (2) prostate cells, or (3) prostate cancer cells (Table 5). Criteria for prostate cell positivity required that at least 5 distinct punctate spots be present in either the PRAC1 or NKX3-1 channel and have morphology consistent with cells of prostate origin, whereas prostate cancer cells had same requirements in addition to containing at least 5 PCA3 spots. Cells with less than 5 spots for the 3 markers were classified as non-prostate cells. Spot thresholds were based on quantification of signals in cultured prostate cells lines spiked into urine specimens. Positive cells were manually identified by the reviewer and a tally of positive cells was recorded by the software during the review process. Patients were scored as 1) prostate cancer positive if at least one PCA3 positive cell was detected on the slide; 2) cancer negative/prostate cell positive if at least one NKX3-1/PRAC1+PCA3-cell was detected; 3) cancer negative/prostate cell negative (NKX3-1/PRAC1- and PCA3-) if no prostate cells were detected; or 4) indeterminate if RISH status could not be defined due to obscuring factors or cellular overcrowding.

TABLE 5

RISH criteria for classification of cells in urine sediments

| Marker | Non-prostate cell | Prostate cell | Prostate cancer cell |
|---|---|---|---|
| NKX3-1 | No | Yes | Yes |
| PRAC1 | No | Yes | Yes |
| PCA3 | No | No | Yes |

Statistical analysis. Patients with biopsy-confirmed prostate cancer were stratified by risk according to D'Amico criteria (D'Amico A V, et al. (1998) *Jama* 280(11):969-974). Epstein criteria was used to define cases of clinically insignificant prostate cancer (Epstein J I, et al. (1994) *Jama* 271(5):368-374). Analyses of Biomarker Status with age, race, PSA baseline, and PSA density were performed using the one-way analysis of variance (ANOVA) ($P<0.05$ is considered as statistically significant). Analyses of Biomarker Status with Gleason sum, known cancer, risk status, significant cancer, and cancer status were conducted by crosstabulation using Fisher's Exact Test, ($P<0.05$ is considered as statistically significant).

D'Amico risk status was also determined. Risk status can be classified as low, intermediate or high. Low risk indicates subjects with a PSA level that is less than or equal to 10, a Gleason score that is less than or equal to 6, or are in clinical stage T1-2a. Intermediate risk indicates subjects with a PSA level between 10 and 20, a Gleason score of 7, or are in clinical state T2b. High risk indicates subjects with a PSA level of more than 20, a Gleason score equal or larger than 8, or are in clinical stage T2c-3a.

Cell culture and spiking experiments. LNCaP and 22Rv1 cells were obtained from the American Type Culture Collection (ATCC, Manassas, Va.). Cells were cultured in RPMI 1640 supplemented with 10% fetal bovine serum. Known quantities of LNCaP or 22Rv1 cells were spiked into control urine to simulate patient urine specimens. Spiked samples were processed following the same procedures as patient specimens.

RNA in situ hybridization. Urine cytology slides were heated at 60° C. on a slide warmer for one hour. Slides were pretreated with hydrogen peroxide for 10 minutes, followed by boiling for 10 minutes in 1× target retrieval solution (Advanced Cell Diagnostics). Slides were hybridized with target probes (Table 4) for two hours at 40° C. Signal amplification steps were performed using RNAscope Multiplex Fluorescent v2 Assay Kit (Advanced Cell Diagnostics) according to manufacturer instructions. Fluorescent labeling of probes was performed by tyramide signal amplification using Opal 520, 570 and 650 fluorophores (Perkin Elmer, Waltham, Mass.) (Table 6). Fluorophores were diluted 1:100 in TSA amplification buffer (Advanced Cell Diagnostics) and incubated for 10 minutes at 40° C. Slides were counterstained with 4'6-diamidino-2-phenylindole (DAPI) and coverslips were mounted with Prolong Gold Anti-Fade Mounting Media (Life Technologies, Carlsbad, Calif.).

several imaging processing and segmentation parameters described in Table 7. Isolated and cropped images of each cell are presented in a gallery for interactive user review and scoring. Gallery images of cells captured using the 40× objective were scored manually on the basis of morphology and RISH signal positivity.

TABLE 7

| Microscope and image acquisition settings | | | |
|---|---|---|---|
| Microscope | Carl Zeiss AxioImager 2 | | |
| Acquisition software | Metafer5 | | |
| Reflector cubes | DAPI, FITC, DsRED, Cy5, Cy7 | | |
| Objective lenses | 10x Plan-apochromat | 20x Plan-apochromat | 40x Plan-neofluar |
| Numerical aperture | 0.45 | 0.8 | 0.75 |
| Immersion | Air | Air | Air |
| Camera | Metasystems Coolcube 2 m, CCD monochrome | | |
| Resolution | 2336 × 1752 pixels | | |
| Pixel size | 5.5 µm × 5.5 µm | | |
| Exposure time | Variable | | |
| No. of acquired planes | 3 | | |
| Z-step | 0.75 µm | | |
| Gain | 5 | | |
| Nuclei recognition criteria | DAPI intensity threshold = 20%, area = 20-500 µm$^2$, maximum relative concavity depth = 0.5, maximum aspect ratio = 2 | | |
| Image processing and segmentation steps | Steps performed after DAPI object recognition. Segment cells: extend counterstain mask by 3 µm and apply mask; background reduction: subtract histogram max; spot enhancement: top hat transformation, smoothing filter. | | |

TABLE 6

| Fluorescent dyes | | | | |
|---|---|---|---|---|
| Fluorophore | DAPI | Opal 520 | Opal 570 | Opal 650 |
| Supplier | Advanced Cell Diagnostics | Perkin Elmer | Perkin Elmer | Perkin Elmer |
| Catalog number | 320858 | FP1487001KT | FP1488001KT | FP1496001KT |
| Excitation (nm) | 358 | 494 | 550 | 627 |
| Emission (nm) | 461 | 525 | 570 | 650 |
| Metafer Filter | DAPI | FITC | DsRed | Cy5 |
| Pseudocolor | Blue | Green | Red | White |

Automated fluorescent slide scanning. Automated slide scanning was performed using the Metafer platform (MetaSystems, Altlussheim, Germany). Images were acquired using an Axio Imager Z2 epi-fluorescence microscope (Carl Zeiss, Oberkochen, Germany) equipped with a motorized slide scanning stage, coupled to a CoolCube CCD monochrome camera. Automated imaging was carried out with Metafer5 software using a classifier designed in-house to perform the following actions. First, the entire area of Cytospin slides was scanned under low magnification (10× objective) to identify regions containing cells using a DAPI filter. Cells were recognized by the software via identification of DAPI nuclei and cell coordinates were stored to denote regions of interest for 40× image acquisition. Regions without cells were not imaged. High magnification images were captured using the 40× objective in three focal planes, 0.75 µm distance, in three channels (Opal 520, Opal 570, Opal 650) and in a single focal plane for the counterstain channel (DAPI). Focal plane images were integrated into a single image for each channel. Images of every individual cell captured by the classifier were subjected to Development of a 3-plex RISH test for identification of prostate cells in urine. To assess cell recovery efficiency of the slide preparation technique, LNCaP cells were spiked into urine at various concentrations. Urine cells at quantities ranging from $1\times10^2$-$1\times10^5$ were cytospun onto slides and the number of recovered LNCaP cells was quantified. The mean recovery rates ranged from 55%-82% (FIG. 15A). Given the number of harsh pretreatment and washing steps, detachment of cells from the slide throughout the procedure was a concern. Therefore, it was evaluated how RISH pre-treatment conditions effected rate of cell loss by spiking $5\times10^3$ cells into urine and comparing recovery across the various optimization conditions tested (FIG. 15A). Cell loss throughout the entire RISH procedure was further assessed by counting number of cells remaining on the slide during the course of the RISH procedure (FIG. 15C). The greatest loss of cells occurred during the target retrieval step and cell loss increased with longer protease incubation times, but amplification and wash steps did not significantly influence cell retention.

To optimize the RISH procedure for cytology specimens, various pretreatment conditions were tested followed by hybridization and amplification steps, then signal quality in prostate cells spiked into urine was assessed. It was observed that elimination of the protease step did not adversely affect spot number or intensity, and therefore was removed from the procedure because it negatively affected adherence of cells to the slide. The optimized protocol was applied to spiked slides, first hybridizing with probes individually to assess specificity and signal intensity.

Numerous punctate spots in NKX3-1 and PRAC1 channels were identified in LNCaP and 22Rv1 cells spiked into urine. Native urine cells exhibited minimal fluorescent signal demonstrating specific expression of RISH spots in the prostate cell population (FIG. 19). Spot counts and representative images of spiked cells hybridized with probes for NKX3-1, PRAC1 and PCA3 are shown in FIGS. 18A-C. Next, these three transcripts were targeted by multiplex labeling for simultaneous detection. Multiplex labeling achieved comparable results to hybridization with single probes (FIG. 18D).

Figure 17C:
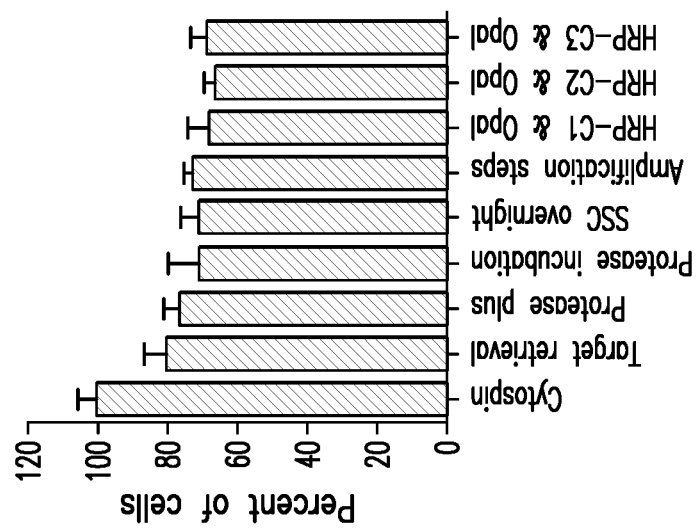
FIGS. 17A-F shows the results of using a 3-plex RISH test for identifying prostate cells in urine.
Figure 17B:
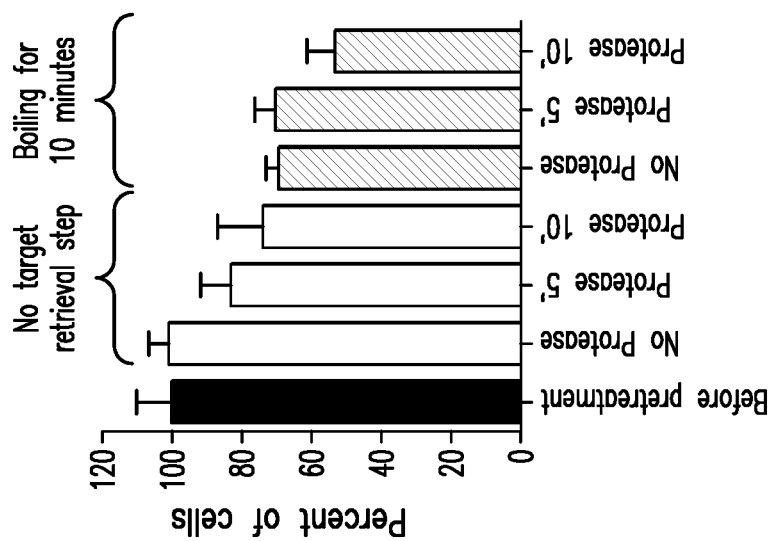
Figure 17A:
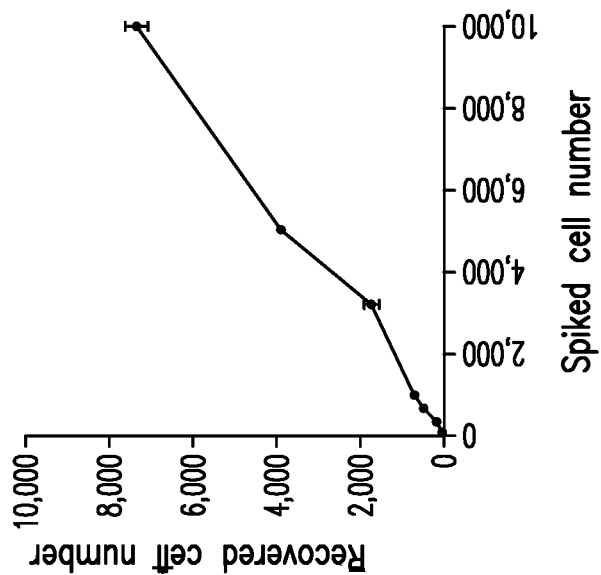
Figure 17F:
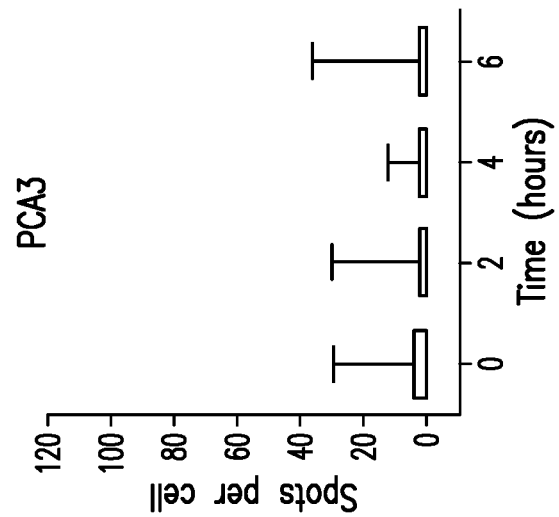
Figure 17E:
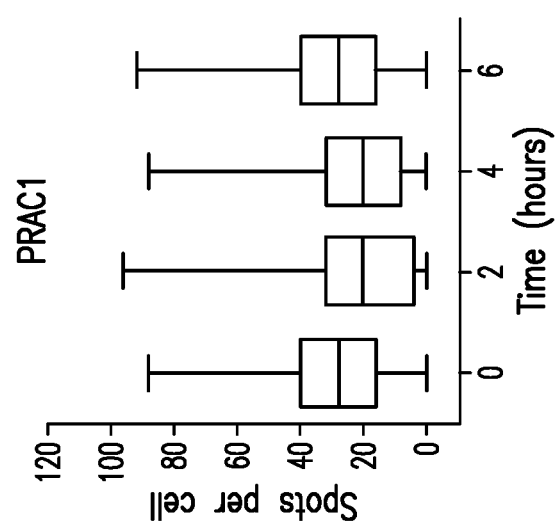
Figure 17D:
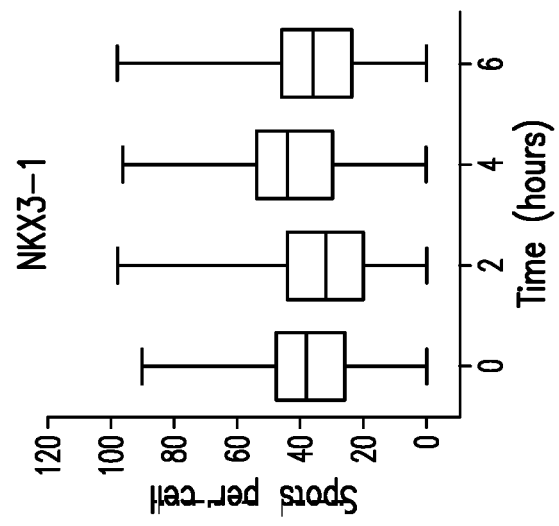
Figure 20:
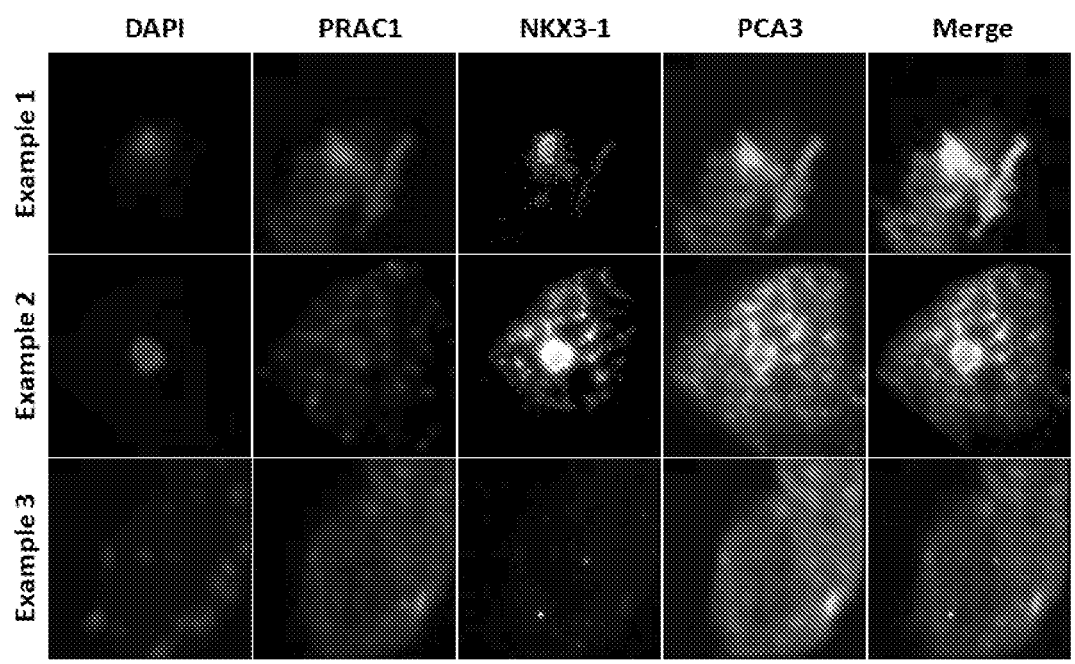
FIG. 20 shows examples of non-specific fluorescence in patient urine samples following multiplex RISH for PRAC1 (red), NKX3-1 (white), and PCA3 (green): amorphous debris (1), auto-fluorescent urothelial cell (2), urine cast (3).

Given the instability of RNA and high level of RNases in urine, storage time after sample collection could negatively impact integrity of RNA targets and interfere with interpretation of RISH results. Therefore, multiplex RISH was performed on cells spiked into urine after 0, 2, 4, and 6 hours storage at 4° C. No difference in average number of spots per cells across time points was observed (FIGS. 17D-F), indicating specimens could be stored for several hours before processing without degradation of RNA targets.

In negative control slides prepared from urine sediment without any spiked prostate cells, some non-specific, punctate fluorescence signal was observed following RISH. Generally, the spots found in urothelial and other non-prostate cell types were low in number (1-3 spots per cell) and these cells could be easily distinguished from the robust fluorescence observed in prostate cells. Based on these observations, 5 spots per cell was set as the minimum cutoff for defining positivity when analyzing patient specimens. Other sources of background signal included autofluorescence, appearing as homogeneous, broad-spectrum fluorescence, either homogeneously throughout the cell or with granular localization pattern (FIG. 19). Due to the large assortment of background and non-specific signals encountered, the image analysis parameters and spot-counting algorithm were not suitable for all specimens, thus fully automated spot counting and cell classification was not possible. To ensure correct classification of cells and accurate quantification of RISH spots, a semi-automatic approach was adopted in which interactive spot count adjustments were made during user review of gallery images.

Results. Assay development. RISH assay development and optimization was performed using urine specimens spiked with LNCaP and 22Rv1 cell lines. Spiked prostate cells could be readily identified by numerous, punctate spots in NKX3-1 and PRAC1 channels, whereas surrounding urothelial and other cell types exhibited minimal fluorescent signal demonstrating specific expression of RISH spots in the prostate cell population (FIG. 19).

Feasibility of RISH detection in clinical specimens. After the functionality of the RISH assay was established using cell lines, it was next tested whether the assay could detect prostate cells in urine specimens obtained from patients. As a preliminary feasibility assessment of performing RISH on patient samples, 19 specimens were selected based on prostate cancer status (Table 9). The 19 patients included in this preliminary assessment had been previously diagnosed with prostate cancer but were untreated. Gleason scores of 6, 7 and ≥8 were identified in 10 (53%), 4 (21%), and 5 (26%) patients, respectively. PSA levels ranged from 3.1-26.2 ng/mL (Table 8).

TABLE 8

RISH results for patient cohort 1 (n = 19 patients with prostate cancer)

| RISH Classification | Cancer positive | Cancer negative | | Indeterminate | All patients |
| --- | --- | --- | --- | --- | --- |
| | | Prostate cell positive | Prostate cell negative | | |
| Markers | NKX3-1/PRAC1+ PCA3+ | NKX3-1/PRAC1+ PCA3− | NKX3-1/PRAC1− PCA3− | Not scored | N/A |
| N | 6 | 5 | 4 | 4 | 19 |
| Age, median (IQR) | 73 (64.8-79.3) | 64 (63-72.5) | 58 (52-63.3) | 76 (65.8-79.5) | 66 (62-74) |
| Race | | | | | |
| White | 5 | 4 | 4 | 4 | 17 |
| Black | 1 | 0 | 0 | 0 | 1 |
| Unknown | 0 | 1 | 0 | 0 | 1 |
| PSA (ng/mL), median (IQR) | 8.5 (4.8-18.0) | 7.0 (5.6-8.7) | 6.9 (5.6-7.9) | 4.4 (3.3-7.9) | 6.9 (5.4-8.5) |
| PSA Density, median (IQR) | 0.16 (0.06-0.50) | 0.08 (0.07-0.11) | 0.18 (0.09-0.27) | 0.1 (0.09-0.12) | 0.09 (0.08-0.23) |
| Gleason score | | | | | |
| 6 | 2 | 3 | 2 | 3 | 10 |
| 7 | 3 | 1 | 0 | 0 | 4 |
| ≥8 | 1 | 1 | 2 | 1 | 5 |
| Epstein criteria | | | | | |
| Not significant | 1 | 2 | 1 | 2 | 6 |
| Significant PCa | 5 | 3 | 3 | 2 | 13 |

TABLE 8-continued

RISH results for patient cohort 1 (n = 19 patients with prostate cancer)

| RISH Classification | Cancer positive | Cancer negative Prostate cell positive | Cancer negative Prostate cell negative | Indeterminate | All patients |
|---|---|---|---|---|---|
| D'Amico risk status | | | | | |
| Low | 1 | 3 | 2 | 3 | 9 |
| Intermediate | 4 | 1 | 0 | 0 | 5 |
| High | 1 | 1 | 2 | 1 | 5 |

IQR, interquartile range;
N/A, not applicable;
PCa, prostate cancer;
PSA, prostate specific antigen

TABLE 9

Clinical characteristics of patient population (cohort 1, n = 19)

| Patient No. | Age | Race | PSA (ng/mL) | PSA Density [a] | Prostate biopsy | Gleason score | Risk Status [b] | Tumor per core (%) | No. positive cores | Significant PCa [c] |
|---|---|---|---|---|---|---|---|---|---|---|
| 3539 | 58 | Caucasian | 5.2 | 0.09 | Positive | 8 | High | 100 | 5 | Yes |
| 3650 | 73 | Caucasian | 7.0 | 0.09 | Positive | 6 | Low | 10 | 2 | No |
| 3688 | 79 | Caucasian | 15.3 | 0.40 | Positive | 6 | Intermediate | 10 | 1 | Yes |
| 3689 | 64 | Caucasian | 5.4 | 0.12 | Positive | 6 | Low | 30 | 4 | Yes |
| 3692 | 65 | Caucasian | 6.9 | 0.10 | Positive | 6 | Low | 10 | 1 | No |
| 3693 | 74 | Caucasian | 3.2 | 0.12 | Positive | 6 | Low | 30 | 2 | No |
| 3728 | 74 | Caucasian | 5.4 | 0.08 | Positive | 7 | Intermediate | 80 | 2 | Yes |
| 3738 | 80 | Caucasian | 3.4 | 0.11 | Positive | 9 | High | 30 | 2 | Yes |
| 3779 | 72 | Caucasian | 5.7 | 0.07 | Positive | 8 | High | 70 | 5 | Yes |
| 3795 | 64 | Caucasian | 7.6 | 0.06 | Positive | 7 | Intermediate | 90 | 8 | Yes |
| 3819 | 66 | Caucasian | 8.4 | 0.23 | Positive | 7 | Intermediate | 20 | 4 | Yes |
| 3828 | 50 | Caucasian | 8.2 | 0.25 | Positive | 9 | High | 90 | 6 | Yes |
| 3858 | 61 | Caucasian | 3.1 | 0.06 | Positive | 7 | Intermediate | 80 | 5 | Yes |
| 3860 | 72 | Black | 26.2 | 0.79 | Positive | 10 | High | 60 | 7 | Yes |
| 3864 | 63 | Caucasian | 5.4 | 0.09 | Positive | 6 | Low | 5 | 1 | No |
| 3930 | 58 | Caucasian | 6.9 | 0.27 | Positive | 6 | Low | 10 | 3 | Yes |
| 3974 | 77 | Caucasian | 8.7 | 0.09 | Positive | 6 | Low | 20 | 4 | Yes |
| 3986 | 80 | Caucasian | 8.5 | 0.06 | Positive | 6 | Low | 5 | 1 | No |
| 3987 | 62 | Unknown | 9.7 | 0.08 | Positive | 6 | Low | ? | ? | No |

[a] PSA density calculated as PSA (ng/mL) divided by prostate volume (cc) as determined by ultrasound or MRI.
[b] Risk status based on D'Amico risk classification (D'Amico AV, et al. (1998) Jama 280(11): 969-974).
[c] Epstein criteria for clinically insignificant prostate cancer: clinical stage T1c, PSA density <0.15 ng/mL/g, absence of Gleason pattern 4 or 5, <3 positive biopsy cores, presence of <50% tumors per core (Epstein JI, et al. (1994) Jama 271(5): 368-374).
Abbreviations: DRE, digital rectal exam; PCa, prostate cancer; PSA, prostate specific antigen.

Upon microscopic evaluation of slides following RISH, a population of cells were observed that exhibited fluorescent signal for NKX3-1 and PRAC1 resembling the punctate pattern seen in spiked prostate cell lines, as well as high PCA3 expression in a subset of these cells, indicating successful identification of urinary prostate cancer cells (FIG. 16). Other instances of fluorescent signal not originating from RISH spots were also observed. Sources of this non-specific fluorescence varied across patient samples. Broad-spectrum, granular autofluorescence, presumed to be lipofuscin granules, was found in a portion of cells from most patients. Additional autofluorescence resulted from mucus, casts and amorphous debris, which displayed a diffuse, low-intensity signal across channels. Large sheets and clumps of urothelial cells commonly exhibited strong fluorescence, often with a punctate appearance.

Following image acquisition and scoring of this patient cohort, NKX3-1/PRAC1+ cells were detected in 11 (58%) patients, 6 (32%) of which were also PCA3 positive. Four patients were negative for cells of prostatic origin, and the remaining 4 patients had indeterminate biomarkers status (Table 8 and Table 10).

TABLE 10

Urine specimen characteristics and RISH results (cohort 1, n = 19)

| Patient No. | Volume (mL) [a] | Total cell count | Adequate for scoring? | Reason for exclusion [b] | NKX3-1/ PRAC1 positive | NKX3-1/ PRAC1+ cell count | PCA3 positive | PCA3+ cell count | RISH result |
|---|---|---|---|---|---|---|---|---|---|
| 3539 | 50 | 9520 | Yes | N/A | No | 0 | No | 0 | No prostate cells |

TABLE 10-continued

Urine specimen characteristics and RISH results (cohort 1, n = 19)

| Patient No. | Volume (mL)[a] | Total cell count | Adequate for scoring? | Reason for exclusion[b] | NKX3-1/ PRAC1 positive | NKX3-1/ PRAC1+ cell count | PCA3 positive | PCA3+ cell count | RISH result |
|---|---|---|---|---|---|---|---|---|---|
| 3650 | 10 | 4358 | Yes | N/A | Yes | ≥1 | No | 0 | Cancer negative |
| 3688 | 20 | 11341 | Yes | N/A | Yes | ≥1 | Yes | ≥1 | Cancer positive |
| 3689 | 20 | 910 | Yes | N/A | Yes | ≥1 | No | 0 | Cancer Negative |
| 3692 | 17 | 1429 | Yes | N/A | No | 0 | No | 0 | No prostate cells |
| 3693 | 12 | 1149 | No | Obscuring | N/A | N/A | N/A | N/A | Not scored |
| 3728 | 14 | 105761 | Yes | N/A | Yes | ≥1 | Yes | ≥1 | Cancer positive |
| 3738 | 50 | 3017 | No | Obscuring | N/A | N/A | N/A | N/A | Not scored |
| 3779 | 50 | 22672 | Yes | N/A | Yes | ≥1 | No | 0 | Cancer negative |
| 3795 | 15 | 953 | Yes | N/A | Yes | ≥1 | No | 0 | Cancer negative |
| 3819 | 20 | 8877 | Yes | N/A | Yes | ≥1 | Yes | ≥1 | Cancer positive |
| 3828 | 37 | 1140 | Yes | N/A | No | 0 | No | 0 | No prostate cells |
| 3858 | 25 | 431 | Yes | N/A | Yes | ≥1 | Yes | ≥1 | Cancer positive |
| 3860 | 25 | 14811 | Yes | N/A | Yes | ≥1 | Yes | ≥1 | Cancer positive |
| 3864 | 50 | 2374 | No | Obscuring | N/A | N/A | N/A | N/A | Not scored |
| 3930 | 35 | 1152 | Yes | N/A | No | 0 | No | 0 | No prostate cells |
| 3974 | 35 | 1889 | No | Obscuring | N/A | N/A | N/A | N/A | Not scored |
| 3986 | 20 | 1395 | Yes | N/A | Yes | ≥1 | Yes | ≥1 | Cancer positive |
| 3987 | 50 | 6561 | Yes | N/A | Yes | ≥1 | No | 0 | Cancer negative |

[a] Total urine volume obtained from patient.
[b] If slide was inadequate for RISH scoring, it was excluded from analysis for one of the following reasons: "cellularity" high cellularity defined as more than 100 cells per $mm^2$ of slide deposition area; "obscuring" presence of excessive debris, cast, or other acellular factors which prevented visualization of RISH spots.

Figure 15:
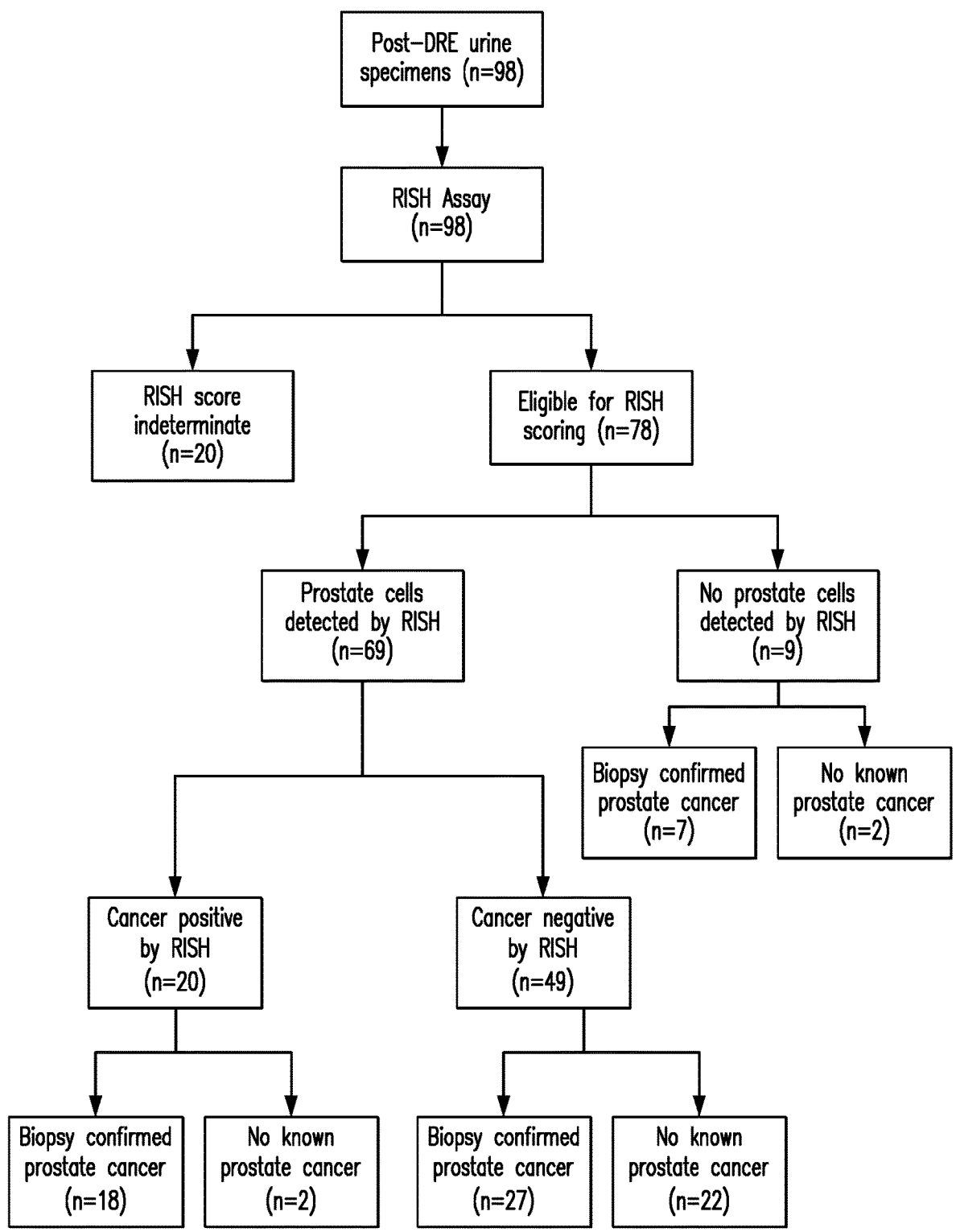
FIG. 15 is a flow diagram of patients.

Clinical performance. Ninety-eight patients were recruited (FIG. 15). The patients enrolled in the study were seen by a single physician and urine was collected immediately following an attentive DRE. Patients were instructed to collect the entire volume of urine with emphasis on catching the first-voided urine fraction. Total urine volumes obtained ranged from 10-120 mL. Patient ages ranged from 41-84 years. Serum PSA levels ranged from 0.4 to 36.6 ng/mL. Biopsy was performed on 82 patients. The remaining 16 men did not undergo biopsy and are considered negative for prostate cancer. Upon histological evaluation of biopsy samples, prostate adenocarcinoma was found in 66 patients and no cancer was detected by biopsy in 16 patients. Among the biopsy-positive cancer patients, 32 (48.5%), 27 (40.9%), and 7 (10.6%) were found to have Gleason scores of 6, 7 and >8, respectively. According to Epstein criteria, 48 cancer patients harbored clinically significant disease. Risk stratification by D'Amico criteria identified 27 (40.9%) low risk, 27 (40.9%) intermediate risk, and 12 (18.2%) high-risk cancer patients.

Figure 21A:
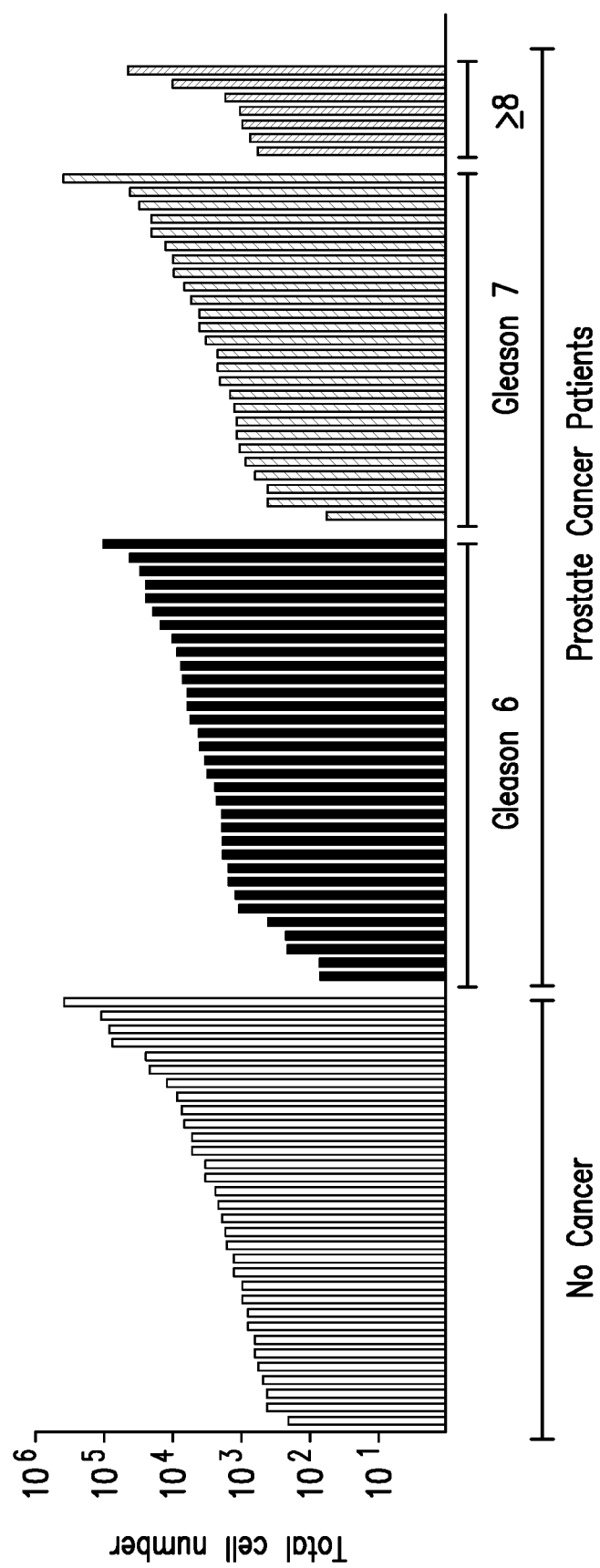
FIG. 21A shows the total cellularity of urine specimens (cohort 2, n=98).
Figure 21B:
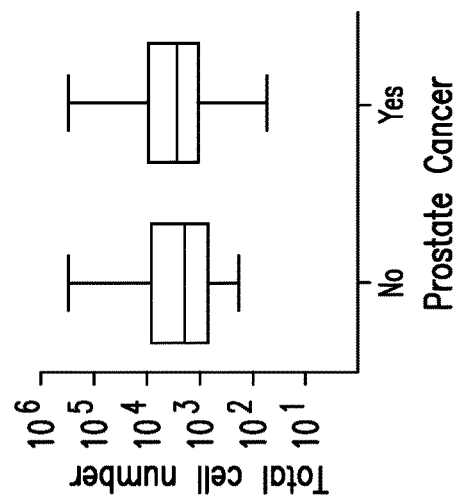
FIGS. 21B and 21C show scatter plot analysis of total cellularity of urine sediment in relation to urine sample volume and patient age.
Figure 21C:
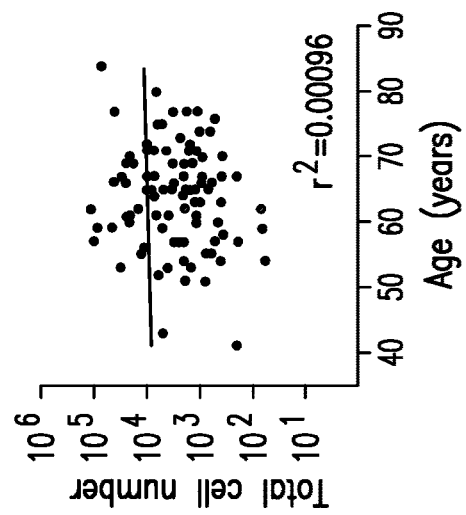
Figure 21D:
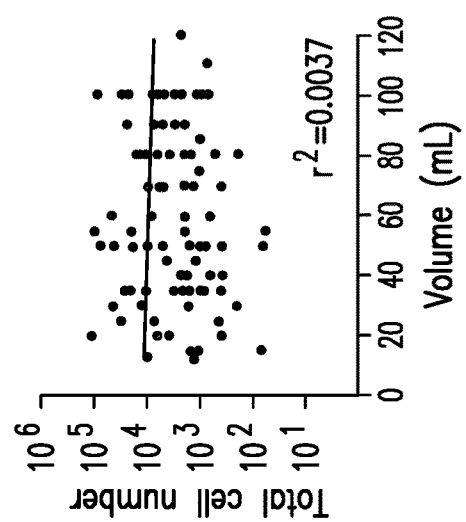
FIGS. 21 A-F shows patient cellularity.
FIG. 21E and FIG. 21F show scatter plot of absolute prostate cell number (NKX3-1/PRAC1+) and cancer cells (PCA3+) in relation to cancer status.
Figure 21E:
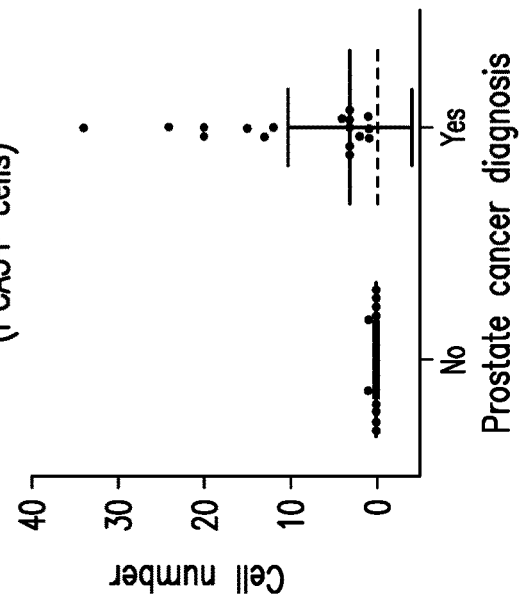
Figure 21F:
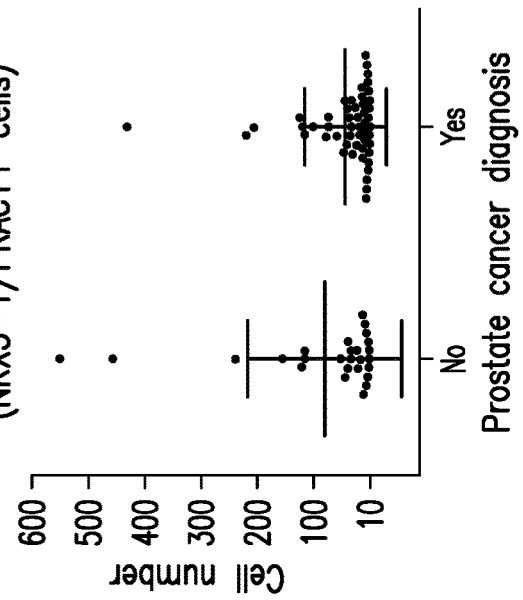
Figure 22:
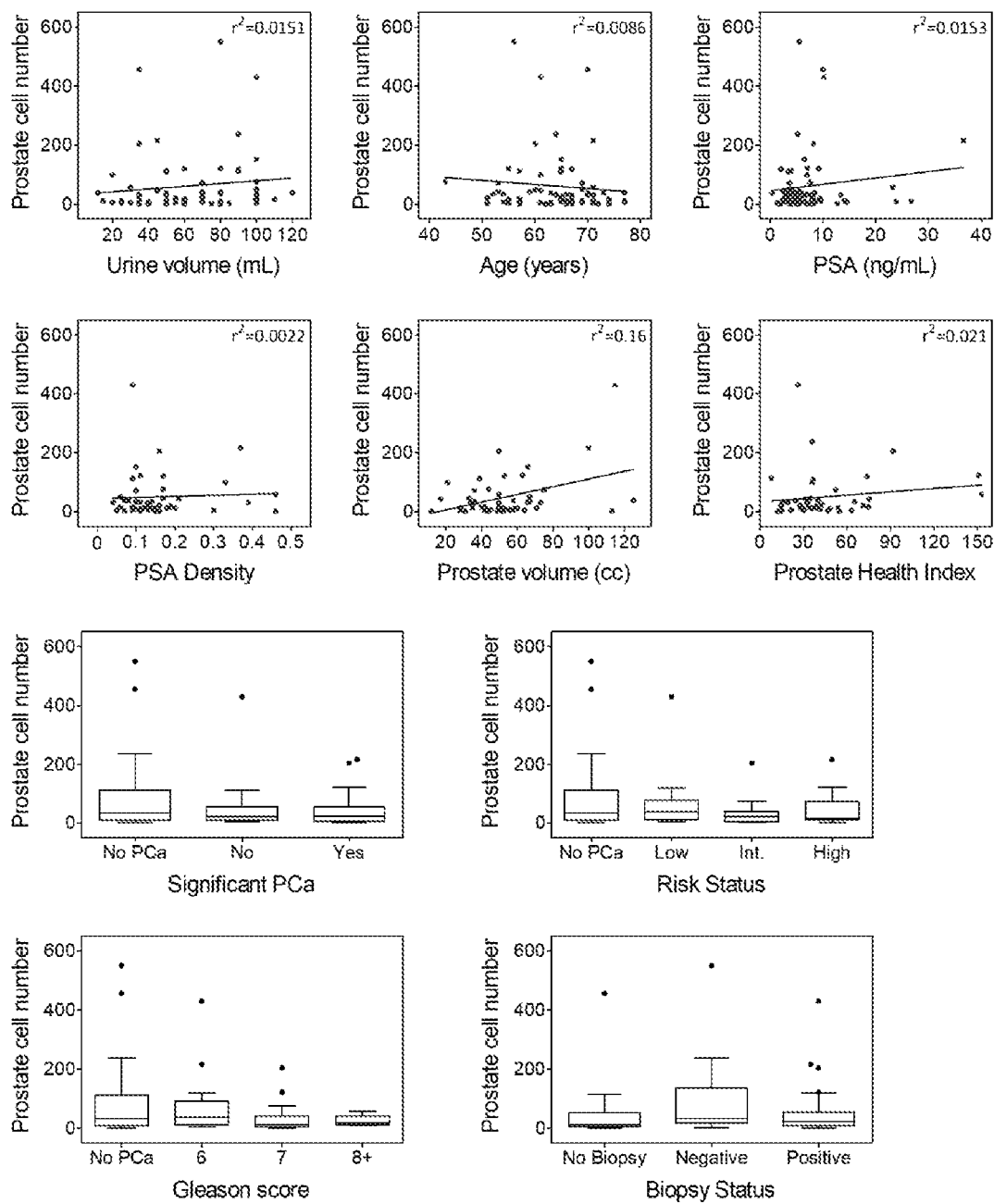
FIG. 22 shows correlations between absolute number of prostate cells (NKX3-1/PRAC1+) and clinical features for prostate positive patient samples (n=69, cohort 2).
Figure 23:
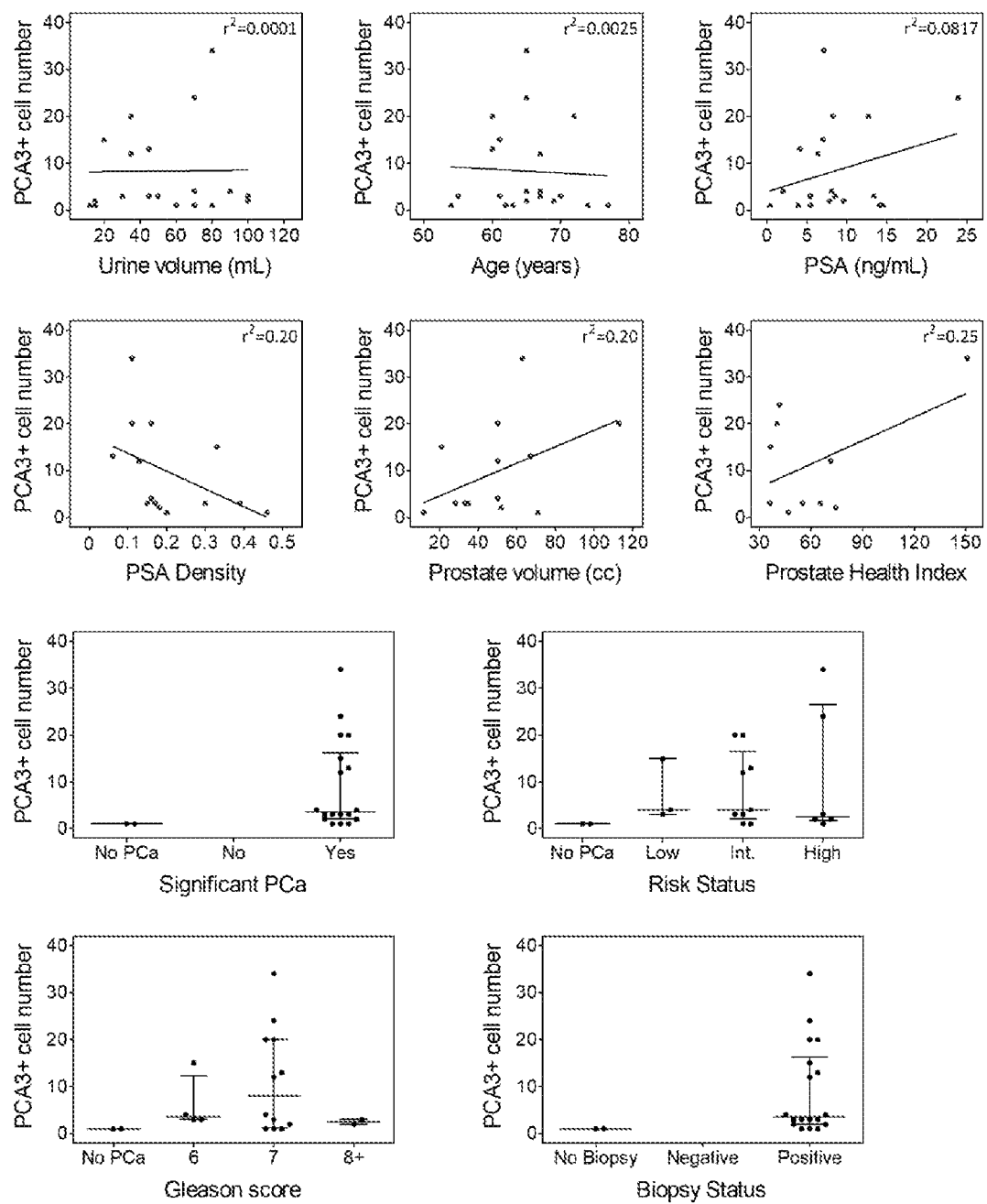
FIG. 23 shows correlations between absolute number of cancer cells (NKX3-1/PRAC1+PCA3+) and clinical features for PCA3+positive patient samples (n=20, cohort 2).
Figure 24:
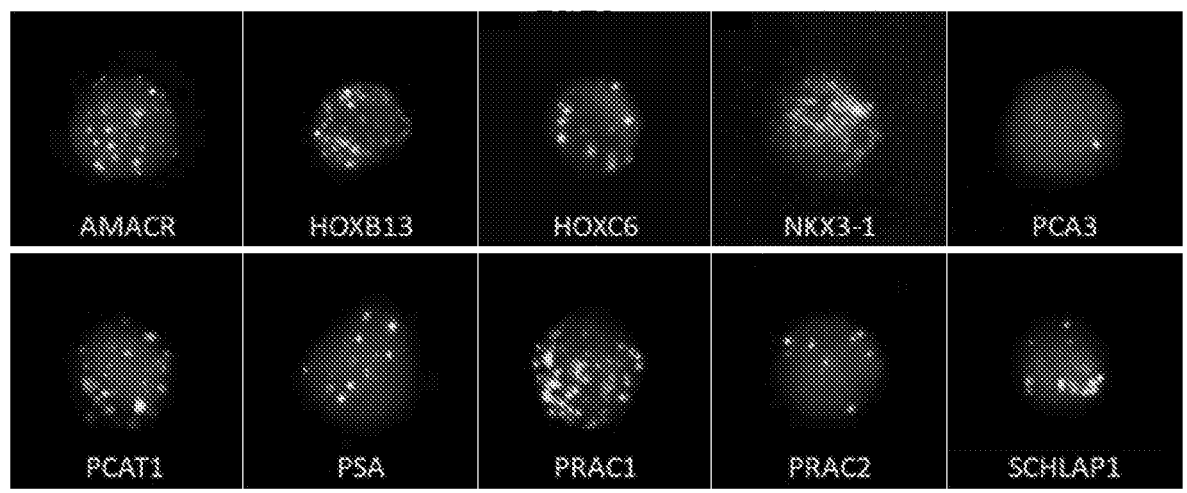
FIG. 24 shows prostate cell labeling by RISH targeting 12 different prostate markers.

Of the 98 urine specimens collected, 20 were indeterminate upon microscopic assessment. Reasons for indeterminate status were visual obstruction due to excessive debris, casts or acellular elements (n=5) and cellular overcrowding (n=15). This resulted in 78 specimens that were acceptable for analysis. The overall cellular content and quantity varied widely from patient to patient, ranging from 56 to over 300,000 cells (FIG. 21A). Total cellularity was not affected by urine volume and did not differ across patient groups (FIGS. 21B-D). The number of NKX3-1/PRAC1+ cells and PCA3+ cells ranged from 0-550 and from 0-34, respectively (FIGS. 21E-F). Absolute prostate cell counts correlated with prostate volume, but not with patient age, urine volume or other clinical variables (FIG. 22). PCA3+ cell quantity did not significantly correlate with urine volume, patient age, PSA, PSA density, prostate volume, or prostate health index (FIG. 23).

FIG. 21E shows that there was no difference in cell numbers between those with detectable prostate cells versus those without detectable prostate cells (note there are many non-prostate cells in the urine sample). FIG. 21F shows that there was no difference in cell numbers between those with detectable prostate cancer cell versus those without detectable prostate cancer cell (note the majority of cells in the urine are not prostate cancer cells). Collectively, the data show that detection is not a function of cells shed into the urine (i.e., unlikely test results can be influenced by the number of cells shed into the urine).

Of the 78 samples that were scored, 20 specimens were classified as cancer positive based on detection of prostate cancer cells (NKX3-1/PRAC1+ and PCA3+) and 58 patients were classified as cancer negative (Table 11). The cancer negative category was comprised of 49 specimens positive for cells of prostatic origin (NKX3-1/PRAC1+ and PCA3−) and 9 specimens negative for prostate cells (NKX3-1/ PRAC1− and PCA3−). Classifications for the entire patient population (n=98) are listed in Table 15. Excluding indeterminate specimens, RISH scoring accurately identified 18 of the 52 total patients with biopsy confirmed prostate adenocarcinoma (Table 14). RISH positive cells were detected in 2 of the 26 patients with no evidence of prostate cancer. RISH positivity significantly correlated with PSA density (p=0.022), risk status (p=0.034), and clinically significant disease (p<0.0001). There were no significant differences in RISH positivity by age (p=0.302), race (p=0.671), PSA (p=0.365), or Gleason (p=0.073). For detection of any prostate cancer, RISH performed with 35% sensitivity and 92% specificity. Stratification of patients according Epstein criteria for significant cancer resulted in 51% sensitivity and 95% specificity. Subgroup analysis of RISH performance characteristics are presented in Table 12.

TABLE 11

RISH results for patient cohort 2 stratified according to patient characteristics and biopsy results (n = 98)

| | RISH Classification | | | | | |
|---|---|---|---|---|---|---|
| | | Cancer negative | | | | |
| | Cancer positive | Prostate cell positive | Prostate cell negative | Indeterminate | All patients | p value |
| Markers | NKX-31/ PRAC1+ PCA3+ | NKX3-1/ PRAC1+ PCA3− | NKX3-1/ PRAC1− PCA3− | Not scored | N/A | |
| N | 20 | 49 | 9 | 20 | 98 | |
| Age, median (IQR) | 65 (61-68.5) | 65 (57-69.5) | 62 (56.5-69) | 67 (59-73.5) | 65 (59-69) | 0.302 |
| Race | | | | | | |
| Asian | 0 | 4 | 0 | 1 | 5 | 0.671 |
| White | 16 | 34 | 9 | 16 | 75 | |
| Black | 4 | 10 | 0 | 2 | 16 | |
| Other | 0 | 1 | 0 | 1 | 2 | |
| PSA (ng/mL), median (IQR) | 7.5 (5.4-11.9) | 5.2 (3.6-7.6) | 3.7 (2.9-5.0) | 7.2 (5.0-11.2) | 5.8 (3.7-8.3) | 0.365 |
| PSA Density, median (IQR) | 0.17 (0.12-0.31) | 0.11 (0.09-0.15) | 0.10 (0.06-0.16) | 0.16 (0.12-0.25) | 0.13 (0.10-0.17) | 0.022 |
| Prostate cancer diagnosis | | | | | | |
| Yes | 18 | 27 | 7 | 14 | 66 | 0.030 |
| No | 2 | 22 | 2 | 6 | 32 | |
| Gleason score | | | | | | |
| 6 | 4 | 16 | 6 | 6 | 32 | 0.073 |
| 7 | 12 | 8 | 1 | 6 | 27 | |
| ≥8 | 2 | 3 | 0 | 2 | 7 | |
| Epstein criteria | | | | | | |
| Not significant | 0 | 13 | 4 | 1 | 18 | <0.0001 |
| Significant PCa | 18 | 14 | 3 | 13 | 48 | |
| D'Amico risk status | | | | | | |
| Low | 3 | 17 | 5 | 4 | 29 | 0.034 |
| Intermediate | 9 | 8 | 2 | 8 | 27 | |
| High | 6 | 4 | 0 | 2 | 12 | |

IQR, interquartile range;
N/A, not applicable;
PSA, prostate specific antigen

TABLE 12

Performance of RISH in patient subgroups, excluding indeterminate specimens (n = 78)

| | | | Sensitivity | | Specificity | |
|---|---|---|---|---|---|---|
| | | | % | 95% CI | % | 95% CI |
| Any prostate cancer (n = 52) | vs | No prostate cancer (n = 26) | 34.6 | 0.23-0.48 | 92.3 | 0.76-0.99 |
| Clinically significant prostate cancer [a] (n = 35) | vs | No prostate cancer (n = 26) + insignificant PCa (n = 17) | 51.4 | 0.36-0.67 | 95.4 | 0.84-0.99 |

TABLE 12-continued

Performance of RISH in patient subgroups, excluding indeterminate specimens (n = 78)

|  |  |  | Sensitivity | | Specificity | |
|---|---|---|---|---|---|---|
|  |  |  | % | 95% CI | % | 95% CI |
| Gleason ≥7 (n = 26) | vs | No prostate cancer (n = 26) + Gleason 6 (n = 26) | 53.9 | 0.35-0.71 | 88.5 | 0.77-0.95 |
| Intermediate risk (n = 19) + high risk [b] (n = 10) | vs | No prostate cancer (n = 26) + low risk (n = 23) | 51.7 | 0.34-0.69 | 89.8 | 0.78-0.96 |

[a] Epstein criteria for clinically insignificant prostate cancer: clinical stage T1c, PSA density <0.15 ng/mL/g, absence of Gleason pattern 4 or 5, <3 positive biopsy cores, presence of <50% tumors per core (Epstein JI, et al. (1994) *Jama* 271(5): 368-374).
[b] Risk status based on D'Amico risk classification (D'Amico AV, et al. (1998) *Jama* 280(11): 969-974).
Abbreviations: CI, confidence interval; PCa, prostate cancer.

TABLE 13

RISH results stratified according to patient characteristics and biopsy results, excluding indeterminate samples (n = 78)

| RISH Classification | Cancer positive | Cancer negative |
|---|---|---|
| PCA3 cells | Positive | Negative |
| N | 20 | 58 |
| Age, median (IQR) | 65 (61-69) | 65 (57-69) |
| Race |  |  |
| Asian (n = 4) | 0 | 4 |
| White (n = 59) | 16 | 43 |
| Black (n = 14) | 4 | 10 |
| Other (n = 1) | 0 | 1 |
| PSA (ng/mL), median (IQR) | 7.5 (5.4-11.9) | 5.0 (3.6-7.5) |
| PSA Density, median (IQR) | 0.17 (0.12-0.31) | 0.11 (0.09-0.16) |
| Prostate cancer diagnosis |  |  |
| Yes (n = 52) | 18 | 34 |
| No (n = 26) | 2 | 24 |
| Gleason score |  |  |
| 6 (n = 26) | 4 | 22 |
| ≥7 (n = 26) | 14 | 12 |
| Epstein criteria |  |  |
| Not significant (n = 17) | 0 | 17 |
| Significant PCa (n = 35) | 18 | 17 |
| D'Amico risk status |  |  |
| Low (n = 25) | 3 | 22 |
| Intermediate (n = 19) | 9 | 10 |
| High (n = 10) | 6 | 4 |

IQR, interquartile range;
PCa, prostate cancer;
PSA, prostate specific antigen

TABLE 14

Clinical characteristics of patient population (cohort 2, n = 98)

| Patient No. | Age | Race | PSA (ng/mL) | PSA Density [a] | Prostate biopsy | Gleason score | Risk Status [b] | Tumor per core (%) | No. positive cores | Significant PCa [c] |
|---|---|---|---|---|---|---|---|---|---|---|
| 4430 | 61 | Caucasian | 8 | 0.24 | Positive | 7 | Intermediate | 100 | 10 | Yes |
| 4431 | 69 | Caucasian | 15.2 | 0.29 | Positive | 6 | Intermediate | 20 | 2 | Yes |
| 4432 | 67 | Caucasian | 4.7 | 0.10 | Positive | 9 | High | N/A | 9 | Yes |
| 4433 | 76 | Caucasian | 1.6 | Unknown | No biopsy | N/A | N/A | N/A | N/A | N/A |
| 4440 | 69 | Black | 6.1 | 0.12 | Negative | N/A | N/A | 0 | 0 | N/A |
| 4441 | 74 | Caucasian | 5.5 | 0.46 | Positive | 7 | Intermediate | 80 | 6 | Yes |
| 4442 | 62 | Caucasian | 3.9 | Unknown | Positive | 6 | High | 80 | 5 | Yes |
| 4454 | 75 | Caucasian | 7 | 0.20 | Positive | 6 | Low | 50 | 2 | Yes |
| 4455 | 67 | Caucasian | 5 | 0.16 | Positive | 7 | Intermediate | 60 | 2 | Yes |
| 4456 | 80 | Caucasian | 1.2 | Unknown | No biopsy | N/A | N/A | N/A | N/A | N/A |
| 4457 | 65 | Caucasian | 7.1 | 0.11 | Positive | 7 | High | 70 | 2 | Yes |
| 4458 | 75 | Caucasian | 6.9 | Unknown | Positive | 6 | Low | 30 | 3 | Yes |
| 4459 | 59 | Caucasian | 4.8 | Unknown | Negative | N/A | N/A | 0 | 0 | N/A |
| 4460 | 77 | Black | 7.6 | 0.17 | Positive | 7 | Intermediate | 50 | 1 | Yes |
| 4462 | 84 | Asian | 0.4 | Unknown | No biopsy | N/A | N/A | N/A | N/A | N/A |
| 4478 | 65 | Caucasian | 23.9 | Unknown | Positive | 7 | High | 50 | 4 | Yes |
| 4479 | 41 | Caucasian | 3 | 0.10 | Positive | 6 | Low | 20 | 1 | No |
| 4480 | 69 | Caucasian | 3.6 | 0.10 | Positive | 6 | Low | 40 | 2 | No |
| 4482 | 71 | Caucasian | 23.2 | 0.46 | Positive | 8 | High | 90 | 6 | Yes |
| 4483 | 71 | Caucasian | 36.6 | 0.37 | Positive | 6 | High | 100 | 4 | Yes |
| 4484 | 63 | Black | 2.2 | 0.05 | Positive | 6 | Low | 5 | 1 | No |
| 4485 | 63 | Black | 7 | 0.16 | Positive | 7 | Intermediate | 90 | 3 | Yes |

TABLE 14-continued

Clinical characteristics of patient population (cohort 2, n = 98)

| Patient No. | Age | Race | PSA (ng/mL) | PSA Density [a] | Prostate biopsy | Gleason score | Risk Status [b] | Tumor per core (%) | No. positive cores | Significant PCa [c] |
|---|---|---|---|---|---|---|---|---|---|---|
| 4492 | 51 | Asian | 3.6 | 0.07 | No biopsy | N/A | N/A | N/A | N/A | N/A |
| 4493 | 66 | Black | 7.8 | 0.15 | Negative | N/A | N/A | 0 | 0 | N/A |
| 4494 | 54 | Black | 14.5 | Unknown | No biopsy | N/A | N/A | N/A | N/A | N/A |
| 4495 | 60 | Caucasian | 8.2 | 0.16 | Positive | 7 | Intermediate | 70 | 4 | Yes |
| 4496 | 53 | Caucasian | 7.6 | 0.10 | Positive | 6 | Low | 30 | 4 | Yes |
| 4497 | 67 | Caucasian | 7.4 | 0.12 | Positive | 6 | Low | 10 | 2 | No |
| 4498 | 65 | Caucasian | 6.5 | 0.10 | Negative | N/A | N/A | 0 | 0 | N/A |
| 4499 | 53 | Caucasian | 3.5 | 0.21 | Positive | 7 | Intermediate | 50 | 1 | Yes |
| 4500 | 55 | Black | 9.2 | 0.17 | Negative | N/A | N/A | 0 | 0 | N/A |
| 4578 | 70 | Caucasian | 13.4 | 0.39 | Positive | 6 | Intermediate | 80 | 6 | Yes |
| 4579 | 65 | Caucasian | 4 | Unknown | No biopsy | N/A | N/A | N/A | N/A | N/A |
| 4580 | 70 | Caucasian | 4.7 | 0.08 | Negative | N/A | N/A | 0 | 0 | N/A |
| 4581 | 66 | Caucasian | 6.9 | 0.10 | Positive | 7 | Intermediate | 15 | 2 | Yes |
| 4593 | 77 | Black | 5.9 | Unknown | Positive | 6 | Low | N/A | 1 | No |
| 4594 | 65 | Black | 7.8 | Unknown | Positive | 8 | High | 50 | 11 | Yes |
| 4595 | 57 | Caucasian | 9.4 | 0.19 | Negative | N/A | N/A | 0 | 0 | N/A |
| 4596 | 73 | Caucasian | 8.4 | 0.07 | Positive | 6 | Low | 80 | 4 | No |
| 4597 | 54 | Black | 5.2 | 0.14 | Positive | 7 | Intermediate | 90 | 1 | Yes |
| 4598 | 61 | Caucasian | 7 | 0.33 | Positive | 6 | Low | 50 | 6 | Yes |
| 4615 | 61 | Black | 5.5 | 0.17 | Positive | 6 | Low | 20 | 1 | Yes |
| 4616 | 57 | Caucasian | 3.6 | 0.09 | Positive | 6 | Low | 20 | 1 | No |
| 4617 | 63 | Caucasian | 4.1 | 0.09 | Negative | N/A | N/A | 0 | 0 | N/A |
| 4624 | 71 | Black | 1.4 | Unknown | No biopsy | N/A | N/A | N/A | N/A | N/A |
| 4625 | 53 | Other | 11.2 | 0.41 | Positive | 7 | Intermediate | 5 | 1 | Yes |
| 4626 | 57 | Black | 1.86 | Unknown | No biopsy | N/A | N/A | N/A | N/A | N/A |
| 4627 | 65 | Caucasian | 2.8 | Unknown | No biopsy | N/A | N/A | N/A | N/A | N/A |
| 4644 | 55 | Caucasian | 4.6 | 0.09 | Negative | N/A | N/A | 0 | 0 | N/A |
| 4645 | 65 | Asian | 3.6 | Unknown | Negative | N/A | N/A | 0 | 0 | N/A |
| 4646 | 64 | Caucasian | 5.2 | Unknown | Negative | N/A | N/A | 0 | 0 | N/A |
| 4647 | 61 | Caucasian | 10.2 | 0.09 | Positive | 6 | Low | 20 | 1 | No |
| 4648 | 66 | Caucasian | 3.7 | 0.09 | Positive | 6 | Low | 10 | 2 | No |
| 4649 | 67 | Caucasian | 8.4 | 0.13 | Positive | 6 | Low | 5 | 1 | No |
| 4670 | 62 | Caucasian | 3.7 | 0.11 | Positive | 6 | Low | 10 | 1 | No |
| 4671 | 71 | Other | 2.8 | 0.04 | Negative | N/A | N/A | 0 | 0 | N/A |
| 4672 | 56 | Caucasian | 5.5 | Unknown | Negative | N/A | N/A | N/A | N/A | N/A |
| 4691 | 77 | Caucasian | 5.6 | 0.10 | Positive | 6 | Low | 5 | 2 | No |
| 4692 | 43 | Black | 7.6 | 0.17 | Positive | 7 | Intermediate | 60 | 4 | Yes |
| 4695 | 67 | Caucasian | 2 | Unknown | Positive | 6 | Low | 10 | 5 | Yes |
| 4696 | 66 | Caucasian | 11.1 | Unknown | Negative | N/A | N/A | 0 | 0 | N/A |
| 4711 | 67 | Caucasian | 5.4 | 0.15 | Positive | 9 | High | 100 | 9 | Yes |
| 4712 | 71 | Caucasian | 3.3 | 0.12 | Positive | 6 | Low | 30 | 3 | No |
| 4724 | 59 | Caucasian | 3.9 | 0.05 | Positive | 6 | Low | 30 | 5 | Yes |
| 4725 | 59 | Caucasian | 19.7 | 0.34 | Positive | 9 | High | 70 | 6 | Yes |
| 4726 | 67 | Black | 6.5 | 0.11 | Positive | 6 | Low | 5 | 4 | Yes |
| 4727 | 64 | Caucasian | 7.5 | 0.11 | Negative | N/A | N/A | 0 | 0 | N/A |
| 4760 | 72 | Caucasian | 2.7 | 0.06 | Positive | 6 | Low | N/A | 1 | No |
| 4761 | 63 | Caucasian | 0.4 | Unknown | No biopsy | N/A | N/A | N/A | N/A | N/A |
| 4762 | 57 | Caucasian | 26.7 | Unknown | Positive | 9 | High | 100 | 7 | Yes |
| 4763 | 69 | Caucasian | 6 | 0.10 | Positive | 6 | Low | 30 | 8 | Yes |
| 4794 | 60 | Caucasian | 4.1 | 0.06 | Positive | 7 | Intermediate | 80 | 7 | Yes |
| 4796 | 74 | Caucasian | 5.52 | 0.13 | Positive | 8 | High | 70 | 9 | Yes |
| 4834 | 62 | Caucasian | 15.7 | 0.16 | Positive | 6 | Intermediate | N/A | 1 | Yes |
| 4835 | 69 | Caucasian | 5 | 0.09 | Positive | 7 | Intermediate | 90 | 10 | Yes |
| 4836 | 67 | Black | 6.4 | 0.13 | Positive | 7 | Intermediate | 60 | 3 | Yes |
| 4837 | 62 | Caucasian | 13.9 | Unknown | No biopsy | N/A | N/A | N/A | N/A | N/A |
| 4842 | 51 | Caucasian | 4.68 | Unknown | Positive | 6 | Low | 10 | 2 | No |
| 4843 | 60 | Caucasian | 3.6 | Unknown | No biopsy | N/A | N/A | N/A | N/A | N/A |
| 4844 | 57 | Caucasian | 7.6 | 0.13 | Positive | 7 | Intermediate | 90 | 5 | Yes |
| 4845 | 69 | Caucasian | 9.6 | 0.18 | Positive | 7 | High | 30 | 1 | Yes |
| 4866 | 67 | Caucasian | 4.7 | 0.16 | Positive | 7 | Intermediate | 90 | 6 | Yes |
| 4867 | 58 | Caucasian | 5.6 | 0.12 | Positive | 7 | Intermediate | 60 | 2 | Yes |
| 4868 | 54 | Caucasian | 6.1 | 0.20 | Positive | 7 | Intermediate | 90 | 13 | Yes |
| 4915 | 65 | Caucasian | 8.1 | 0.16 | Positive | 7 | Intermediate | 30 | 2 | Yes |
| 4916 | 65 | Asian | 3.6 | Unknown | Negative | N/A | N/A | 0 | 0 | N/A |

TABLE 14-continued

Clinical characteristics of patient population (cohort 2, n = 98)

| Patient No. | Age | Race | PSA (ng/mL) | PSA Density [a] | Prostate biopsy | Gleason score | Risk Status [b] | Tumor per core (%) | No. positive cores | Significant PCa [c] |
|---|---|---|---|---|---|---|---|---|---|---|
| 4955 | 70 | Caucasian | 10 | Unknown | No biopsy | N/A | N/A | N/A | N/A | N/A |
| 4956 | 61 | Caucasian | 7.5 | 0.13 | Positive | 7 | Intermediate | 80 | 2 | Yes |
| 4957 | 77 | Caucasian | 14.1 | 0.20 | Positive | 7 | Intermediate | 50 | 4 | Yes |
| 5004 | 55 | Caucasian | 8.5 | 0.30 | Positive | 7 | Intermediate | 80 | 6 | Yes |
| 5005 | 66 | Caucasian | 5.3 | Unknown | No biopsy | N/A | N/A | N/A | N/A | N/A |
| 5006 | 65 | Caucasian | 2.47 | 0.06 | Positive | 6 | Low | <5% | 1 | No |
| 5013 | 69 | Caucasian | 3.7 | Unknown | No biopsy | N/A | N/A | N/A | N/A | N/A |
| 5014 | 57 | Caucasian | 14.1 | 0.16 | Positive | 6 | Intermediate | 20 | 1 | Yes |
| 5015 | 52 | Caucasian | 4 | Unknown | Positive | 6 | Low | 40 | 2 | No |
| 5016 | 59 | Asian | 2.4 | Unknown | No biopsy | N/A | N/A | N/A | N/A | N/A |
| 5017 | 71 | Caucasian | 8.5 | 0.14 | Positive | 6 | Low | 5 | 3 | No |
| 5024 | 72 | Caucasian | 12.7 | 0.11 | Positive | 7 | Intermediate | 80 | 3 | Yes |

[a] PSA density calculated as PSA (ng/mL) divided by prostate volume (cc) as determined by ultrasound or MRI.
[b] Risk status based on D'Amico risk classification (D'Amico AV, et al. (1998) *Jama* 280(11): 969-974).
[c] Epstein criteria for clinically insignificant prostate cancer: clinical stage T1c, PSA density <0.15 ng/mL/g, absence of Gleason pattern 4 or 5, <3 positive biopsy cores, presence of <50% tumors per core (Epstein JI, et al. (1994) *Jama* 271(5): 368-374).
Abbreviations: PCa, prostate cancer; PSA, prostate specific antigen; N/A, not applicable.

TABLE 15

Urine specimen characteristics and RISH results (cohort 2, n = 98)

| Patient No. | Volume (mL) [a] | Total cell count | Adequate for scoring? | Reason for exclusion [b] | NKX3-1/ PRAC1 positive | NKX3-1/ PRAC1+ cell count | PCA3 positive | PCA3+ cell count | RISH result |
|---|---|---|---|---|---|---|---|---|---|
| 4430 | 80 | 6494 | No | Cellularity | N/A | N/A | N/A | N/A | Not scored |
| 4431 | 50 | 18353 | No | Cellularity | N/A | N/A | N/A | N/A | Not scored |
| 4432 | 13 | 9606 | No | Cellularity | N/A | N/A | N/A | N/A | Not scored |
| 4433 | 80 | 521 | Yes | N/A | No | 0 | No | 0 | No prostate cells |
| 4440 | 80 | >300000 | No | Cellularity | N/A | N/A | N/A | N/A | Not scored |
| 4441 | 60 | 639 | Yes | N/A | Yes | 2 | Yes | 1 | Cancer Positive |
| 4442 | 80 | 1853 | Yes | N/A | Yes | 1 | Yes | 1 | Cancer Positive |
| 4454 | 20 | 6224 | No | Cellularity | N/A | N/A | N/A | N/A | Not scored |
| 4455 | 35 | 388 | Yes | N/A | Yes | 2 | No | 0 | Cancer Negative |
| 4456 | 100 | 6558 | No | Cellularity | N/A | N/A | N/A | N/A | Not scored |
| 4457 | 80 | 3628 | Yes | N/A | Yes | 123 | Yes | 34 | Cancer Positive |
| 4458 | 90 | 5211 | No | Cellularity | N/A | N/A | N/A | N/A | Not scored |
| 4459 | 100 | 86137 | No | Cellularity | N/A | N/A | N/A | N/A | Not scored |
| 4460 | 50 | 40948 | No | Cellularity | N/A | N/A | N/A | N/A | Not scored |
| 4462 | 50 | 74713 | No | Cellularity | N/A | N/A | N/A | N/A | Not scored |
| 4478 | 70 | 9436 | Yes | N/A | Yes | 10 | Yes | 24 | Cancer Positive |
| 4479 | 30 | 198 | Yes | N/A | No | 0 | No | 0 | No prostate cells |
| 4480 | 70 | 1853 | Yes | N/A | Yes | 72 | No | 0 | Cancer Negative |
| 4482 | 30 | 1625 | Yes | N/A | Yes | 58 | No | 0 | Cancer Negative |

TABLE 15-continued

Urine specimen characteristics and RISH results (cohort 2, n = 98)

| Patient No. | Volume (mL)[a] | Total cell count | Adequate for scoring? | Reason for exclusion[b] | NKX3-1/ PRAC1 positive | NKX3-1/ PRAC1+ cell count | PCA3 positive | PCA3+ cell count | RISH result |
|---|---|---|---|---|---|---|---|---|---|
| 4483 | 45 | 4272 | Yes | N/A | Yes | 217 | No | 0 | Cancer Negative |
| 4484 | 85 | 1017 | Yes | N/A | Yes | 4 | No | 0 | Cancer Negative |
| 4485 | 75 | 1029 | Yes | N/A | Yes | 2 | No | 0 | Cancer Negative |
| 4492 | 50 | 782 | Yes | N/A | Yes | 3 | No | 0 | Cancer Negative |
| 4493 | 40 | 600 | Yes | N/A | Yes | 2 | No | 0 | Cancer Negative |
| 4494 | 70 | 398 | Yes | N/A | Yes | 8 | Yes | 1 | Cancer Positive |
| 4495 | 35 | 20881 | Yes | N/A | Yes | 205 | Yes | 20 | Cancer Positive |
| 4496 | 70 | 1447 | Yes | N/A | Yes | 73 | No | 0 | Cancer Negative |
| 4497 | 30 | 209 | No | Obscuring | N/A | N/A | N/A | N/A | Not scored |
| 4498 | 100 | 3187 | Yes | N/A | Yes | 153 | No | 0 | Cancer Negative |
| 4499 | 80 | 3916 | Yes | N/A | Yes | 43 | No | 0 | Cancer Negative |
| 4500 | 60 | 634 | Yes | N/A | Yes | 121 | No | 0 | Cancer Negative |
| 4578 | 50 | 375 | Yes | N/A | Yes | 32 | Yes | 3 | Cancer Positive |
| 4579 | 50 | 1559 | Yes | N/A | Yes | 114 | No | 0 | Cancer Negative |
| 4580 | 50 | 906 | Yes | N/A | Yes | 38 | No | 0 | Cancer Negative |
| 4581 | 35 | 3058 | Yes | N/A | Yes | 34 | No | 0 | Cancer Negative |
| 4593 | 100 | 3194 | Yes | N/A | Yes | 40 | No | 0 | Cancer Negative |
| 4594 | 100 | 701 | Yes | N/A | Yes | 25 | Yes | 2 | Cancer Positive |
| 4595 | 100 | 2384 | Yes | N/A | Yes | 19 | No | 0 | Cancer Negative |
| 4596 | 120 | 2337 | Yes | N/A | Yes | 39 | No | 0 | Cancer Negative |
| 4597 | 80 | 1998 | Yes | N/A | Yes | 35 | No | 0 | Cancer Negative |
| 4598 | 20 | 3885 | Yes | N/A | Yes | 99 | Yes | 15 | Cancer Positive |
| 4615 | 45 | 1167 | Yes | N/A | Yes | 45 | Yes | 3 | Cancer Positive |
| 4616 | 90 | 3035 | Yes | N/A | Yes | 113 | No | 0 | Cancer Negative |
| 4617 | 20 | 391 | Yes | N/A | Yes | 7 | No | 0 | Cancer Negative |
| 4624 | 100 | 8573 | Yes | N/A | Yes | 5 | No | 0 | Cancer Negative |
| 4625 | 100 | 31565 | No | Cellularity | N/A | N/A | N/A | N/A | Not scored |
| 4626 | 80 | 189 | Yes | N/A | Yes | 1 | No | 0 | Cancer Negative |
| 4627 | 60 | 1906 | Yes | N/A | Yes | 10 | No | 0 | Cancer Negative |
| 4644 | 110 | 741 | Yes | N/A | Yes | 16 | No | 0 | Cancer Negative |
| 4645 | 50 | 4976 | Yes | N/A | Yes | 109 | No | 0 | Cancer Negative |
| 4646 | 90 | 7271 | Yes | N/A | Yes | 237 | No | 0 | Cancer Negative |
| 4647 | 100 | 23858 | Yes | N/A | Yes | 430 | No | 0 | Cancer Negative |
| 4648 | 30 | 42386 | Yes | N/A | No | 0 | No | 0 | No prostate cells |
| 4649 | 25 | 30613 | Yes | N/A | Yes | 5 | No | 0 | Cancer Negative |

TABLE 15-continued

Urine specimen characteristics and RISH results (cohort 2, n = 98)

| Patient No. | Volume (mL)[a] | Total cell count | Adequate for scoring? | Reason for exclusion[b] | NKX3-1/ PRAC1 positive | NKX3-1/ PRAC1+ cell count | PCA3 positive | PCA3+ cell count | RISH result |
|---|---|---|---|---|---|---|---|---|---|
| 4670 | 15 | 70 | Yes | N/A | No | 0 | No | 0 | No prostate cells |
| 4671 | 100 | 1183 | Yes | N/A | Yes | 32 | No | 0 | Cancer Negative |
| 4672 | 80 | 11770 | Yes | N/A | Yes | 550 | No | 0 | Cancer Negative |
| 4691 | 40 | 1808 | Yes | N/A | Yes | 8 | No | 0 | Cancer Negative |
| 4692 | 100 | 4975 | Yes | N/A | Yes | 76 | No | 0 | Cancer Negative |
| 4695 | 90 | 7394 | Yes | N/A | Yes | 119 | Yes | 4 | Cancer Positive |
| 4696 | 35 | 24375 | No | Obscuring | N/A | N/A | N/A | N/A | Not scored |
| 4711 | 100 | 928 | Yes | N/A | Yes | 13 | Yes | 3 | Cancer Positive |
| 4712 | 25 | 7137 | Yes | N/A | Yes | 12 | No | 0 | Cancer Negative |
| 4724 | 50 | 65 | Yes | N/A | No | 0 | No | 0 | No prostate cells |
| 4725 | 60 | 46187 | No | Cellularity | N/A | N/A | N/A | N/A | Not scored |
| 4726 | 40 | 2071 | Yes | N/A | Yes | 9 | No | 0 | Cancer Negative |
| 4727 | 35 | 2055 | Yes | N/A | Yes | 33 | No | 0 | Cancer Negative |
| 4760 | 80 | 1509 | Yes | N/A | No | 0 | No | 0 | No prostate cells |
| 4761 | 12 | 1264 | Yes | N/A | Yes | 38 | Yes | 1 | Cancer Positive |
| 4762 | 80 | 521 | Yes | N/A | Yes | 10 | No | 0 | Cancer Negative |
| 4763 | 90 | 23956 | No | Obscuring | N/A | N/A | N/A | N/A | Not scored |
| 4794 | 45 | 1105 | Yes | N/A | Yes | 50 | Yes | 13 | Cancer Positive |
| 4796 | 100 | 1017 | Yes | N/A | Yes | 18 | No | 0 | Cancer Negative |
| 4834 | 80 | 14975 | Yes | N/A | No | 0 | No | 0 | No prostate cells |
| 4835 | 40 | 2007 | Yes | N/A | Yes | 6 | No | 0 | Cancer Negative |
| 4836 | 35 | 841 | Yes | N/A | Yes | 30 | Yes | 12 | Cancer Positive |
| 4837 | 20 | 111269 | No | Cellularity | N/A | N/A | N/A | N/A | Not scored |
| 4842 | 55 | 1893 | Yes | N/A | Yes | 21 | No | 0 | Cancer Negative |
| 4843 | 25 | 444 | Yes | N/A | No | 0 | No | 0 | No prostate cells |
| 4844 | 90 | 1976 | No | Obscuring | N/A | N/A | N/A | N/A | Not scored |
| 4845 | 15 | 1416 | Yes | N/A | Yes | 12 | Yes | 2 | Cancer Positive |
| 4866 | 55 | >300000 | No | Cellularity | N/A | N/A | N/A | N/A | Not scored |
| 4867 | 40 | 365 | No | Obscuring | N/A | N/A | N/A | N/A | Not scored |
| 4868 | 55 | 56 | Yes | N/A | No | 0 | No | 0 | No prostate cells |
| 4915 | 70 | 1244 | Yes | N/A | Yes | 22 | Yes | 4 | Cancer Positive |
| 4916 | 35 | 1627 | Yes | N/A | Yes | 21 | No | 0 | Cancer Negative |
| 4955 | 35 | 21459 | Yes | N/A | Yes | 456 | No | 0 | Cancer Negative |

TABLE 15-continued

Urine specimen characteristics and RISH results (cohort 2, n = 98)

| Patient No. | Volume (mL)[a] | Total cell count | Adequate for scoring? | Reason for exclusion[b] | NKX3-1/PRAC1 positive | NKX3-1/PRAC1+ cell count | PCA3 positive | PCA3+ cell count | RISH result |
|---|---|---|---|---|---|---|---|---|---|
| 4956 | 55 | 20105 | Yes | N/A | Yes | 6 | No | 0 | Cancer Negative |
| 4957 | 15 | 1119 | Yes | N/A | Yes | 12 | Yes | 1 | Cancer Positive |
| 5004 | 30 | 12342 | Yes | N/A | Yes | 5 | Yes | 3 | Cancer Positive |
| 5005 | 35 | 934 | Yes | N/A | Yes | 11 | No | 0 | Cancer Negative |
| 5006 | 60 | 8355 | Yes | N/A | Yes | 17 | No | 0 | Cancer Negative |
| 5013 | 100 | 3268 | Yes | N/A | Yes | 52 | No | 0 | Cancer Negative |
| 5014 | 55 | 99843 | No | Cellularity | N/A | N/A | N/A | N/A | Not scored |
| 5015 | 70 | 5991 | Yes | N/A | Yes | 35 | No | 0 | Cancer Negative |
| 5016 | 70 | 5178 | Yes | N/A | Yes | 43 | No | 0 | Cancer Negative |
| 5017 | 50 | 9955 | Yes | N/A | Yes | 11 | No | 0 | Cancer Negative |
| 5024 | 35 | 9758 | Yes | N/A | Yes | 3 | Yes | 20 | Cancer Positive |

[a] Total urine volume obtained from patient.
[b] If slide was inadequate for RISH scoring, it was excluded from analysis for one of the following reasons: "cellularity" high cellularity defined as more than 100 cells per mm$^2$ of slide deposition area; "obscuring" presence of excessive debris, cast, or other acellular factors which prevented visualization of RISH spots.

TABLE 16

Relevance Rank Platform data

| | | Cancer negative | | | |
|---|---|---|---|---|---|
| RISH Classification | Cancer positive | Prostate cell positive | Prostate cell negative | Indeterminate | All patients |
| Markers | NKX3-1/PRAC1+ PCA3+ | NKX3-1/PRAC1+ PCA3− | NKX3-1/PRAC1− PCA3− | Not scored | N/A |
| N | 8 | 5 | 0 | 3 | 16 |
| Prostate weight (g), average (SD) | 56 (16) | 66 (31) | N/A | 51 (9) | 58 (22) |
| Distance from urethra average (SD) | 0.5 (0.3) | 0.6 (0.4) | N/A | 0.2 (0.1) | 0.5 (0.3) |
| Benign prostatic hyperplasia (n) | 3 | 2 | N/A | 0 | 5 |
| Prostatic intraepithelial neoplasia (n) | 8 | 5 | N/A | 3 | 16 |
| Inflammation (n) | 5 | 3 | N/A | 3 | 11 |
| Cribriform pattern (n) | 7 | 4 | N/A | 3 | 14 |
| Intraductal carcinoma (n) | 2 | 1 | N/A | 2 | 5 |
| Dominant Gleason | | | | | |
| 3 + 4 (n) | 4 | 4 | N/A | 1 | 9 |
| 4 + 3 (n) | 3 | 1 | N/A | 2 | 6 |
| 4 + 4 (n) | 1 | 0 | N/A | 0 | 1 |
| Grade group | | | | | |
| 2 (n) | 5 | 4 | N/A | 1 | 10 |
| 3 (n) | 3 | 1 | N/A | 2 | 6 |
| Extent of tumor | | | | | |
| Unifocal (n) | 2 | 1 | N/A | 1 | 4 |
| Multifocal (n) | 6 | 4 | N/A | 2 | 12 |
| Extraprostatic extension (n) | 3 | 1 | N/A | 2 | 6 |

Discussion. In this study, a novel approach using post-DRE urine specimens for prostate cancer detection by RISH analysis of NKX3-1, PRAC1 and PCA3 is described. This is the first evidence of a RISH application to identify prostate cancer cells in urine sediment. The most compelling finding of this study was the high specificity of RISH for detection of clinically significant prostate cancer (95%).

Many techniques have been investigated for urinary detection of prostate cancer, ranging from single gene expression assays to large proteomic profiling studies. In recent literature, polymerase chain reaction (PCR)-based detection is one of the most commonly reported approaches. PCR has proven to be a powerful strategy for measuring expression of numerous prostate cancer markers in urine as it provides quantitative measurements with high analytical sensitivity. Results from clinical studies have been promising and have led to the successful development and subsequent FDA approval of a urine test to aid in decision making in the repeat biopsy setting that measures PCA3 and PSA transcript levels in whole urine specimens (Hessels D, et al. (2003) *European urology* 44(1):8-15; discussion 15-16; and Hessels D & Schalken J A (2009) *Nature Reviews Urology* 6:255). Unfortunately, clinical usefulness of both approved and investigational tests has been underwhelming, which may be related to drawbacks associated with using PCR-based analysis for urine markers. One downside is that results rely on measurements extracted from a mixed cell population, and thus information regarding cell origin of transcripts is lost as expression levels are derived from an average of cells in the sample. Additionally, PCR does not allow for enumeration of prostate cells in a sample and visualization of intact prostate cells is not possible.

A few studies regarding cytological detection of exfoliated prostate cells by microscopic visualization have been reported. Previous attempts to detect prostate cancer by urine cytology have failed to demonstrate clinical utility, likely due to the scarce number of prostate cells present in urine sediment. However, recent advances in molecular techniques and automated imaging systems may overcome previous limitations associated with conventional methods and improve detection of rare urinary prostate cell populations. RISH labeling with prostate-specific markers was evaluated as a potential strategy for the detection of prostate cells in urine. The advantage of this approach is the ability to microscopically observe exfoliated prostate cells and visualize intracellular RNA transcripts at the single-cell level. For individual cells, quantitative measurements for multiple coding and non-coding RNA markers can be obtained and analyzed with the morphological context of intact cells. In this regard, RISH has the potential to determine the presence of cancer cells and permit the differentiation of urine cells from various origins and their pathologic states, as well as be used to categorize subpopulations with prognostic value. Moreover, highly specific amplification of targets can be achieved with minimal off-target binding, circumventing the need to use troublesome antibodies for labeling. Additionally, RISH is amenable to high-throughput automated systems and can be performed in conjunction with other types of urine tests.

A multiplex labeling strategy was implemented to identify prostate cells in urine by RISH that included three markers: NKX3-1 and PRAC1 to identify cells of prostate origin, and PCA3 to indicate malignancy cells. NKX3-1 encodes for a homeodomain transcription factor that functions in the growth regulation of prostate epithelial cells. PRAC1 encodes for a small nuclear protein highly expressed in the prostate. PCA3 is a non-coding RNA specific to the prostate gland that is overexpressed in prostate cancer and is an established prostate cancer biomarker that is measurable in post-DRE urine specimens and is used clinically to guide decision making in the repeat biopsy setting. Using this panel, a sensitivity higher than previously has been reported for cytology-based urine studies was achieved.

Among patients with informative urine specimens, it was observed an overall 35% sensitivity and 92% specificity for detection of prostate cancer. However, performance was higher (Se=51%, Sp=95%) for detection of clinically significant prostate cancer following stratification of patients by Epstein criteria. Two patients without known prostate cancer were classified as positive by RISH. Neither of these false-positive patients had undergone prostate biopsy, thus the possibility that these patients harbored undiagnosed prostate cancer cannot be excluded. For the nine patients in which no prostate cells were detected, it is unclear whether the absence of prostate cells is attributable to physiologic state of the gland or related to specimen collection and handling procedures. It is expected that prostate cells would be lacking if patients do not provide a first-catch specimen or if the DRE was not rigorous enough to dislodge prostate cells. Alternatively, low urinary prostate cells may indicate high prostate health.

There are limitations of this study. First, the urine specimens were obtained at a single site, therefore the findings require external validation. Another limitation was that one slide per patient was used for analysis. For patients whose biopsy-confirmed prostate cancer was negative by RISH, it is possible that PCA3+ cells may be detected on one of the remaining patient slides. Additionally, not all patients that were evaluated by RISH underwent biopsy.

Conclusions. These results demonstrate that cells of prostatic origin and prostate cancer cells in urine sediments can be definitively detected and visualized using a novel multiplex urine RISH assay. The identification of prostate cancer cells by this approach is highly specific for the detection of clinically significant prostate cancer.

What is claimed is:

1. A method of diagnosing and treating a human subject with an increased susceptibility for prostate cancer, the method comprising:
   a) determining the mRNA expression level of NKX3.1, PRAC1 and PCA3 in a urine sample using RNA in situ hybridization from a subject;
   b) comparing the mRNA expression level for NKX3.1, PRAC1, and PCA3 of step a) with a reference mRNA expression level for NKX3.1, PRAC1, and PCA3, wherein the reference mRNA expression level is from a normal control;
   c) determining that the subject has an increased susceptibility to prostate cancer when the sample mRNA expression level of NKX3.1, PRAC1, and PCA3 is higher compared to the reference mRNA expression level of NKX3.1, PRAC1, and PCA3, respectively; and
   d) administering a treatment of prostatectomy, radiation, chemotherapy, castration or a combination thereof to the subject with increased susceptibility to prostate cancer.

2. The method of claim 1, further comprising: testing the subject with increased susceptibility to prostate cancer to determine if the subject has prostate cancer.

3. A method of diagnosing and treating prostate cancer in a human subject with a high risk tumor using a gene expression panel, the method comprising:

a) determining the mRNA expression level of NKX3.1, PRAC1, and PCA3 in a urine sample using RNA in situ hybridization from the subject;
b) comparing the mRNA expression level of NKX3.1, PRAC1, and PCA3 from a), to the mRNA expression level of NKX3.1, PRAC1, and PCA3 from a reference sample;
c) determining that the subject has prostate cancer with a high risk tumor when the mRNA expression level of NKX3.1, PRAC1, and PCA3 from a) is higher than the mRNA expression level of NKX3.1, PRAC1, and PCA3 from the reference sample; and
d) administering a treatment of prostatectomy, radiation, chemotherapy, castration or a combination thereof to the subject with prostate cancer with the high risk tumor.

4. A method of treating a human subject with an increased susceptibility for prostate cancer, wherein the subject is diagnosed with a high risk tumor when the mRNA expression levels of NKX3.1, PRAC1, and PCA3 in the urine sample are higher than the mRNA expression levels of NKX3.1, PRAC1, and PCA3 from a reference sample; and administering a treatment of prostatectomy, radiation, chemotherapy, castration or a combination thereof to the subject with increased susceptibility to prostate cancer.

5. The method of claim 1, wherein determination of the mRNA expression level comprises: (i) contacting the urine sample with one or more labeled probes that specifically hybridize to one or more of NKX3.1, PRAC1, and PCA3, and (ii) detecting amplification of the one or more of NKX3.1, PRAC1, and PCA3.

6. The method of claim 1, wherein the prostate cancer is a high risk tumor.

7. The method of claim 1, wherein the urine sample is collected upon digital rectal exam.

8. The method of claim 1, further comprising determining the mRNA expression level of HOXB13, KLK3, PRAC2, MALAT1, HOXC6, AMACR, SCHLAP1, or PCAT1.

* * * * *